(12) United States Patent
Smith et al.

(10) Patent No.: US 9,701,627 B2
(45) Date of Patent: Jul. 11, 2017

(54) LRRK2 GTP BINDING INHIBITORS FOR TREATMENT OF PARKINSON'S DISEASE AND NEUROINFLAMMATORY DISORDERS

(71) Applicant: University of Maryland, Baltimore, Baltimore, MD (US)

(72) Inventors: Wanli Smith, Bel Air, MD (US); Fengtian Xue, Potomac, MD (US); Alexander D MacKerell, Jr., Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/740,674

(22) Filed: Jun. 16, 2015

(65) Prior Publication Data

US 2015/0361038 A1 Dec. 17, 2015

Related U.S. Application Data

(60) Provisional application No. 62/012,653, filed on Jun. 16, 2014.

(51) Int. Cl.
*C07D 295/192* (2006.01)
*C07C 311/21* (2006.01)
*C07D 213/83* (2006.01)

(52) U.S. Cl.
CPC .......... *C07C 311/21* (2013.01); *C07D 213/83* (2013.01); *C07D 295/192* (2013.01)

(58) Field of Classification Search
CPC .. C07C 311/21; C07D 213/83; C07D 295/192
USPC ...................................................... 546/268.1
See application file for complete search history.

(56) References Cited

U.S. PATENT DOCUMENTS

| | | | |
|---|---|---|---|
| 6,251,917 B1* | 6/2001 | Lubisch ................ | C07C 233/76 514/311 |
| 2003/0114499 A1* | 6/2003 | Brendel ................ | A61K 31/47 514/357 |
| 2010/0087428 A1* | 4/2010 | Mulla ................... | C07C 311/21 514/230.5 |
| 2012/0083471 A1* | 4/2012 | Townsend .............. | A61K 31/18 514/117 |

FOREIGN PATENT DOCUMENTS

WO WO2013063321 * 5/2013

OTHER PUBLICATIONS

Chemical Abstracts STN Registry database record for 931241-58-6, entered on Apr. 20, 2007.*
Chemical Abstracts STN Registry database record for RN 441009-58-1, entered on Jul. 30, 2002.*
Mannhold; J. Pharm. Sci. 2009, 98, 861-893.*

(Continued)

*Primary Examiner* — Noble Jarrell
*Assistant Examiner* — Daniel Carcanague
(74) *Attorney, Agent, or Firm* — Robert C. Netter; Dann, Dorfman, Herrell and Skillman, P.C.

(57) ABSTRACT

Compounds, and methods of using the same, are provided as therapies for the treatment leucine-rich repeat kinase-2 (LRRK2)-related disorders including, but not limited to, neurodegenerative and neuroinflammatory disorders, such as Parkinson's Disease.

6 Claims, 15 Drawing Sheets

(56) References Cited

OTHER PUBLICATIONS

Alastair D. Reith, Paul Bamborough, Karamjit Jandu, Daniele Andreotti, Lucy Mensah, Pamela Dossang, Hwan Geun Choi, Xianming Deng, Jinwei Zhang, Dario R. Alessi, Nathanael S. Gray. GSK2578215A; A potent and highly selective 2-arylmethyloxy-5-substitutent-N-arylbenzamide LRRK2 kinase inhibitor, Bioorganic & Medicinal chemistry Letters, 2012, 22, 5625-5629.
Biosa,A., Trancikova,A., Civiero,L., Glauser,L., Bubacco,L., Greggio,E., Moore,D.J. (2013) GTPase activity regulates kinase activity and cellular phenotypes of Parkinson's disease-associated LRRK2. Hum. Mol. Genet., 22, 1140-1156.
Brooks,B.R., Brooks,C.L., III, MacKerell,A.D., Jr., Nilsson,L., Petrella,R.J., Roux,B., Won,Y., Archontis,G., Bartels,C., Boresch,S., et al. (2009) Charmm: the biomolecular simulation program. J. Comput. Chem., 30, 1545-1614.
Burkhard,K., Smith,S., Deshmukh,R., MacKerell,A.D., Jr., Shapiro,P. (2009) Development of extracellular signal-regulated kinase inhibitors. Curr. Top. Med. Chem., 9, 678-689.
Chen,F., Hancock,C.N., Macias,A.T., Joh,J., Still,K., Zhong,S., MacKerell,A.D., Jr., Shapiro,P. (2006) Characterization of ATP-independent ERK inhibitors identified through in silico analysis of the active ERK2 structure. Bioorg. Med. Chem. Lett., 16, 6281-6287.
Cookson,M.R. (2010) The role of leucine-rich repeat kinase 2 (LRRK2) in Parkinson's disease. Nat. Rev. Neurosci., 11, 791-797.
Dachsel, J. C.; Farrer, M. J. LRRK2 and Parkinson disease. Arch. Neurol. 2010, 67, 542 547.
Deng,J., Lewis,P.A., Greggio,E., Sluch,E., Beilina,A., Cookson,M. R. (2008) Structure of the ROC domain from the Parkinson's disease-associated leucine-rich repeat kinase 2 reveals a dimeric GTPase. Proc. Natl. Acad. Sci. U. S. A., 105, 1499-1504.
Deng,X., Choi,H.G., Buhrlage,S.J., Gray,N. S. (2012) Leucine-rich repeat kinase 2 inhibitors: a patent review (2006-2011). Expert. Opin. Ther. Pat., 22, 1415-1426.
Deng,X., Dzamko,N., Prescott,A., Davies,P., Liu,Q., Yang,Q., Lee,J.D., Patricelli,M.P., Nomanbhoy,T.K., Alessi,D.R., Gray,N.S. (2011) Characterization of a selective inhibitor of the Parkinson's disease kinase LRRK2. Nat. Chem. Biol., 7, 203-205.
Huang,N., Nagarsekar,A., Xia,G., Hayashi,J., MacKerell,A.D., Jr. (2004) Identification of non-phosphate-containing small molecular weight inhibitors of the tyrosine kinase p56 Lck SH2 domain via in silico screening against the pY + 3 binding site. J. Med. Chem., 47, 3502-3511.
Korr,D., Toschi,L., Donner,P., Pohlenz,H.D., Kreft,B., Weiss,B. (2006) LRRK1 protein kinase activity is stimulated upon binding of GTP to its Roc domain. Cell Signal., 18, 910-920.
Krumrine,J., Raubacher,F., Brooijmans,N., Kuntz,I. (2003) Principles and methods of docking and ligand design. Methods. Biochem. Anal., 44, 443-476.
Lee,B.D., Dawson,V.L., Dawson,T.M. (2012) Leucine-rich repeat kinase 2 (LRRK2) as a potential therapeutic target in Parkinson's disease. Trends Pharmacol. Sci., 33, 365-373.
Lee,B.D., Shin,J.H., VanKampen,J., Petrucelli,L., West,A.B., Ko,H. S., Lee,Y.I., Maguire-Zeiss,K.A., Bowers,W.J., Federoff,H.J., et al. (2010) Inhibitors of leucine-rich repeat kinase-2 protect against models of Parkinson's disease. Nat. Med., 16, 998-1000.
Lewis,P.A., Greggio,E., Beilina,A., Jain,S., Baker,A., Cookson,M. R. (2007) The R1441C mutation of LRRK2 disrupts GTP hydrolysis. Biochem. Biophys. Res. Commun., 357, 668-671.
Li T, Yang D, Zhong S, Thomas JM, Xue F, Liu J, et al. Novel LRRK2 GTP-binding inhibitors reduced degeneration in Parkinson's disease cell and mouse models. Hum Mol Genet. 2014; 23: 6212-22.
Liao,J., Wu,C.X., Burlak,C., Zhang,S., Sahm,H., Wang,M., Zhang,Z.Y., Vogel,K.W., Federici,M., Riddle,S.M., et al. (2014) Parkinson disease-associated mutation R1441H in LRRK2 prolongs the "active state" of its GTPase domain. Proc. Natl. Acad. Sci. U. S. A., 111, 4055-4060.
Liu,M., Poulose,S., Schuman,E., Zaitsev,A.D., Dobson,B., Auerbach,K., Seyb,K., Cuny,G.D., Glicksman,M.A., Stein,R.L., Yue,Z. (2010) Development of a mechanism-based high-throughput screen assay for leucine-rich repeat kinase 2—discovery of LRRK2 inhibitors. Anal. Biochem., 404, 186-192.
Liu,Z., Hamamichi,S., Dae,L.B., Yang,D., Ray,A., Caldwell,G.A., Caldwell,K.A., Dawson,T.M., Smith,W.W., Dawson,V.L. (2011) Inhibitors of LRRK2 kinase attenuate neurodegeneration and Parkinson-like phenotypes in Caenorhabditis elegans and *Drosophila* Parkinson's disease models. Hum. Mol. Genet., 20, 3933-42.
Pan,Y., Huang,N., Cho,S., MacKerell,A.D., Jr. (2003) Consideration of molecular weight during compound selection in virtual target-based database screening. J. Chem. Inf. Comput. Sci., 43, 267-272.
Phillips,J.C., Braun,R., Wang,W., Gumbart,J., Tajkhorshid,E., Villa,E., Chipot,C., Skeel,R.D., Kale,L., Schulten,K. (2005) Scalable molecular dynamics with NAMD. J. Comput. Chem., 26, 1781-1802.
Tan,E.K., Schapira,A.H. (2011) LRRK2 as a therapeutic target in Parkinson's disease. Eur. J. Neurol., 18, 545-6.
Webber,P.J., Smith,A.D., Sen,S., Renfrow,M.B., Mobley,J.A., West,A.B. (2011) Autophosphorylation in the Leucine-Rich Repeat Kinase 2 (LRRK2) GTPase Domain Modifies Kinase and GTP-Binding Activities. J. Mol. Biol., 412, 94-110.
Xiong,Y., Coombes,C.E., Kilaru,A., Li,X., Gitler,A.D., Bowers,W. J., Dawson,V.L., Dawson,T.M., Moore,D.J. (2010) GTPase activity plays a key role in the pathobiology of LRRK2. PLoS. Genet., 6, e1000902.
Zhong,S., Chen,X., Zhu,X., Dziegielewska,B., Bachman,K.E., Ellenberger,T., Ballin,J.D., Wilson,G.M., Tomkinson,A.E., MacKerell,A.D., Jr. (2008) Identification and validation of human DNA ligase inhibitors using computer-aided drug design. J. Med. Chem., 51, 4553-4562.
Zhong,S., MacKerell,A.D., Jr. (2007) Binding response: a descriptor for selecting ligand binding site on protein surfaces. J. Chem. Inf. Model., 47, 2303-2315.

\* cited by examiner

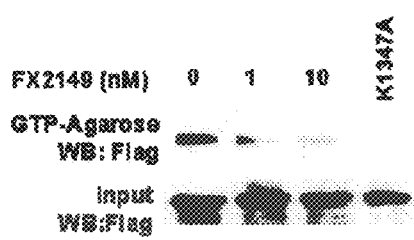
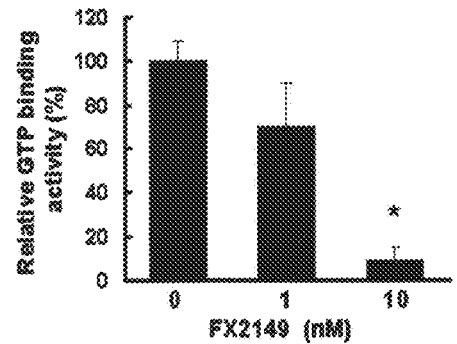
Fig. 23          Fig. 24
Fig. 25
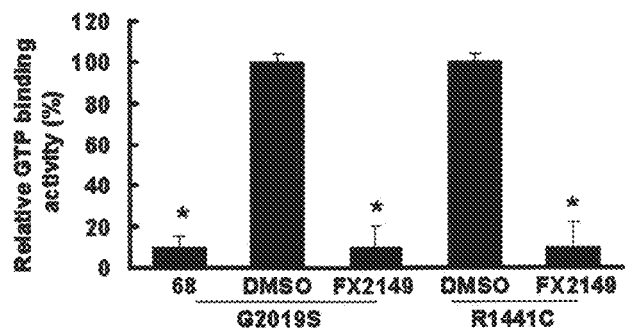
Fig. 26

LRRK2 GTP BINDING INHIBITORS FOR TREATMENT OF PARKINSON'S DISEASE AND NEUROINFLAMMATORY DISORDERS

RELATED APPLICATIONS

This application claims the benefit of priority of U.S. Provisional Application No. 62/012,653, filed Jun. 16, 2014, the entire content of which is incorporated herein by reference.

FIELD OF THE INVENTION

The present invention relates generally to compounds that inhibit leucine-rich repeat kinase-2 (LRRK2)-related activity and more particularly, but not exclusively, to compounds that inhibit GTP binding and/or protein kinase activity of LRRK2 for the treatment of neuroinflammatory disorders, such as Parkinson's Disease, and LRRK2-related disorders that implicate increased LRRK2 GTP binding and kinase activities, and neurodegeneration.

BACKGROUND OF THE INVENTION

A number of aging individuals are affected each year by neuroinflammatory and neurodegenerative disorders. Several of these disorders implicate leucine-rich repeat kinase-2 (LRRK2). For example, Parkinson's disease (PD) is a common age-related progressive neurodegenerative disorder resulting from the loss of dopaminergic neurons. Currently, there are no disease-modifying therapeutic agents to slow the neuronal degeneration of PD.

Accordingly, there is a need in the field for new and potent therapeutics for treating Parkinson's disease amongst other neuroinflammatory disorders and those disorders that implicate LRRK2.

SUMMARY OF THE INVENTION

The present invention meets the needs in the field by providing compounds and methods for the treatment of neuroinflammatory disorders and leucine-rich repeat kinase-2 (LRRK2)-related disorders that implicate increased LRRK2 GTP binding and kinase activities, and LRRK2-induced neurodegeneration. Mutations in the LRRK2 gene cause autosomal-dominant Parkinson's disease (PD) and contribute to sporadic PD. LRRK2 contains GTP binding, GTPase, and kinase activities that have been implicated in the neuronal degeneration of PD pathogenesis, making LRRK2 a potential drug target. As used herein, the terms "neuroinflammatory disorders" and "neurodegenerative disorders" include Parkinson's Disease, Amyotrophic Lateral Sclerosis (ALS), Multiple Sclerosis (MS), Alzheimer's Disease (AD), Traumatic Brain Injury (TBI), and the like. In certain preferred aspects, the present compounds and methods of the invention are provided for the treatment of Parkinson's Disease.

In one aspect, the present invention includes compounds of formula (I):

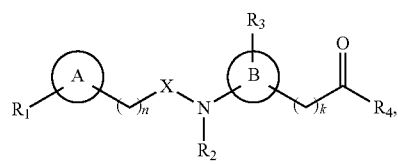

wherein $R_1$ and $R_3$ may each represent one or more substituents independently selected from the group consisting of H, OH, $NO_2$, CN, halogen, and substituted or unsubstituted alkyl, alkenyl, alkynyl, cycloalkyl, aryl, heterocycle, heteroaryl, amino, alkoxy, carboxy, carbalkoxy, carboxamido, sulfonyl, sulfinyl, monoalkylaminosulfinyl, dialkylaminosulfinyl, monoalkylaminosufonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, and dialkylaminosulfinylalkyl;

A and B may be independently selected from aryl, heteroaryl, cycloalkyl, and heterocycle moieties; n and k may be independent integers selected from 0-2;

X may be C(=O) or S(=O)$_2$;

$R_2$ may be selected from H, and substituted or unsubstituted alkyl, and sulfonyl;

$R_4$ may be —$NR_5R_6$ or —$OR_5$, wherein $R_5$ and $R_6$ may be independently selected from H, and substituted or unsubstituted alkyl, aryl, heteroaryl, heterocycle, and cycloalkyl; and the pharmaceutically acceptable salts of said compound. Encompassed within the scope of formula I, where $R_4$ is —$NR_5R_6$, $R_5$ and $R_6$ may be taken together to form a substituted or unsubstituted heterocycle (e.g., piperazine, piperdine, morpholine, and the like).

According to another aspect, the present invention presents compounds of formula (I), above, with the proviso that the following compounds are outside the scope of this aspect of the invention:

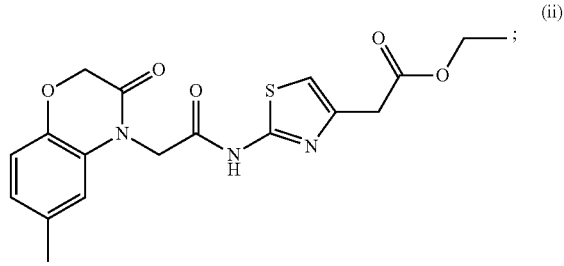

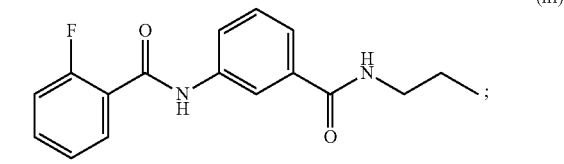

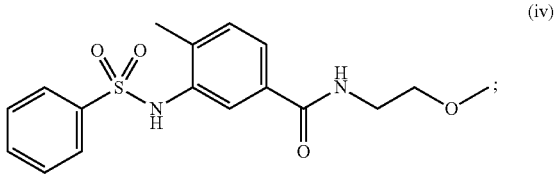

-continued (v) [structure: 4-fluorobenzamide linked to 3-aminobenzamide with N-propyl]

(vi) [structure: phenylsulfonamide on methylbenzene with piperazine-N-ethyl amide]

(vii) [structure: phenylsulfonamide on methylbenzene with N-propyl amide]

(viii) [structure: phenylsulfonamide-benzamide-piperazine]; and/or (ix) [structure: phenylsulfonamide-benzamide-N-ethylpiperazine]

In another aspect, the present invention includes compounds of formula (II):

(II) [structure showing $R_7$-A-X-N($R_8$)-B($R_9$)-C(=O)-N($R_{10}$)($R_{11}$)]

wherein $R_7$ may represent one or more substituents selected from the group consisting of H, halo, OH, CN, and substituted or unsubstituted alkyl, alkenyl, alkynyl, cycloalkyl, aryl, heterocycle, heteroaryl, amino, alkoxy, carboxy, carbalkoxy, and carboxamido;

A may be selected from the group consisting of phenyl, pyridine, pyrazine, pyridazine, imidazole, thiazole, and pyrimidine moieties;

B may be selected from the group consisting of phenyl, pyridine, pyrazine, pyridazine, and pyrimidine moieties;

X may be C(=O) or S(=O)$_2$;

$R_8$ may be selected from the group consisting of H, and substituted or unsubstituted alkyl;

$R_9$ may represent one or more substituents selected from the group consisting of H, halo, OH, CN, and substituted or unsubstituted alkyl, amino, and alkoxy;

$R_{10}$ and $R_{11}$ may be independently selected from the group consisting of H, and substituted or unsubstituted alkyl, aryl, heteroaryl, heterocycle, and cycloalkyl; where $R_{10}$ and $R_{11}$ may be taken together to form a substituted or unsubstituted heterocycle (e.g., piperazine, piperdine, morpholine, and the like); and the pharmaceutically acceptable salts of said compound.

In one embodiment, substituent A of formula (II) comprises phenyl, pyridine, pyrazine, pyridazine, or pyrimidine moieties. In certain instances of formula (II), substituent A comprises phenyl, and $R_7$ comprises 2-fluoro, 3-fluoro, 4-fluoro, 2-chloro, 3-chloro, 4-chloro, 2-bromo, 3-bromo, 4-bromo, 2-methyl, 3-methyl, 4-methyl, 2-trifluoromethyl, 3-trifluoromethyl, 4-trifluoromethyl, 2-hydroxy, 3-hydroxy, 4-hydroxy, 2-methoxy, 3-methoxy, 4-methoxy, 2-cyano, 3-cyano, 4-cyano, 2-amino, 3-amino, 4-amino, or a combination thereof. In other instances of formula (II), substituent A comprises pyridine and $R_7$ comprises amino.

Furthermore, substituent B of formula (II) may comprise phenyl, pyridine, pyrimidine, pyrazine, or pyridazine moieties. In certain instances of formula (II), substituent B comprises phenyl, and $R_9$ comprises fluoro, chloro, bromo, methyl, trifluoromethyl, hydroxy, methoxy, cyano, amino, or a combination thereof.

Additionally, in certain instances of formula (II), $R_{10}$ may be H and $R_{11}$ may propyl, butyl, pentyl, 2-methyl propyl, 3-methyl butyl, methyl cyclopropyl, cyclopropyl, methyl oxetane, methyl cyclopentane, methyl tetrahydropyran, 2-dimethylamino-ethyl, 2-methoxy-ethyl, 4-ethyl-piperazinyl, or 4-methyl-piperazinyl. In other instances of formula (II), $R_{10}$ and $R_{11}$ may be taken together to form a heterocycle, such as, piperazinyl, 4-methyl-piperazinyl, 4-ethyl-piperazinyl, and the like.

According to another aspect, the present invention presents compounds of formula (II), above, with the proviso that the following compounds are outside the scope of this aspect of the invention:

(i) [structure: phenylsulfonamide-benzamide-N-ethyl-O-methyl]

(ii) [structure: 2-fluorobenzamide linked to 3-aminobenzamide with N-propyl]

(iii) [structure: phenylsulfonamide on methylbenzene-benzamide-N-ethyl-O-methyl]

(iv) [structure: 4-fluorobenzamide-aminobenzamide-N-propyl]

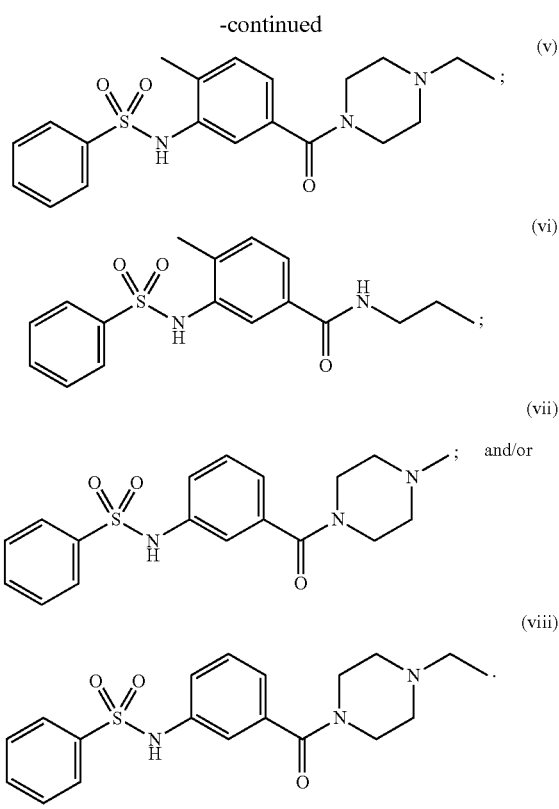

Certain compounds of formula (I) and/or (II) may be selected from the group consisting of XH10102, XH10115, XH10116, XH10117, XH10120, XH10113, XH10114, XH10119, XH10106, XH10107, XH10108, XH10110, XH10111, XH10112, XH10127, XH10128, XH10129, XH10130, XH10131, XH10132, XH10133, XH10134, XH10135, XH10126, FX2147, FX2149, FX2151, FX2153, FX2155, FX2157, FX3067, FX3069, FX3071, FX3073, FX3075, FX3076, and XH1044.

In a selected embodiment, the compound of formula (I) and/or (II) may be selected from the group consisting of FX2149, FX2147, FX2153, FX3067, XH1044, XH10102, XH10128, XH10114, XH10130, XH10132, XH10106, and XH10117.

The present invention may also include pharmaceutical compositions or medicaments that include at least one compound according to formula (I) and/or (II) and a physiologically compatible carrier medium.

In another aspect, the invention includes a method of treating or delaying the progression of a disorder alleviated by inhibiting at least one of leucine-rich repeat kinase-2 (LRRK2) GTP binding activity and LRRK2 protein kinase activity in a patient in need of said treatment. The method may include administering a therapeutically effective amount of at least one compound of formula (I) or (II), as described herein.

For example, exemplary methods of the invention may include administering a therapeutically effective amount of at least one compound selected from the group consisting of 68, 70, XH10102, XH10103, XH10104, XH10115, XH10116, XH10117, XH10120, XH10113, XH10114, XH10119, XH10121, XH10122, XH10118, XH10106, XH10107, XH10108, XH10110, XH10111, XH10112, XH10127, XH10128, XH10129, XH10130, XH10131, XH10132, XH10133, XH10134, XH10135, XH10126, FX2147, FX2149, FX2151, FX2153, FX2155, FX2157, FX3067, FX3069, FX3071, FX3073, FX3075, FX3076, XH1044, and XH1047. In certain embodiments, the methods of the invention may include administering a therapeutically effective amount of at least one compound selected from the group consisting of FX2149, FX2147, FX2153, FX3067, XH1044, XH1047, XH10102, XH10128, XH10114, XH10130, XH10132, XH10106, and XH10117.

In one embodiment, the disorder treated by the methods of the invention may be a neuroinflammatory disorder or a neurodegenerative disorder such as, for example, HIV-induced brain inflammation, Parkinson's Disease (PD), Alzheimer's disease (AD), Traumatic Brain Injury (TBI), Amyotrophic Lateral Sclerosis (ALS), or Multiple Sclerosis (MS).

In another embodiment, the method of the invention may include administering at least one compound having a calculated Log P of about 1.0 to about 3.0 and a Log BB of about −2.0 to about 1.0.

In an additional aspect, the invention includes a method of treating or delaying the progression of a disorder alleviated by inhibiting microglial activation in a patient in need of said treatment. The method may include administering a therapeutically effective amount of at least one compound of formula (I) or (II), as described herein. For example, the method may include administering a therapeutically effective amount of FX2149.

Accordingly, the present invention includes compounds, and methods of using the same, as therapies for certain diseases that implicate LRRK2, such as Parkinson's Disease.

BRIEF DESCRIPTION OF THE DRAWINGS

The foregoing summary and the following detailed description of the exemplary embodiments of the present invention may be further understood when read in conjunction with the appended drawings, in which:

FIG. 4 demonstrates representative western blots. FIG. 5 demonstrates a quantification of blots from three separated experiments.

FIG. 6 demonstrates Western blots. FIG. 7 demonstrates a quantification of LRRK2 phosphorylation normalized to that of cell lysates of G2019S-LRRK2 treated with vehicle (0.1% DMSO) (three independent experiments).

FIGS. 16 and 18 are representative blots. FIGS. 17 and 19 are the quantification data. There were three mice in each experimental group. The percentage of LRRK2 phosphorylation in the 68 group is about 46% (three animals) compared with those of the vehicle treatment group. *p<0.05 by ANOVA compared to untreated G2019S-LRRK2 transgenic mice.

FIG. 20 provides representative images of immunostaining with anti-LRRK2, anti-isolectin B4 (marker for microglia and endothelial cells), and anti-phosphorylated LRRK2 at S935 antibodies and visualized using DAB. FIG. 21 provides double immunofluorescent staining using anti-LRRK2 (red) and anti-isolectin (green) antibodies, in which the quantification of such immunofluorescent (i.e., red and green) staining is quantified in FIG. 22. Indeed, FIG. 22 provides a quantification of the immunofluorescence staining in the last panel of FIG. 21 (i.e., Overlay of LPS+68). *p<0.05 by ANOVA compared to vehicle group. #P<0.05 by ANOVA compared to LPS treated group.

FIGS. 23 to 26 demonstrate certain aspects of a study indicating that compound FX2149 inhibits LRRK2 GTP binding activity. WT or mutant LRRK2 was pulled down from lysates of transfected HEK293T cells using GTP-agarose in the absence or presence of FX2149 at 1 and 10 nM concentrations. The resulting precipitates were subjected to western blot analysis using anti-Flag antibodies. FIGS. 23 and 25 provide representative blots from GTP binding assays. FIGS. 24 and 26 graphically describe quantification of FIGS. 23 and 25, respectively. K1347A-LRRK2, non GTP binding genetic control. All experiments were repeated three times with similar results. *p<0.05 by ANOVA, vs vehicle control.

FIGS. 27 and 28 describe an assay, both by a blot (FIG. 27) and quantification of the same (FIG. 28), in which HEK293T cells were transiently transfected with Flag tagged G2019S-LRRK2 construct for 36 h and then starved with no serum media for 12 hours. Then vehicle, FX2151 (10 µM, a non-effective analog of 68), or FX2149 (10 and 100 nM) were treated for 1 h. Cell lysates were subjected to immunoprecipitation using anti-Flag antibody followed by Western blot analysis using anti-phospho-LRRK2 (S2032 or 5935) antibodies. Accordingly, FIG. 27 provides representative blots from three repeated LRRK2 phosphorylation assays and FIG. 28 graphically describes a quantification of LRRK2 phosphorylation from FIG. 27.

*p<0.05 by ANOVA compared with FX2151 treated group. FIG. 29 further demonstrates certain aspects of a study indicating that FX2149 reduces LRRK2 phosphorylation, in which LRRK2 and G2019S-LRRK2 were purified from cell lysates using anti-LRRK2 immunoprecipitation. The purified LRRK2 variants were incubated with FX2149 (0, 50, 100, or 200 nM) for 1 h and then subjected to in vitro kinase assays using $\gamma$-$^{32}$p-ATP incorporation method. LRRK2 autophosphorylation was quantified from three repeated experiments. *$p<0.05$ by ANOVA compared to wild type LRRK2. #$p<0.05$ by ANOVA compared to G2019S-LRRK2 treated with vehicle.

FIG. 30 graphically demonstrates the results of an assay in which cell viability was measured by counting the healthy viable GFP positive cells that contained at least one smooth extension (neurite) that was twice the length of the cell body. *$p<0.05$ by ANOVA compared to wild type LRRK2. #$p<0.05$ by ANOVA compared to G2019S-LRRK2 treated with vehicle. FIG. 31 graphically demonstrates TUNEL assays where the experiments were repeated three times. *$p<0.05$ by ANOVA compared to vector control. #$p<0.05$ by ANOVA compared to G2019S-LRRK2 treated with vehicle.

FIGS. 32 and 33 provide blots for LRRK2 GTP-binding assays. FIGS. 34 and 35 provide LRRK2 phosphorylation assays using anti-phospho-LRRK2 antibodies. FIGS. 36 and 37 provide FX2149 reduced G2019S-LRRK2-induced 4E-BP phosphorylation determined by anti-phospho-4E-BP western blot analysis. Ntg: non-transgenic mouse. *$p<0.05$ by ANOVA compared with G2019S-LRRK2 transgenic mice treated with vehicle.

FIG. 38 provides representative immunofluorescent images with anti-isolectin (green) and anti-LRRK2 (red) staining, in which the quantification of such immunofluorescent (i.e., red and green) staining is quantified in FIG. 39. Indeed, FIG. 39 provides a quantification of immunofluorescence staining in the last panel of FIG. 39 (i.e., Overlay of LPS+FX2149) by unbiased stereology. *$p<0.05$ by ANOVA compared with vehicle group. #$p<0.05$ by ANOVA compared with LPS treated group. Furthermore, FIG. 40 provides representative immunostaining with anti-phospho-LRRK2-5935 and anti-isolectin B4 (marker for microglia) antibodies by DAB detection.

DETAILED DESCRIPTION OF THE INVENTION

Figure 1:
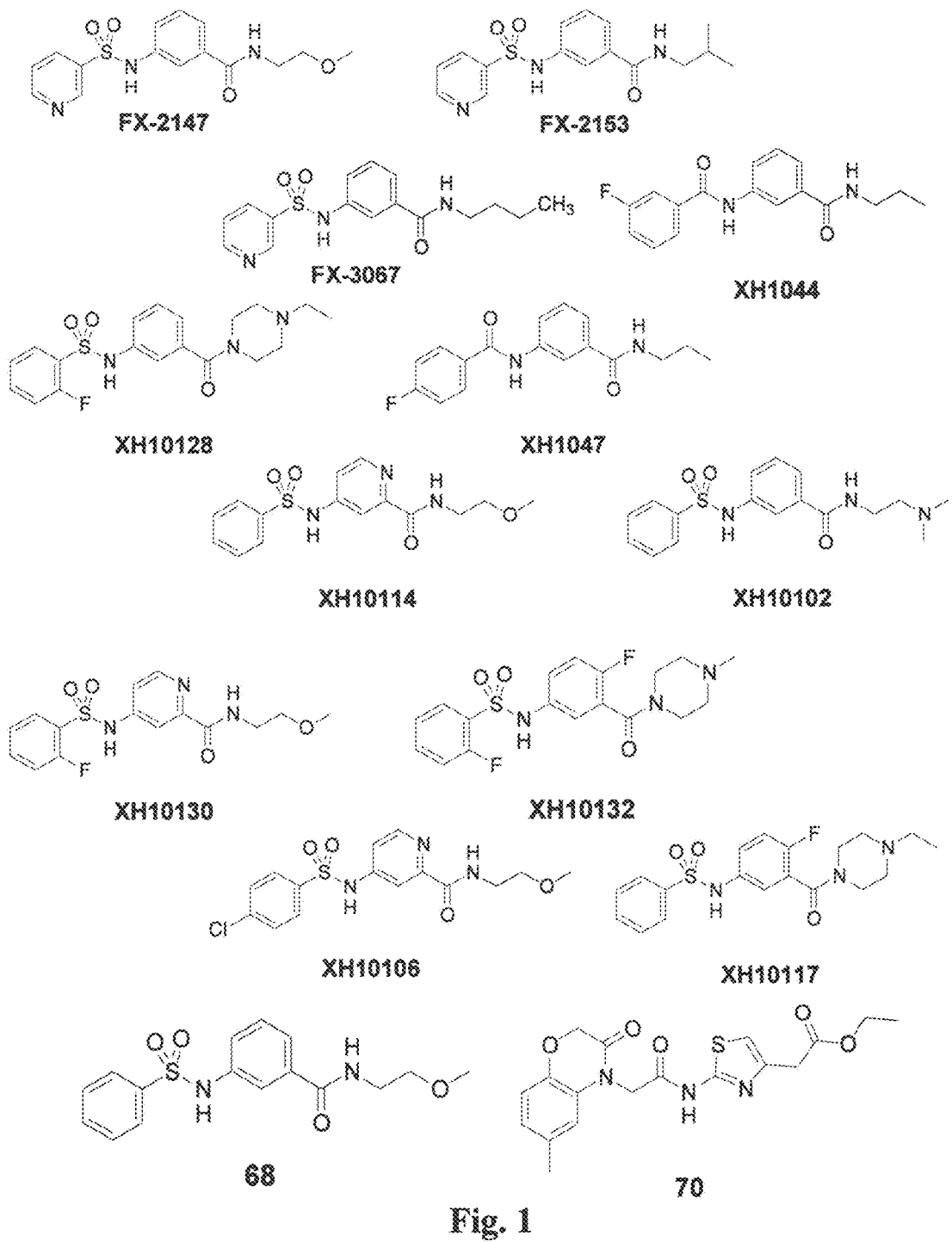
FIG. 1 schematically demonstrates specific compounds of the invention.

The present invention relates generally to compounds, and methods of using such compounds, that may inhibit certain activities of LRRK2 (e.g., GTP binding activity and protein kinase activity). More specifically, the compounds of the invention are represented in formulas I-II, which may be used in treating diseases that implicate LRRK2, such as, for example neuroinflammatory and neurodegenerative disorders (e.g., Parkinson's Disease, HIV-induced brain inflammation, Amyotrophic Lateral Sclerosis (ALS), Multiple Sclerosis (MS), Alzheimer's Disease (AD), Traumatic Brain Injury (TBI), and the like).

Regarding the compounds of the invention, which are encompassed within formulas I-II, as used herein, the term "alkyl" denotes branched or unbranched hydrocarbon chains, having about 1 to 10 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxy, halogen, mercapto or thio, cyano, alkylthio, carboxy, carboxamido, carbalkoxy, amino, nitro, alkoxy, or optionally substituted, alkenyl, alkynyl, heterocyclyl, aryl, heteroaryl, and the like to form alkyl groups such as trifluoro methyl, 3-hydroxyhexyl, 2-carboxypropyl, 2-fluoroethyl, carboxymethyl, cyanobutyl, phenethyl, benzyl and the like.

The term "halogen" or "halo" as used herein alone or as part of another group refers to chlorine, bromine, fluorine, and iodine.

The term "alkoxy" refers to alkyl-O—, in which alkyl is as defined above.

The term "alkylthio" refers to alkyl-S—, in which alkyl is as defined above.

The term "alkylamino" refers to alkyl-N—, in which alkyl is as defined above.

The term "carboxy" refers to the moiety —C(=O)OH.

The term "carbalkoxy" refers to the moiety —C(=O)O-alkyl, in which alkyl is as defined above.

The term "carboxamido" refers to the moiety —C(=O)—NR'R", in which R' and R", each may independently represent H, alkyl, or aryl, all as defined herein.

The term "alkylcarbonylamino" refers to the moiety —NR'C(=O)—R", in which R' and R", each may independently represent H, alkyl, or aryl, all as defined herein.

The term "alkylsulfonyl" refers to the moiety —S(=O)$_2$-alkyl, in which alkyl is as previously defined.

The term "arylsulfonyl" refers to the moiety —S(=O)$_2$-aryl, in which aryl is defined herein. For example, arylsulfonyl may be —S(=O)$_2$-phenyl.

The term "alkylsulfonyloxy" refers to the moiety —OS(=O)$_2$-alkyl, wherein alkyl is as previously defined.

The term "amino(monoalkylamino-, dialkylamino-)sulfinyl" refers to the moiety —S(=O)NR'R" in which R' and R" each may independently represent H, alkyl, or aryl, all as defined herein.

The term "amino(monoalkylamino-, dialkylamino-)sulfonyl" refers to the moiety —S(=O)$_2$NR'R", in which R' and R" each may independently represent H, alkyl, or aryl, all as defined herein.

The term "alkylsulfonylamino" refers to the moiety —NHS(=O)$_2$-alkyl, in which alkyl is as previously defined.

The term "hydroxysulfonyloxy" refers to the moiety —OS(=O)$_2$OH.

The term "alkoyxsulfonyloxy" refers to the moiety —OS(=O)$_2$O-alkyl, in which alkyl is as previously defined.

The term "alkylsulfonyloxy" refers to the moiety —OS(=O)$_2$-alkyl, in which alkyl is as previously defined.

The term "hydroxysulfonyl" refers to the moiety —S(=O)$_2$OH.

The term "alkoxysulfonyl" refers to the moiety —S(=O)$_2$O-alkyl, wherein alkyl is as previously defined.

The term "alkylsulfonylalkyl" refers to the moiety -alkyl-S(=O)$_2$-alkyl, wherein each alkyl may be as previously defined.

The term "amino(monoalkylamino-, dialkylamino-)sulfonylalkyl" refers to the moieties -alkyl-S(=O)$_2$—NR'R", wherein alkyl is as previously defined, and R' and R" each may independently represent H, alkyl, or aryl, all as defined herein.

The term "amino(monoalkylamino-, dialkylamino-)sulfinylalkyl" refer to the moieties -alkyl-S(=O)—NR'R", wherein alkyl is as previously defined, and R" and R" each may independently represent H, alkyl, or aryl, all as defined herein.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl, cyclododecyl, and cyclohexenyl.

"Substituted cycloalkyl" includes a cycloalkyl group optionally substituted with 1 or more substituents such as halogen, alkyl, substituted alkyl, alkoxy, hydroxy, aryl, substituted aryl, aryloxy, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

Unless otherwise indicated, the term "aryl" or "Ar" as employed herein alone or as part of another group refers to monocyclic, bicyclic, and/or polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, such as aryl, cycloalkyl, heteroaryl, or cycloheteroalkyl rings or substituted forms thereof.

"Substituted aryl" includes an aryl group optionally substituted with one or more functional groups, such as halo, alkyl, haloalkyl (e.g., trifluoromethyl), alkoxy, haloalkoxy (e.g., difluoromethoxy), alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, alkylcarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are optionally substituted alkyl, aryl or any of the other substituents recited herein), thiol, alkylthio, arylthio, heteroarylthio, arylthioalkyl, alkoxyarylthio, alkylaminocarbonyl, arylaminocarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl and/or any of the alkyl substituents recited herein.

Unless otherwise indicated, the term "heteroaryl" as used herein alone or as part of another group refers to a 5- to 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Substituted heteroaryl also includes fused heteroaryl groups which include, for example, quinoline, isoquinoline, indole, isoindole, carbazole, acridine, benzimidazole, benzofuran, isobenzofuran, benzothiophene, phenanthroline, purine, and the like.

Moreover, the terms "heterocyclo," "heterocycle," or "heterocyclic ring," as used herein, refer to an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinylsulfoxide, thiamorpholinylsulfone, and oxadiazolyl.

As used herein, the terms "optionally substituted" or "substituted" may indicate that a chemical moiety referred to, for example, alkyl, aryl, heteroaryl, may be unsubstituted or substituted with one or more groups including, without limitation, alkyl, alkenyl, alkynyl, cycloalkyl, arylalkyl, aryl, heterocycle, heteroaryl, hydroxyl, amino, alkoxy, halogen, carboxy, carbalkoxy, carboxamido, monoalkylaminosulfinyl, dialkylaminosulfinyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, monoalkylaminosulfonylalkyl, dialkylaminosulfonylalkyl, monoalkylaminosulfinylalkyl, dialkylaminosulfinylalkyl and the like. The chemical moieties of Formulas I-II, above, that may be optionally substituted include alkyl, alkenyl, alkynyl, cycloalkyl, arylalkyl, aryl, heterocycle, and heteroaryl. For example, optionally substituted alkyl may include both propyl and 2-chloro-propyl. Additionally, "optionally substituted" is also inclusive of embodiments where the named substituent or substituents have multiple substituents rather than simply a single substituent. For example, optionally substituted aryl may include both phenyl and 3-ethyl-5-methyl-6-bromo-phenyl.

The compounds of the invention may be administered as salts, which are also within the scope of this invention. Pharmaceutically acceptable (i.e., non-toxic, physiologically compatible) salts are preferred. If the compounds of the invention have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkane carboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or para-toluene-sulfonic acid. Corresponding acid addition salts can also be formed having plural basic centers, if desired.

The compounds of the invention having at least one acid group (e.g., carboxylic acid) can also form salts with suitable bases. Representative examples of such salts include metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may also be formed.

For example, certain salts of the compounds described herein which contain a basic group include monohydrochloride, hydrogensulfate, methanesulfonate, phosphate or nitrate. Moreover, certain salts of the compounds described herein which contain an acid group include sodium, potassium and magnesium salts and pharmaceutically acceptable organic amines.

All stereoisomers of the compounds of the invention, either in a mixture or in pure or substantially pure form, are considered to be within the scope of this invention. The compounds of the invention may have asymmetric centers at any of the carbon atoms including any one of the substituents. Consequently, compounds of the invention may exist in enantiomeric or diastereomeric forms or in mixtures thereof. Furthermore, where a stereocenter existing in a compound of the invention is represented as a racemate, it is understood that the stereocenter may encompass the racemic mixture of R and S isomers, the S isomers, and the R isomers. The processes for preparation of such compounds can utilize racemates, enantiomers, or diastereomers as starting materials. When diastereomeric or enantiomeric products are prepared, they can be separated by conventional methods including, chromatographic, chiral HPLC, fractional crystallization, or distillation. Some compounds of the present invention have groups including alkenyls, iminyls, and the like, which may exist as entgegen (E) or zusammen (Z) conformations, in which case all geometric forms thereof, both E and Z, cis and trans, and mixtures thereof, are within the scope of the present invention. Accordingly, when such geometric isomeric products are prepared, they can be separated by conventional methods for example, chromatographic, HPLC, distillation or crystallization.

Specific compounds of the invention include those compounds set forth in formula II. In certain aspects, the compounds of the invention include at least one of XH10102, XH10115, XH10116, XH10117, XH10120, XH10113, XH10114, XH10119, XH10106, XH10107, XH10108, XH10110, XH10111, XH10112, XH10127, XH10128, XH10129, XH10130, XH10131, XH10132, XH10133, XH10134, XH10135, XH10126, FX2147, FX2149, FX2151, FX2153, FX2155, FX2157, FX3067, FX3069, FX3071, FX3073, FX3075, FX3076, and XH1044. Preferably, the compounds of the invention may be selected from the group consisting of FX2149, FX2147, FX2153, FX3067, XH1044, XH10102, XH10128, XH10114, XH10130, XH10132, XH10106, and XH10117. The structures of such molecules are set forth in FIG. 1 and/or Table 2.

The compounds of the invention may be used as part of a therapy or methodology in treating a variety of diseases or conditions that implicate LRRK2. Specifically, the compounds of the invention may be used for treating or delaying the progression of a disorder or disease that may be alleviated by (1) inhibiting LRRK2 GTP binding activity and/or LRRK2 protein kinase activity, (2) inhibiting or reducing microglial activation, and/or (3) preventing or deterring mutant LRRK2-induced neuronal degeneration, in a patient in need of such treatment, by administering a therapeutically effective amount of at least one compound of formula I or II.

For example, the methods of the invention may be used in the treatment of neuroinflammatory or neurodegenerative diseases, including, without limitation, Parkinson's Disease (PD), Amyotrophic Lateral Sclerosis (ALS), Alzheimer's Disease (AD), Traumatic Brain Injury (TBI) and/or Multiple Sclerosis (MS).

For example, the compounds of the invention may be used in methods of treating Parkinson's Disease (PD). Parkinson's disease (PD) is an age-related progressive neurodegenerative disorder resulting from the loss of dopaminergic neurons. LRRK2 has multiple functional domains, including a GTPase domain and a protein kinase domain, and mutations in the LRRK2 gene that increase LRRK2 GTPase activity or LRRK2 kinase activity are a major cause of PD.

Mutations in the LRRK2 gene have become a major known cause of PD. There are over 40 reported LRRK2 mutations, seven of which are disease-causing mutations. G2019S is the most common pathogenic mutation and is present in 4-8% of genetic and 1-3% of sporadic cases. There are 39% of PD patients with the G2019S mutation in North African Arabs and 13% in the United States Jewish population. The LRRK2 protein contains multiple functional domains including two functional enzymatic domains: a GTPase domain and a protein kinase domain. Most disease-causing mutations are in the GTPase and the kinase domains. The majority of these have abnormally higher kinase activity or disrupted GTP domain activity compared with wild type LRRK2. Abnormal LRRK2 kinase and GTP-domain activities likely contribute to the neurodegeneration in LRRK2-linked PD suggesting that LRRK2 is a potential target for the development of novel PD medications.

Certain LRRK2 kinase inhibitors have been identified. However, some of these agents may not be clinically viable due to non-specificity or low brain penetration. Moreover, the K1347A genetic alteration abolishes GTP binding and reduces LRRK2 kinase activity, thereby protecting against LRRK2 toxicity in cell culture, suggesting that kinase activity is regulated by GTP binding activity. The GTP domain exhibits important roles in LRRK2 biological functions by regulating neuronal growth and degeneration. The PD-linked mutation, R1441H increases 2-fold of GTP binding and kinase activities when compared to wild type LRRK2 (14). This suggests that inhibition of LRRK2 GTP binding may be an important therapeutic target for PD intervention.

As used herein, the terms "treat," "treatment," and/or "treating" may refer to the management of a disease, disorder, or pathological condition (e.g., Parkinson's Disease) with the intent to cure, ameliorate, stabilize, prevent, and/or control the disease, disorder, or pathological condition. Regarding control of the disease, disorder, or pathological condition more specifically, "control" may include the absence of disease progression, as assessed by the response to the methods recited herein, where such response may be complete (e.g., placing the disease in remission) or partial (e.g., lessening or ameliorating any symptoms associated with the disease).

Furthermore, the described methods of treatment may normally include medical follow-up to determine the therapeutic or prophylactic effect brought about in the subject undergoing treatment with the compound(s) and/or composition(s) described herein.

Molecular modeling and computer-based modeling may be used in accordance with the invention to both understand the protein targets of the therapeutic agents described herein or to direct drug design in the preparation of analogs. Data reflecting the effect of compounds of the invention on LRRK2 GTP binding, for example, or other resulting in vitro or in vivo activity data, may be used to develop a pharmacophore and pharmacophore model. As used herein, the term "pharmacophore" refers to the ensemble of steric and electronic features that are necessary to ensure the optimal supramolecular interactions with a specific biological target structure (e.g., HDAC and/or ATM) and to trigger, activate, block, inhibit or modulate the biological target's biological activity, as the case may be. See, IUPAC, *Pure and Applied Chemistry* (1998) 70: 1129-1143.

As used herein, the term "pharmacophore model" refers to a representation of points in a defined coordinate system wherein a point corresponds to a position or other characteristic of an atom or chemical moiety in a bound conformation of a ligand and/or an interacting polypeptide, protein, or ordered water. An ordered water is an observable water in a model derived from structural determination of a polypeptide or protein. A pharmacophore model can include, for example, atoms of a bound conformation of a ligand, or portion thereof. A pharmacophore model can include both the bound conformations of a ligand, or portion thereof, and one or more atoms that interact with the ligand and are from a bound polypeptide or protein. Thus, in addition to geometric characteristics of a bound conformation of a ligand, a pharmacophore model can indicate other characteristics including, for example, charge or hydrophobicity of an atom or chemical moiety. A pharmacophore model can incorporate internal interactions within the bound conformation of a ligand or interactions between a bound conformation of a ligand and a polypeptide, protein, or other receptor including, for example, van der Waals interactions, hydrogen bonds, ionic bonds, and hydrophobic interactions. A pharmacophore model can be derived from 2 or more bound conformations of a ligand.

Describing computer modeling methodologies more specifically, Computer-aided drug design (CADD) has shown utility in the identification of novel inhibitors of target proteins via database screening methods when the targeting protein crystal structure is available. Although the crystal structure of full length LRRK2 protein is not yet available, the crystal structure of the LRRK2 GTPase (ras of complex proteins or "ROC") domain complexed with GDP and $Mg^{+2}$ (PDBID 2zej) provides a structural basis for the identification of novel compounds that target this domain.

Turning to the administration of therapeutics, the compounds of the invention may be administered as described herein, or in a form from which the active agent can be derived, such as a prodrug. A "prodrug" is a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of Formulas I-II. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., a compound of formula I) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991).

In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g. organ or tumor-targeting, lymphocyte targeting), to modify or improve aqueous solubility of a drug (e.g., i.v. preparations and eyedrops), to improve topical drug delivery (e.g. dermal and ocular drug delivery), to improve the chemical/enzymatic stability of a drug, or to decrease off-target drug effects, and more generally in order to improve the therapeutic efficacy of the compounds utilized in the invention.

A compound used in practicing any method of the invention may be administered in an amount sufficient to induce the desired therapeutic effect in the recipient thereof. Thus the term "therapeutically effective amount" as used herein refers to an amount of a compound of the invention that is sufficient to treat a disease in accordance with the invention by administration of one or more of the compounds of formulas I-II or a prodrug thereof. Preferably, the therapeutically effective amount refers to the amount appropriate to inhibit LRRK2 GTP binding activity and/or LRRK2 protein kinase activity. In addition, the term therapeutically effective amount may include the amount of a compound necessary, for example, to bring about a detectable therapeutic, preventative, or ameliorative effect in a patient having a disease as set forth herein. The effect may include, for example, the reduction, prevention, amelioration, or stabilization of symptoms or conditions associated with a disease as described herein.

The compound(s) described herein may also be administered at a dose in range from about 0.01 mg to about 200 mg/kg of body weight per day. A dose of from 0.1 to 100, and preferably from 1 to 30 mg/kg per day in one or more applications per day should be effective to produce the desired result. By way of example, a suitable dose for oral administration would be in the range of 1-30 mg/kg of body weight per day, whereas a typical dose for intravenous administration would be in the range of 1-10 mg/kg of body weight per day.

Of course, as those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

The compounds used in certain methods of the invention may typically be administered from 1-4 times a day, so as to deliver the above-mentioned daily dosage. However, the exact regimen for administration of the compounds described herein will necessarily be dependent on the needs of the individual subject being treated, the type of treatment administered and the judgment of the attending medical specialist. As used herein, the term "subject" or "patient" includes both humans and animals.

In general, the compounds used in the methods of the invention can be administered in pure form or, as described herein, with physiologically compatible and/or acceptable carrier mediums, using any acceptable route known in the art, either alone or in combination with one or more other therapeutic agents. Thus, the compound(s) and/or composition(s) of the invention can be administered orally, parenterally, such as by intravenous or intraarterial infusion, intramuscular, intraperitoneal, intrathecal or subcutaneous injection, by liposome-mediated delivery, rectally, vaginally, by inhalation or insufflation, transdermally or by otic delivery.

The orally administered dosage unit may be in the form of tablets, caplets, dragees, pills, semisolids, soft or hard gelatin capsules, aqueous or oily solutions, emulsions, suspensions or syrups. Suitable dosage forms for parenteral administration include injectable solutions or suspensions, suppositories, powder formulations, such as microcrystals or aerosol spray. The active agents of the invention may also be incorporated into a conventional transdermal delivery system.

As used herein, the expression "physiologically compatible carrier medium" (or "physiologically acceptable carrier medium" and the like) includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, $20^{th}$ edition, A. R. Genaro et al., Part 5, Pharmaceutical Manufacturing, pp. 669-1015 (Lippincott Williams & Wilkins, Baltimore, Md./Philadelphia, Pa.) (2000) discloses various carriers used in formulating pharmaceutical compositions and known techniques for the preparation thereof. Except insofar as any conventional pharmaceutical carrier medium is incompatible with the compounds of the present invention, such as by producing an undesirable biological effect or otherwise interacting in an deleterious manner with any other component(s) of a formulation comprising such compounds or agents, its use is contemplated to be within the scope of this invention.

For the production of solid dosage forms, including hard and soft capsules, the agents of the invention may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. For the production of liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. For suppositories one may use excipients, such as vegetable, petroleum, animal or synthetic oils, wax, fat and polyols. For aerosol formulations, one may use compressed gases suitable for this purpose, such as oxygen, nitrogen and carbon dioxide. Pharmaceutical compositions or formulations may also contain one or more additives including, without limitation, preservatives, stabilizers, e.g., UV stabilizers, emulsifiers, sweeteners, salts to adjust the osmotic pressure, buffers, coating materials and antioxidants.

The present invention further includes controlled-release, sustained-release, or extended-release therapeutic dosage forms for administration of the compounds of the invention, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

In pharmaceutical compositions used in practicing the methods of the invention more particularly, the specified compound(s) may be present in an amount of at least 0.5 and generally not more than 95% by weight, based on the total weight of the composition, including carrier medium and/or supplemental active agent(s), if any. Preferably, the proportion of compound(s) varies between 30-90% by weight of the composition.

Regarding exemplary compounds of the invention, CADD virtual database screening was performed for 1.5 million drug-like, low-molecular weight, commercially available compounds targeting the ROC domain to identify compounds that block the GTP binding site. Selected compounds were then subjected to biological screening using GTP binding assays. Compounds 68 and 70 were identified from screens to reduce LRRK2 GTP binding activity. The biological effects of these two compounds were evaluated in a study using LRRK2-based PD cell and mouse models. These studies showed that 68 and 70 also reduced LRRK2 kinase activity but did not alter LRRK1 GTP binding and kinase activities. These compounds for example provide pharmacological tools to further dissect the LRRK2 pathophysiological functions in PD pathogenesis as well as have the potential for development into therapeutic agents for the treatment of PD.

In addition to compounds 68 and 70, the inventors synthesized additional analogs of compounds 68 and 70 with similar pharmacological effects of inhibiting LRRK2 GTP binding and kinase activities, but with better drug-like properties. For example, analogs of compounds 68 and 70 include XH10102, XH10115, XH10116, XH10117, XH10120, XH10113, XH10114, XH10119, XH10106, XH10107, XH10108, XH10110, XH10111, XH10112, XH10127, XH10128, XH10129, XH10130, XH10131, XH10132, XH10133, XH10134, XH10135, XH10126, FX2147, FX2149, FX2151, FX2153, FX2155, FX2157, FX3067, FX3069, FX3071, FX3073, FX3075, FX3076, and XH1044 (FIG. 1 and/or Table 2).

Improved drug-like properties shared by certain compounds of the invention include improved penetration of the blood brain barrier (BBB). Two predictors of BBB penetration are Log P and Log BB. As used herein, "Log P" may be defined as the base 10 logarithm of the ratio of a compound's solubility in octanol to the compound's solubility in water, and is a widely accepted measure of hydrophobicity. Log P may be measured experimentally or calculated using methods known in the art. As used herein, the term "Log BB" may be defined as the base 10 logarithm of brain to plasma concentration ratio of the solute wherein the solute is the compound under study. Log BB may be measured experimentally or calculated using methods known in the art. In selected embodiments of the invention, compounds may display a Log P of about 1.0 to about 3.0 and a Log BB of about −2.0 to about 1.0. Exemplary Log P and Log BB data may be found at least in Table 2 for compounds of the invention.

The compounds of the invention: (1) inhibit LRRK2 GTP binding activity; (2) inhibit LRRK2 protein kinase activity; (3) protect against mutant LRRK2-induced neuronal degeneration; and (4) reduce microglial activation and inflammation.

Accordingly, these compounds can be used to treat or delay onset of certain inflammatory disorders and neurodegenerative disorders, such as, for example, Parkinson's disease, and other LRRK2-related disorders. The compounds can also be used to inhibit microglia activation and to treat neuroinflammatory disorders. They are also useful as drug probes to study the functions of LRRK2 in Parkinson's disease, neuroinflammation, and other LRRK2-related diseases.

The following examples describe the invention in further detail. These examples are provided for illustrative purposes only, and should in no way be considered as limiting the invention.

EXAMPLES

Example 1

Compound 70 Reduced LRRK2 Binding GTP and Kinase Activity

Figure 2:
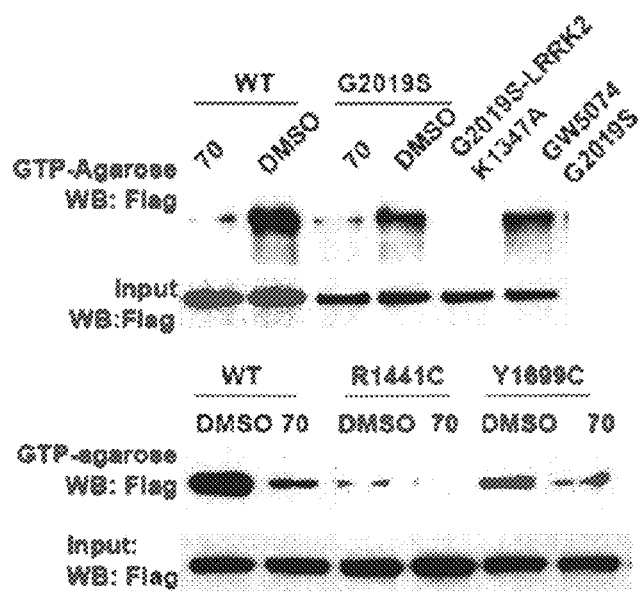
FIG. 2 demonstrates an aspect of a LRRK2 GTP binding study with compound 70, in which LRRK2 variants were affinity-purified from lysates of transfected HEK293T cells using GTP-agarose in the absence or presence of 70 or GW5074 at 10 μM with 0.1% DMSO at final concentration. The vehicle control was added as 0.1% DMSO only. Precipitates were subjected to Western blot analysis using anti-Flag antibodies. WT: wild type LRRK2.
Figure 3:
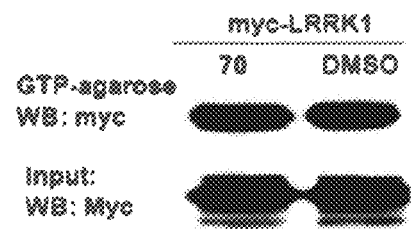
FIG. 3 demonstrates an aspect of a LRRK2 GTP binding study with compound 70, in which myc-LRRK1 was affinity-purified from lysates of transfected HEK293T cells using GTP-agarose in the absence or presence of 70 (10 μM). Precipitates were subjected to Western blot analysis using anti-myc antibodies.
Figure 4:
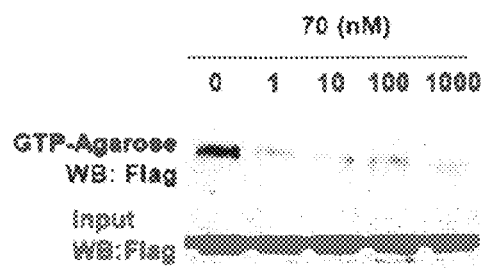
FIGS. 4 and 5 demonstrate certain aspects of a LRRK2 GTP binding study with compound 70, in which LRRK2 was affinity-purified from lysates of transfected HEK293T cells using GTP-agarose in the absence or presence of 70 (0-1000 nM). Precipitates were subjected to Western blot analysis using anti-Flag antibodies.
Figure 5:
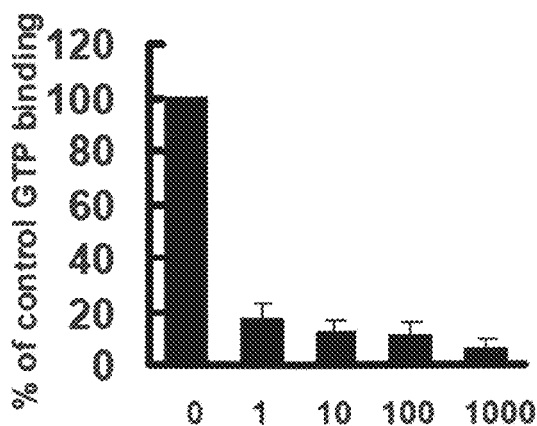

Compound 70 was the First Compound that was Identified from the combination of CADD and biological screens. Compound 70 (10 µM in 0.1% DMSO) reduced both wild type and PD-linked mutant LRRK2 (G2019S, R1441C, and Y1699C) GTP-binding activity (FIG. 2). The genetic non-GTP binding control K1347A-LRRK2 did not bind LRRK2. A LRRK2 kinase inhibitor, GW5074, did not alter the GTP-binding activity of LRRK2 (FIG. 2) and 70 (10 µM) did not alter LRRK1 (86% homology with LRRK2) GTP binding activity (FIG. 3). Moreover, 70 was relatively potent in vitro, at 1 nM reducing up to 85% of GTP binding to LRRK2 (FIGS. 4 and 5). Further reduction (<1 nM) in the concentration of 70 no longer affected the GTP binding of LRRK2.

Figure 6:
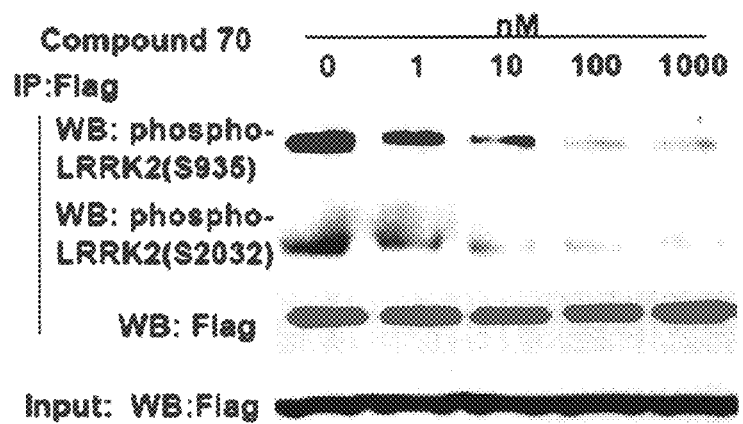
FIGS. 6 and 7 demonstrate certain aspects of a LRRK2 kinase activity study with compound 70, in which HEK-293T cells were transfected with Flag-G2019S-LRRK2 for 36 h and then starved with no serum media for 12 h. Cells were treated with vehicle or 70 (0-1000 nM) for 1 h and cells were harvested for IP using anti-Flag antibodies. The resulting immunoprecipitates were subjected to Western blot analysis using anti-phosphorylation LRRK2 antibodies (S935 or S2032).
Figure 7:
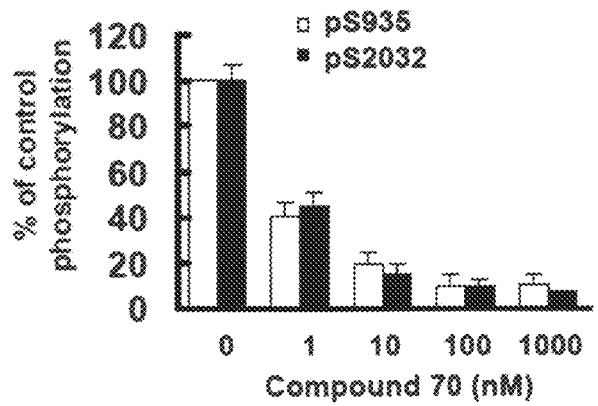
Figure 8:
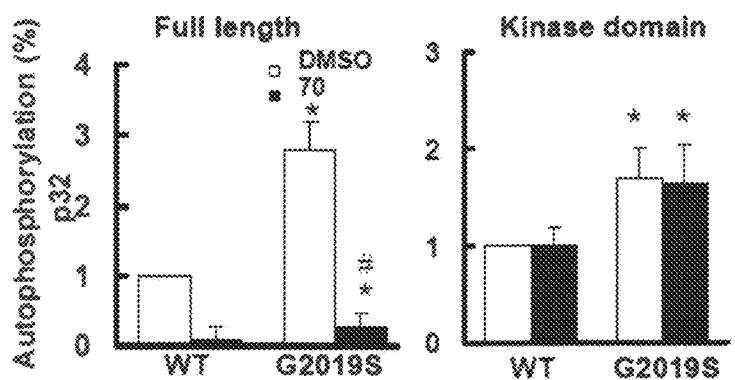
FIG. 8 demonstrates certain aspects of a LRRK2 kinase activity study with compound 70, in which 70 (10 µM) significantly reduced the autophosphorylation of G2019S full length LRRK2 but did not alter its kinase domain autophosphorylation, as seen by in vitro kinase assays.
Figure 9:
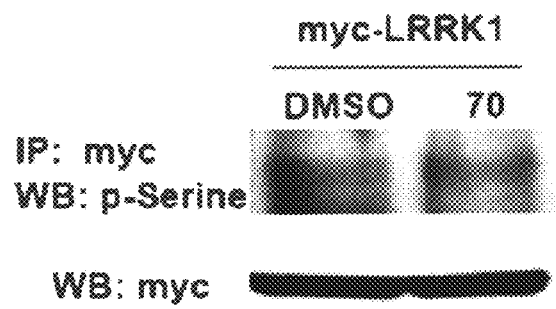
FIG. 9 demonstrates certain aspects of a LRRK2 kinase activity study with compound 70, in which 70 (10 µM) did not alter serine phosphorylation of LRRK1 using in vitro kinase assays.

Although genetic alteration of the ROC-domain GTP-binding loop at residues 1347 and 1348 reduces LRRK2 kinase activity, there is no pharmacological approach to verify the relation between GTP binding and kinase activity. Treatment of HEK293T cells expressing mutant G2019S-LRRK2 with 70 significantly inhibited LRRK2 phosphorylation at residues 5935 and 52032 in a dose-dependent manner (FIGS. 6 and 7), providing the first pharmacological evidence that disruption of GTP binding regulates LRRK2 kinase activity. Compound 70 at a concentration of 100 nM reduced kinase activity of G2019S-LRRK2 up to 90% (FIG. 7). Using in vitro autophosphorylation (kinase) assay by incorporation of $[\gamma\text{-}^{32}P]ATP$, 70 only reduced the kinase activity of full length LRRK2 protein (FIG. 8) but did not alter the kinase activity of the truncated G2019S-kinase domain (FIG. 8). Moreover, 70 also did not alter LRRK1 autophosphorylation (kinase activation), determined using an assay that immunoprecipitates LRRK1 from overexpressed cell lysates that were probed with anti-phosphorylation serine antibodies, as described previously (FIG. 9).

Compound 68 Reduced LRRK2 GTP Binding and Kinase Activities

Figures 10, 11:
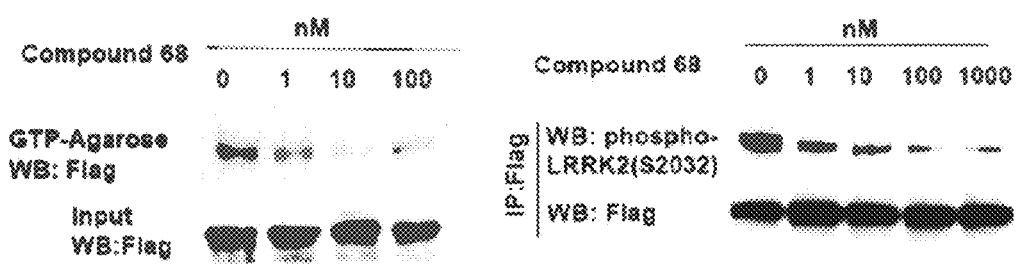
FIG. 10 demonstrates certain aspects of a LRRK2 GTP binding activity study with compound 68, in which lysates of LRRK2 transfected HEK293T cells were incubated with or without 68 (0-100 nM) for 1 h, and then added GTP-agarose to pull down GTP bounded LRRK2. The resulting precipitates were probed with anti-Flag antibodies.
FIG. 11 demonstrates certain aspects of a LRRK2 kinase activity study with compound 68, in which HEK-293T cells were transfected with Flag-G2019S-LRRK2 for 36 h and then starved with no serum media for 12 h. Cells were treated with vehicle or 68 at 0-1000 nM for 1 h. The cell lysates were subjected to IP using anti-Flag antibodies followed by Western blot analysis using anti-phosphorylation LRRK2 antibodies (S2032).
Figure 12:
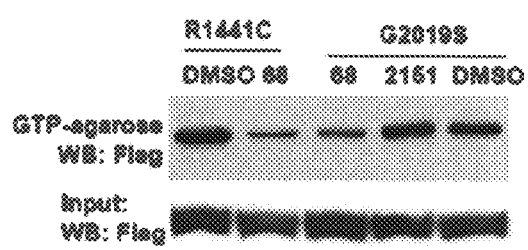
FIG. 12 demonstrates certain aspects of a LRRK2 GTP binding activity study with compound 68, in which 68 (10 µM) reduced mutant G21019S- and R1441C-LRRK2 binding GTP. FX2151 (10 µM), an analog of 68, did not alter LRRK2 binding GTP.
Figure 13:
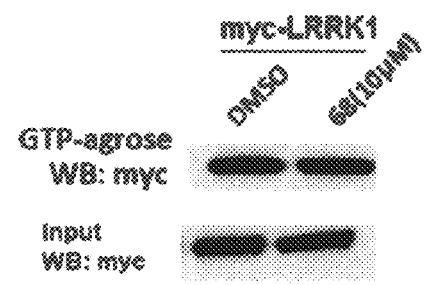
FIG. 13 demonstrates certain aspects of a LRRK2 GTP binding activity study with compound 68, in which 68 (10 µM) did not alter LRRK1 binding GTP.
Figure 14:
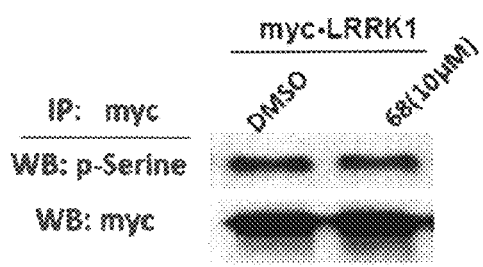
FIG. 14 demonstrates certain aspects of a LRRK2 kinase activity study with compound 68, in which HEK 293T cells were transfected with myc-LRRK1 for 36 h and starved with serum free media for 12 h, followed by addition of compound 68 at 10 µM concentration for 1 h. Cell lysates were immunoprecipitated using anti-myc antibodies followed by Western blot analysis using anti-phospho-serine antibodies. 68 did not alter serine phosphorylation of LRRK1.

Compound 68, another active compound from the CADD screen (FIG. 1), had a similar effect as 70 in reducing GTP binding LRRK2 in vitro (FIG. 10). 68 at 10 nM concentration reduced up to 90% of GTP binding activity. Moreover, treatment of 68 in HEK 293T cells expressing human G2019S-LRRK2 also reduced LRRK2 autophosphorylation (kinase activity) at residue 52032 (FIG. 11) in a similar fashion to 70. 68 also reduced mutant G2019S- and R1441C-LRRK2 binding GTP (FIG. 12). In contrast, an analog of 68, FX2151 had a similar chemical structure but did not alter GTP binding activity. 68 (10 μM) did not alter LRRK1 GTP binding (FIG. 13) and kinase activity (FIG. 14).

Figure 15:
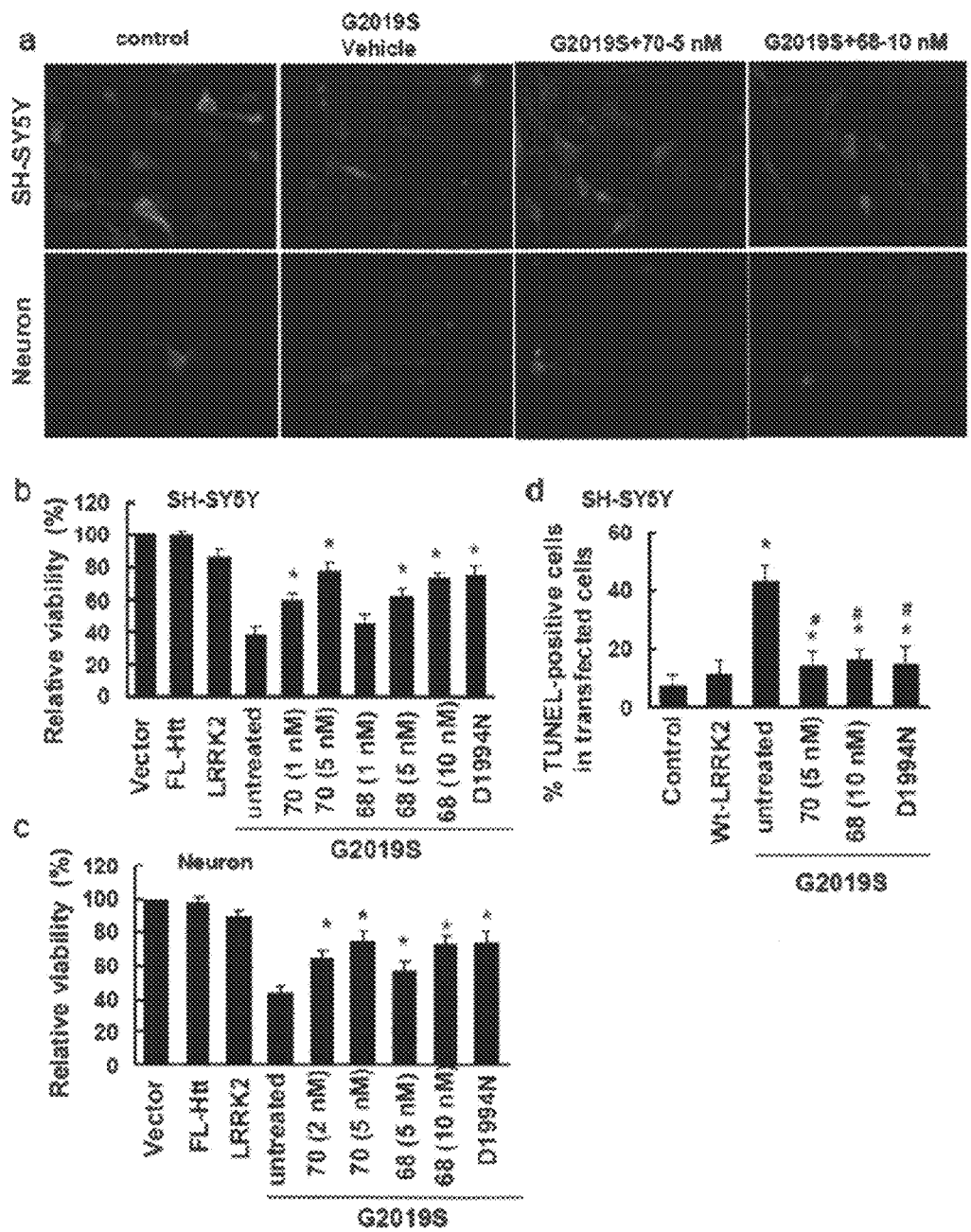
FIG. 15 provides the results of several studies demonstrating that compounds 70 and 68 suppress G2019S-LRRK2-induced neuronal degeneration in SH-SY5Y cells and mouse primary neurons. Panel (a): Representative images of SH-SY5Y cells and mouse cortical neurons expressing G2019S-LRRK2 that were treated with 70 and 68. Top panel: SH-SY5Y cells; Bottom panel: primary cortical neurons. D1994N-G2019S-LRRK2 is a kinase dead LRRK2 variant used as a positive control for neuroprotection. Panels (b) and (c): Quantification of neuronal viability in SH-SY5Y cells in panel (b) and mouse cortical primary neurons in panel (c) and normalized to the number of viable neurons transfected with eGFP and pcDNA3.1 vector in three experiments. FL-Htt: full length wild type huntingtin (non-toxic protein control). *P<0.05 by ANOVA compared to G2019S-LRRK2. Panel (d): TUNEL assays were used to detect the effects of 70 and 68 on neuronal degeneration. The TUNEL positive cells in each experimental group were quantified. *p<0.05 by ANOVA compared to eGFP control group. #p<0.05 by ANOVA compared to G2019S-LRRK2.

Both 68 and 70 Suppress Mutant LRRK2-Induced Neuronal Degeneration in Cultured Neurons Expression of mutant G2019S-LRRK2 led to neuronal degeneration in both SH-SY5Y and mouse primary cortical neurons as assessed by cell viability and DNA fragmentation (TUNEL) assays as previously described. Treatment of SH-SY5Y cells with 70 (1 and 5 nM) or 68 (5 and 10 nM) significantly attenuated G2019S-LRRK2-induced neuronal degeneration (FIG. 15, panels (a) and (b)). To further confirm these findings, mouse primary cortical neurons were used to assess the effects of 70 and 68. Treatment of 70 (2 and 5 nM) and 68 (5 and 10 nM) protected against mutant LRRK2-induced neuronal degeneration (FIG. 15, panels (a) and (c)). Moreover, 70 and 68 both decreased the TUNEL-positive SH-SY5Y cells expressing mutant LRRK2 (FIG. 15, panel (d)).

Figure 16:
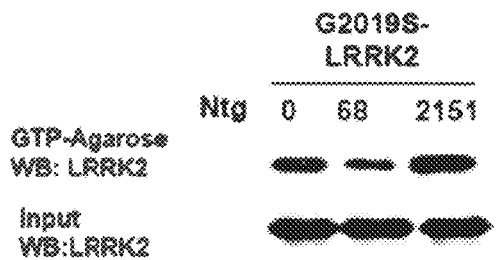
FIGS. 16 to 19 demonstrate certain aspects of a study indicating that compound 68 reduces LRRK2 GTP binding an kinase (autophosphorylation) activities in mouse brains, in which G2019S-LRRK2 BAC transgenic mice at 6-12 weeks of age were injected with vehicle, 68 (20 mg/kg), or FX2151 (20 mg/kg) intraperitoneally. The brains were dissected after 60 min injection and brain homogenates were subjected to LRRK2 GTP binding and phosphorylation assays. 68 at 20 mg/kg dose reduced brain LRRK2 GTP binding (FIGS. 16 and 17) and kinase (FIGS. 18 and 19) activities. Ntg: non-transgenic mouse.
Figure 18:
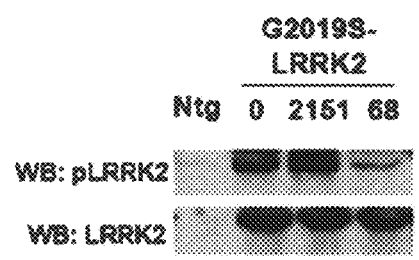
Figure 17:
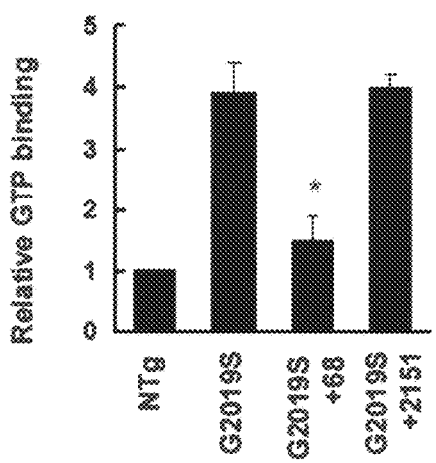
Figure 19:
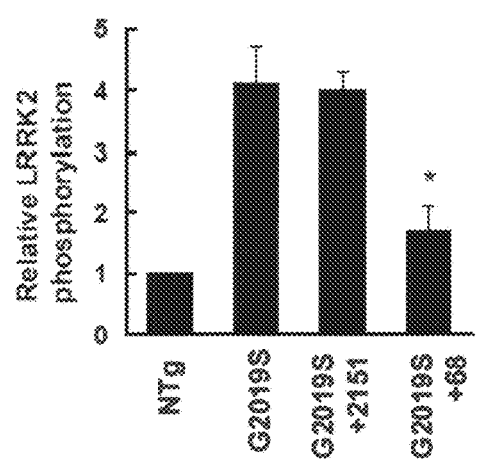

68 Attenuated LPS-Induced LRRK2 Upregulation and Microglia Activation in a Mouse Neuroinflammation Model To assess whether 70 and 68 alter LRRK2 activities in vivo, G2019S-LRRK2-BAC transgenic mice were used. 70 had poor solubility in 10% DMSO, 0.9% saline buffer and could not be dissolved at a dose of mg/kg for in vivo testing of LRRK2 functions in mice. Only the effects of 68 on LRRK2 functions were tested in vivo using G2019S-LRRK2-BAC transgenic mice. Vehicle or 68 at 10 and 20 mg/kg was injected intraperitoneally for one hour. Mouse brain homogenates were subjected to LRRK2 autophosphorylation and GTP binding assays. 68 at 10 mg/kg did not alter LRRK2 GTP binding activity in brain homogenates. However, 68 at 20 mg/kg significantly reduced LRRK2 GTP binding activity after 1 hour injection (FIGS. 16 and 17). 68 at 20 mg/kg also reduced LRRK2 phosphorylation in mouse brains after 1 hour injection (FIGS. 18 and 19). In contrast, FX2151, the ineffective analog of 68, did not alter LRRK2 kinase and GTP binding activities in mouse brains. These results indicated that 68 can penetrate BBB with higher dose at 20 mg/kg.

Figure 20:
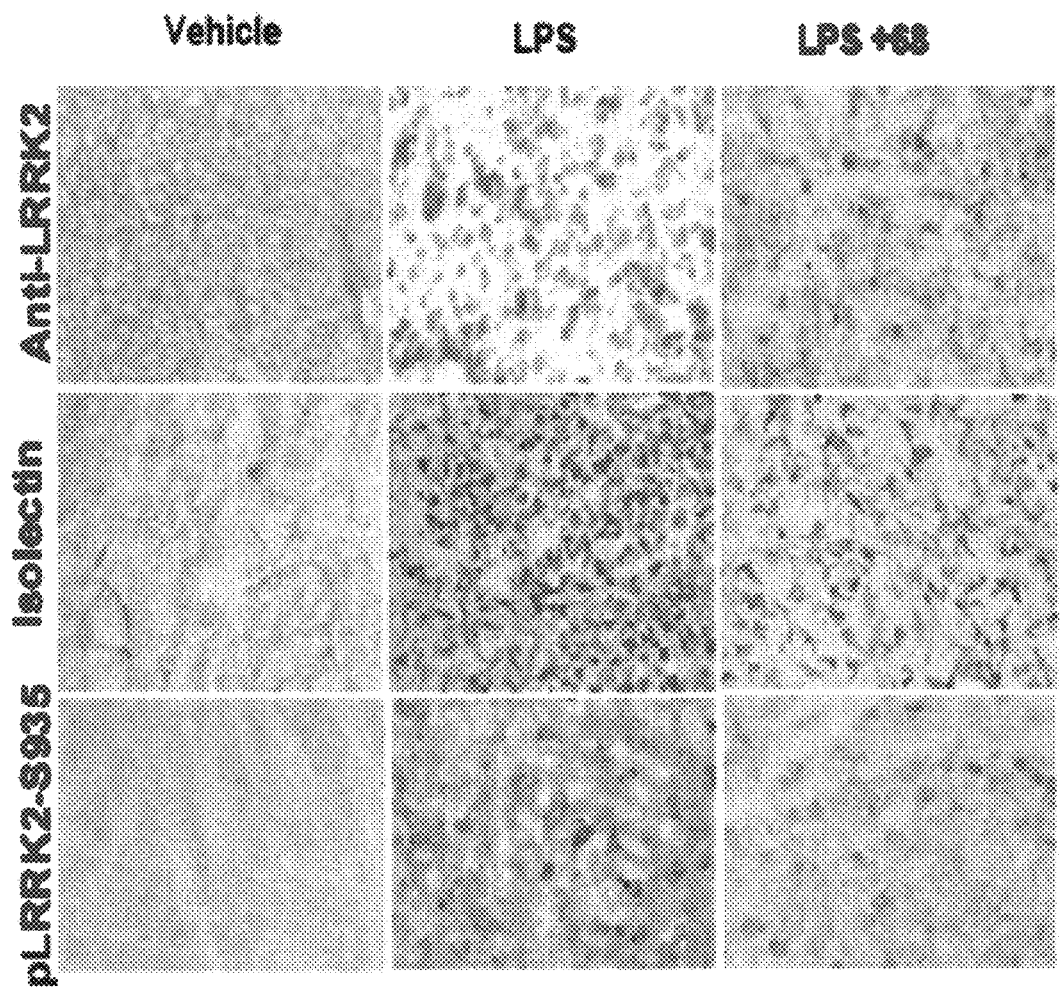
FIGS. 20 to 22 demonstrate certain aspects of a study indicating that compound 68 attenuates LPS-induced inflammation and both LRRK2 phosphorylation and expression in mice. Lipopolysaccharide (LPS) (5 µg) was injected unilaterally into the substantial nigra of G2019S-LRRK2 BAC transgenic mice at 6-12 weeks of age. 68 (20 mg/kg) was injected intraperitoneally 1 h prior to the LPS injection and then kept twice daily at the same dose for three days. Immunohistochemistry was performed on serial coronal sections through the substantial nigra.
Figure 21:
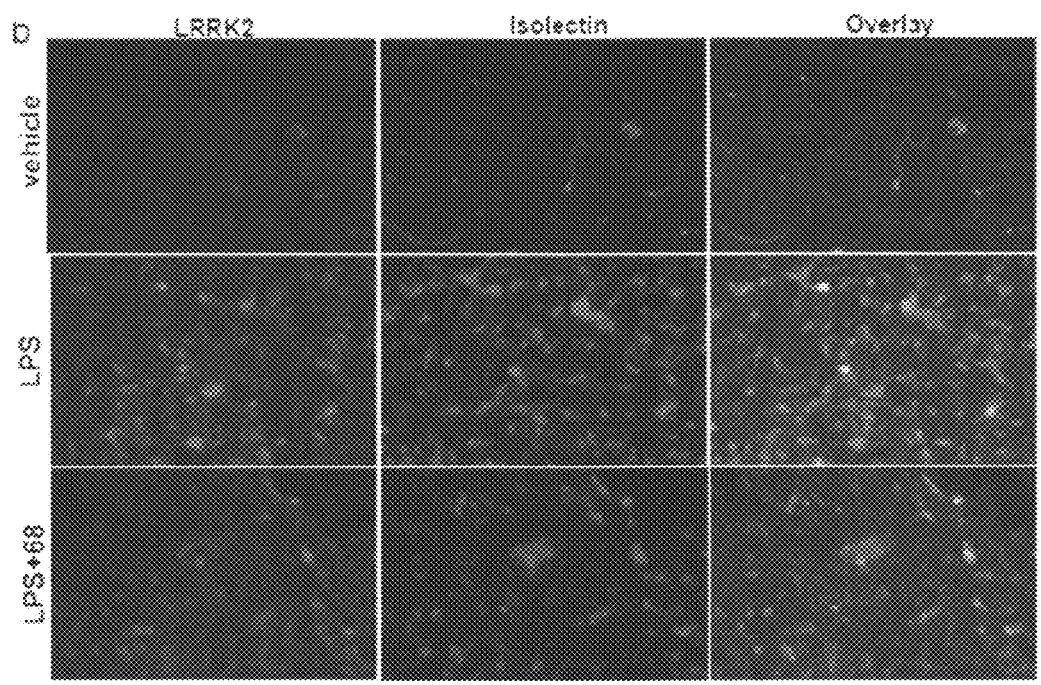
Figure 22:
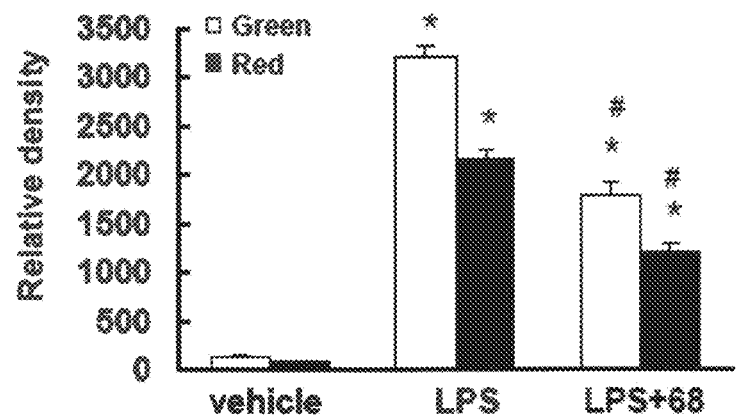

Inflammation is an important factor in PD pathogenesis. Microglial activation is one of the early indicators of degeneration and a great contributor to dopaminergic neuron degeneration. Chronic microglia-mediated inflammation likely initiates or prolongs neuron degeneration. A recent study demonstrated that LRRK2 kinase activation plays an important role in LPS-induced microglia activation in a LRRK2-BAC transgenic mouse model. Here, we employed this model to assess the in vivo effects of 68. In white matter tracts in non-injected mouse brain tissue, LRRK2 protein was undetectable, and there was a weak positive staining in the substantia nigra as described previously. Inactive microglia within the substantia nigra in mice that did not receive an LPS injection showed a weak basal level of positive immunostaining with isolectin B4 (microglia marker) antibodies (FIGS. 20-22). However, in LPS injected sites, there was robust LRRK2 and isolectin B4 positive immunostaining within the substantia nigra compared with vehicle injection groups (FIGS. 20-22). Moreover, there was also a robust anti-phosphorylated LRRK2 immunoactivity, indicating LPS induced microglia activation as well as LRRK2 expression and phosphorylation (FIGS. 20-22). Increased LRRK2 protein was predominantly located in the active microglia. Interestingly, treatment with 68 significantly reduced activated microglia numbers and densities of LPS-induced positive immunoactivity with anti-isolectin B4, anti-LRRK2, and anti-phosphorylated LRRK2 antibodies (FIGS. 20-22). In particular, the immunoreactivity of anti-phosphorylated LRRK2 antibodies in the 68 treated group was reduced up to ~54% compared with those in LPS group.

Materials and Methods

Materials and Compounds:

Media for cell culture and LipofectAMINE Plus reagent were from Invitrogen (Carlsbad, Calif.). Anti-Flag, anti-isolectin-biotin, and anti-isolectin-FICT antibodies were obtained from Sigma (St. Louis, Mo., USA). Anti-tyrosine hydroxylase (TH) was from Millipore (Billerica, Mass., USA). Anti-phospho-serine antibodies were purchased from Cell Signaling Technology (Beverly, Mass., USA). Anti-LRRK2 and some anti-phosphorylated LRRK2 antibodies were from Michael J. Fox Foundation. Anti-myc and anti-actin antibodies were from Santa Cruz (Santa Cruz, Calif., USA). Some anti-LRRK2 phosphorylation antibodies at 5935 and 52032 were kindly provided by Drs. Zhenyu Yue and Ted M. Dawson. GW5074 was purchased from BioMol.

CADD and Compounds:

CADD database screening was performed targeting the GTP domain. Briefly, CADD analysis was performed to identify putative inhibitor binding sites on the 3D structure of the ROC homodimer using the Binding Response (BR) algorithm. Docking and simulations were performed with the programs CHARMM, NAMD, and Dock 4.01 to screen an in silico database of a 1.5 million compound library. Compounds that could potentially bind LRRK2 Roc domain with physiochemical properties that maximize drug-like characteristics were selected for further validation using GTP binding assays as described below. 70 and 68 were identified from a computer-aided drug design (CADD) screen followed by an in vitro GTP binding assay validation. 70 and 68, which are not guanine analogs, were purchased from Chembridge. For in vitro biochemistry analysis and cell culture experiments, 70 and 68 were dissolved in 0.1% DMSO at final concentrations for in vitro experiments. For mouse testing, 68 was dissolved in 10% DMSO/0.9% saline and injected into mice at 20 mg/kg.

Cell Culture, LRRK2 Constructs Transfection:

Human HEK293T (human embryonic kidney) and SH-SY5Y (neuroblastoma) cells were from ATCC (Manassas, Va., USA) and grown in the media. The Flag tagged wild type, G2019S, and G2019S-K1347A constructs. Transient transfections were conducted using Lipofectamine™ and PLUS™ Reagents (Invitrogen) according to the manufacturer's protocol.

Immunoprecipitation (IP) and Western Blot Analysis:

Cell lysates or brain homogenates were subjected to immunoprecipitation (IP) using anti-FLAG-agarose (Sigma), anti-myc, and anti-LRRK2 antibodies. For Western blot analysis, the resulting immunoprecipitates and cell lysates were loaded into 4-12% NuPAGE Bis-Tris gels and transferred onto polyvinylidene difluoride membranes (Invitrogen). The membranes were probed with different antibodies, and then followed by incubation with enhanced chemiluminescence (ECL) reagents to detect proteins.

LRRK2 Autophosphorylation (Kinase) and GTP Binding Assays:

LRRK2 kinase assay was adapted from previous studies using autophosphorylation of cell lysates or brain homogenates. Briefly, HEK 293T were transiently transfected with various LRRK2 variants or kinase domain fragments for 36 h, followed by no serum starvation for 12 h, and then treated with compound 70 and 68 for 1 h. The cells were harvested using lysis buffer (Cell Signaling). Mouse brains were homogenized using RIPA buffer (Cell Signaling). The resulting cell lysates or brain homogenates were immunoprecipitated using anti-Flag antibodies. The immunoprecipitates were subjected to Western blot using anti-phosphorylation LRRK2 antibodies at S935 and S2032 residues as described previously. In some cases, immunoprecipitates were incubated with kinase reaction buffer for 90 min at 30° C. containing 50 mM $MgCl_2$, 500 μM ATP, and 10 μCi of [γ-$^{32}$P]ATP (3,000 Ci/mmol) followed by 4-12% SDS/PAGE separation and blotted onto PVDF membranes. Quantification was performed with a phosphoimager (Bio-Rad Molecular Imager FX). GTP binding assays were performed. Cell lysates or brain homogenates (100 μg protein/per reaction) were incubated with vehicle or compounds at 1-50 μM concentration for 1 h followed by addition of GTP-agarose beads (Sigma) for an additional 2 h at 4° C. The resulting beads were washed three times with cell lysis buffer, and bound protein was eluted by adding SDS-PAGE sample buffer and heating for 10 min at 72° C. Precipitates were subjected to Western blot analysis using anti-Flag antibodies.

Mouse Primary Cortical Neuronal Cultures, Transfection, and Cell Viability Assays:

Mouse primary cortical neurons were derived from CD-1 outbred mice (The Jackson Laboratory) at embryonic day 16 and cultured on 24 well plates coated with laminin- and poly-D-lysine-coated plates (BD Biosource, San Diego). Neurons were grown in neurobasal medium containing B-27 supplement, Glutamax, and penicillin/streptomycin. LRRK2 constructs were transfected into mouse primary cortical neurons using Lipofectamine 2000 (Invitrogen) according to the manufacturer's protocol. Cell viability assays were conducted. pcDNA3.1-GFP and FLAG-LRRK2 constructs at 1:15 ratio were cotransfected into SH-SY5Y cells (neurons) in 10% FBS OPTI-I media for 24 h. The media were changed to DMEM containing N2 supplement for 24 h. Cell viability was measured by counting GFP-positive viable cells (neurons) from 20 randomly selected fields using fluorescence microscopy. Viable cells (neurons) with one smooth extension (neurite) twice the length of the cell body were counted.

LPS Preinflammatory Model and Compound Treatment:

G2019S-LRRK2-BAC (Jackson, Lab. Cat: 012467) transgenic mice were food deprived for 4 h before surgery. There were 4 to 6 mice in each experimental group. Mice were anesthetized with isoflurane. LPS (5 ng containing 15,000 endotoxin units, Sigma) was injected into the substantia nigra pars compacta unilaterally with a 1 μl volume at 0.2 μl/min flow rate as described previously. The stereotaxic coordinates were −3.4 anteroposterior (AP), −1.1 ML, and −3.9 DV with respect to bregma. After injection, the needle was kept in place for 5 min before withdrawal to avoid LPS leakage up the cannula track. 68 at 20 mg/kg was injected intraperitoneally 1 hour prior to LPS injection. Then 68 was injected twice daily for three days. The mice were perfused with 4% paraformaldehyde (PFA) in PBS and the brains were dissected and frozen in isopentane and stored in a −80° C. freezer for immunostaining Animal usage was approved by the University of Maryland School of Pharmacy.

Immunohistochemical Analysis.

Mice were perfused with saline and 4% paraformaldehyde. Frozen mouse brains were sectioned through the substantia nigra at 30 μm and the sections were subjected to immunohistochemical analysis as described previously. Briefly, frozen sections were placed in 0.6% $H_2O_2$ in methanol for 10 min followed by 5% normal goat serum (Sigma) to block non-specific reactions. Sections were then sequentially incubated with primary antibodies and biotinylated anti-rabbit secondary antibodies (Vector Laboratories) and avidin-biotin-peroxidase complex (ABC Elite kit, Vector Laboratories). Anti-LRRK2 (MJFF), anti-phosphorylated LRRK2 S935 (MJFF), and anti-isolectin antibodies were used as primary antibodies. Isolectin-B4:FITC or Isolectin-B4:Biotin were from Sigma. Some tissue sections were visualized by peroxidase reaction using diaminobenzidine (DAB, Sigma). Some tissue sections were probed with Alexa Fluor 488 goat anti-mouse (rabbit) IgG and Alexa Fluor 568 goat anti-mouse (rabbit) IgG (Invitrogen) as secondary antibodies. The specificity of the immunostaining was checked by incubating adjacent sections with each preabsorbed primary antibody. The images were captured using a Zeiss 250 microscope connected with to a Zeiss Axiocam camera. The digital images were captured processed in Adobe Photoshop (v.VII). The density of red and green fluorescence in the 6 consecutive sections crossing the LPS injection site of each mouse was quantified using NIH image-J software. Six microscope field images (20×) from one brain section were subjected to fluorescence density quantification. Negative controls, omitting primary antibody, were performed and no significant staining was seen.

Data Analysis:

Quantitative data were expressed as arithmetic means±SEM based on at least three separate experiments. Statistically significant differences among groups were identified by ANOVA using Sigmastart 3.1 statistical software (Aspire Software International, VA). A p value <0.05 was considered significant.

Discussion

Two novel GTP-binding inhibitors of LRRK2, 70 and 68 (FIG. 1), were characterized to reduce kinase activity and attenuate neuronal degeneration. Although the normal function of LRRK2 is not fully understood, the elevated kinase activity in PD-linked mutations (e.g., G2019S) lead to neuronal degeneration. Thus, the inhibition of this abnormally elevated activity in the mutant LRRK2 PD cases could result in neuroprotection and represent a novel strategy for intervention. Even though the exact function of the ROC domain is unknown, our results demonstrated that reduction of the GTP binding activity inhibited LRRK2 kinase activity. To our knowledge, this study is the first report of LRRK2 GTP binding inhibitors and provides pharmacological evidence that GTP binding regulates kinase activity. These results further validate the previous genetic alteration findings and indicates that the GTP binding site in ROC domain is a drugable target.

Only a few proteins (e.g., LRRK1) in mammals are known to have intrinsic GTPase domain activity that regulates kinase domain activity. The present results show that 70 and 68 inhibited LRRK2 binding with GTP but did not alter LRRK1 GTP binding nor kinase activity, suggesting 70 and 68 are relatively specific to LRRK2. Moreover, the two inhibitors reduced the kinase activity of full length LRRK2 but did not alter the kinase activity of the LRRK2 kinase domain, further suggesting that these inhibitors reduce kinase activity via altering GTPase domain function. In vitro, 70 and 68 inhibited LRRK2 GTP binding and kinase activities in the nM range, which is similar to the effects of known LRRK2 kinase inhibitor, LRRK2-In-1. However, LRRK2-In-1 cannot penetrate the blood brain barrier (BBB), which limits its utility for PD. Our results showed that 68 inhibited LRRK2 GTP binding and kinase activities in LRRK2 transgenic mouse brains, suggesting 68 can penetrate the BBB.

One of the critical barriers to developing neuroprotective compounds for PD and other neurodegenerative diseases is that these compounds must cross the BBB to the pathologic sites. The current reported LRRK2 protein kinase inhibitors either lack specificity or do not cross the BBB. Our results showed that 68 can readily penetrate the BBB and inhibit LRRK2 GTP binding and kinase activity. Our in vitro characterization studies showed that 70 and 68 inhibited LRRK2 GTP binding at nM concentrations. However, reduction of brain LRRK2 GTP binding and kinase activities required a dose of 20 mg/kg for 68, which, at 10 mg/kg dose, did not have this effect. This suggests that 68 can penetrate the BBB but with a low brain uptake efficiency. Accordingly, these results indicate that 68 may be a lead compound for the further development into compounds that target LRRK2 functions in brain as required for PD intervention.

In LRRK2 PD cases, dopaminergic neuronal degeneration in brains results in locomotor impairment and PD symptoms. In cell culture studies, reduction of LRRK2 GTP binding by a genetic approach reduces its kinase activity, thereby suppressing neuronal degeneration. Our data showed that both 70 and 68 at nM levels significantly reduced mutant LRRK2-induced neuronal degeneration in SH-SY5Y cells and mouse primary cortical neurons. This is the first proof of principle that GTP binding inhibitors can suppress LRRK2-linked neuron degeneration.

Microglia activation often occurs in neuronal degenerative diseases, including PD, and is one of early pathological hallmarks of degeneration. Microglia-mediated inflammation triggers the vicious cycle between glial-astrocytes reaction and dopaminergic neuronal loss. Recent studies show that LRRK2 is highly expressed in macrophagic and monocytic cells, and it is expressed in the brain's immunological cells, microglia. These findings suggest a potential immunologic function for LRRK2. One report showed that pre-inflammatory stimuli (e.g., LPS) induced LRRK2 expression in peripheral blood mononuclear cells. A recent study demonstrated that inflammation increases LRRK2 activity and expression in activated microglia in a mouse model of neuroinflammation. Moreover, knockdown of LRRK2 or reduction of LRRK2 kinase activity in primary cultured microglia blocks microglial process outgrowth and TNF-alpha release, suggesting that LRRK2 may alter inflammatory responses in neurodegenerative and infectious diseases and may be involved in disease initiation or progression processes. Our data showed that treatment with 68 significantly reduced the LPS-induced microglia activation and LRRK2 expression. 68 reduced LPS-induced LRRK2 phosphorylation in activated microglia cells. Consisting with the previous report, there were no changes in anti-TH positive immunostaining between the LPS-injected side and the non-injected side, nor changes in the sham injected vehicle mouse brain tissue, suggesting that there was no dopaminergic neuron degeneration within the substantia nigra under this acute inflammation condition during our testing regimen. However, the inflammation (especially the chronic condition) triggers or accelerates dopaminergic neuronal loss. Taken together, these findings not only indicate that LRRK2 GTP binding plays a critical role in the preinflammatory response in microglia cells in brains, but also demonstrates that inhibition of LRRK2 GTP binding can attenuate the inflammation-related degenerative pathology.

In conclusion, LRRK2 GTP binding inhibitors provide a pharmacological tool to further study LRRK2 functions in PD pathogenesis. Our studies provide two lead compounds for further development into potential therapeutic agents for the treatment of PD. The present findings indicate that 70 and 68 reduced GTP binding LRRK2, thereby decreasing LRRK2 kinase activity, indicating that the GTPase domain can be employed as a novel drug target for PD.

Example 2

Development of Compound 68 Analogs

As described herein, LRRK2 has two enzymatic activities: the kinase domain and the GTPase domain, which make them a highly tractable target for therapeutic intervention. And a number of potential LRRK2 kinase inhibitors to the kinase domain were reported can prevent neuronal death, ameliorate neurodegenerative. But none are available in the clinic yet due to non-specificity or low brain penetration.

The GTPase domain of LRRK2 comprises only a small fraction (amino acids 1335-1510) of the full length protein (~7% of total); however, many of the mutations within the GTPase domain of LRRK2 including mutations of R1441 and N1437H residue that clearly segregate with PD, so this suggested that GTPase domain is tractable target for therapeutic intervention. Especially, the crystal structure of LRRK2 GTPase domain differs significantly from other small GTPases (e.g., Ras, Rho), which makes it is possible to discover potent selective inhibitors to target LRRK2 GTPase domain to avoid side effects caused by other small GTPases inhibition. For the first time, we found GTP binding inhibitor 68 (FIG. 1) can inhibit LRRK2 kinase activity, attenuate neuronal degeneration. However, 68 has moderate brain penetration ability which makes it not ideal for further developing as PD therapeutics. As described herein, rational modifications of 68 was used to obtain analogs with higher LRRK2 kinase affinity and better clinical therapeutic properties.

A challenge of neurodegenerative disorder therapeutics is still how to improve specific bioactive potency and blood-brain barrier penetration at the same time. And this challenge is the key reason that many agents failed for poor blood-brain barrier penetration, or severe side effects. In the present case, 68 ($EC_{50}$) is a powerful LRRK2 inhibitor with modest blood-brain barrier permeability, therefore, performing structural optimizing to find potent LRRK2 inhibitors with better blood-brain barrier penetration ability is important.

Since 68 significantly inhibited LRRK2 kinase activity, its basic scaffold is conserved and some substitutional groups were introduced to optimizing ability of blood-brain barrier penetration. To increase LRRK2 inhibition, the positions of those substitutional groups were changed to fit the binding site of LRRK2 GTPase domain. Compounds were designed as follows, it is predicted that those compounds, whose log P values are between about 1.0 and about 3.0 and log BB values are between about −2.0 and about 1.0, have rational blood-brain barrier penetration ability. The resulting data is set forth in Table 1 with the compound structures set forth in Table 2.

TABLE 1

Results of blood-brain barrier penetration ability prediction

| Compound No. | Log P | Log PS | Log BB |
|---|---|---|---|
| XH10102 | 1.77 | — | −0.05 |
| XH10103 | 1.44 | — | −0.20 |
| XH10104 | 1.79 | — | −0.23 |
| XH10106 | 2.84 | −1.6 | −0.20 |
| XH10107 | 2.63 | −1.6 | −0.21 |
| XH10108 | 3.21 | −1.4 | 0.14 |
| XH10110 | 2.65 | −1.7 | −0.12 |
| XH10111 | 2.06 | −1.9 | −0.06 |
| XH10112 | 3.07 | −1.4 | −0.09 |
| XH10113 | 1.38 | −2.3 | −0.19 |
| XH10114 | 1.40 | −2.4 | −0.19 |
| XH10115 | 2.45 | — | 0.04 |

TABLE 1-continued

Results of blood-brain barrier penetration ability prediction

| Compound No. | Log P | Log PS | Log BB |
|---|---|---|---|
| XH10116 | 2.26 | −1.8 | −0.06 |
| XH10117 | 2.19 | −1.8 | 0.02 |
| XH10118 | 2.06 | −1.9 | −0.06 |
| XH10119 | 1.78 | −2.1 | −0.22 |
| XH10120 | 1.70 | −2.0 | −0.19 |
| XH10121 | 2.32 | −2.5 | 0.16 |
| XH10122 | 2.65 | −1.7 | −0.12 |
| XH10126 | 3.11 | −1.3 | 0.12 |
| XH10127 | 1.70 | −2.0 | −0.27 |
| XH10128 | 1.98 | −1.9 | −0.01 |
| XH10129 | 2.10 | −1.9 | −0.22 |
| XH10130 | 1.45 | −2.6 | −0.36 |
| XH10131 | 1.81 | −1.9 | −0.30 |
| XH10132 | 2.14 | −1.9 | −0.36 |
| XH10133 | 2.27 | −1.8 | −0.26 |
| XH10134 | 2.53 | −1.6 | −0.21 |
| XH10135 | 2.23 | −2.5 | −0.14 |
| FX2143 | 1.74 | −2.0 | −0.40 |
| FX2145 | 1.04 | −3.8 | −0.78 |
| FX2147 | 1.40 | −2.4 | −0.20 |
| FX2149 | 1.38 | −2.3 | −0.21 |
| FX2151 | 1.30 | −2.3 | −0.22 |
| FX2153 | 1.63 | −2.2 | −0.35 |
| FX2155 | 1.43 | −2.3 | −0.30 |
| FX2157 | 2.54 | −1.9 | −0.51 |
| FX3067 | 1.78 | −2.1 | −0.24 |
| FX3069 | 3.05 | −1.6 | −0.06 |
| FX3071 | 3.47 | −1.5 | 0.06 |
| FX3073 | 1.60 | — | −0.43 |
| FX3075 | 2.21 | — | −0.52 |
| FX3076 | 2.69 | — | −0.55 |

The synthesis of compounds 1-42 began with 3-aminobenzoic acid derivatives (43) as shown in Scheme 1. Compound 43 was dissolved in methanol, and then $H_2SO_4$ (catalytic amount) was added, the resulting solution was heated under reflux for 12 h to synthesize the esters (44). Compounds 44 reacted with sulfonic acid chloride (45) using $Et_3N/CH_2Cl_2$ to give sulfonamides 46a-f, which were hydrolyzed to yield carboxylic acids 47a-f. Compounds 47a-f were coupled to various amino compounds using EDC.HCl and HOBt as the coupling reagents to yield inhibitors 1-42.

Scheme 1. Synthesis of sulfonamide derivatives (1-42)[a]

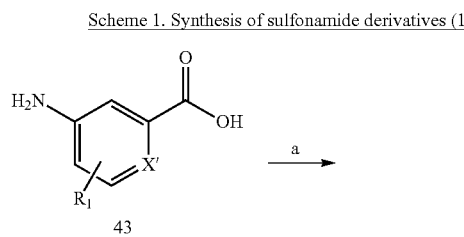

44a, $R_1$ = H, $R_2$ = $CH_2CH_3$, X' = CH;
44b, $R_1$ = H, $R_2$ = $CH_3$, X' = N;
44c, $R_1$ = 2'-F, $R_2$ = $CH_3$, X' = CH;
44d, $R_1$ = 4'-CH, $R_2$ = $CH_3$, X' = CH

46a, $R_1$ = H, $R_2$ = $CH_2CH_3$, $R_3$ = H, X' = CH, X = CH;
46b, $R_1$ = H, $R_2$ = $CH_2CH_3$, $R_3$ = 4-Cl, X' = CH, X = CH;
46c, $R_1$ = H, $R_2$ = $CH_2CH_3$, $R_3$ = $CH_3$, X' = CH, X = CH;
46d, $R_1$ = H, $R_2$ = $CH_3$, $R_3$ = H, X' = N, X = CH;
46e, $R_1$ = 6'-F, $R_2$ = $CH_3$, $R_3$ = H, X' = CH, X = CH
46e, $R_1$ = 4'-$CH_3$, $R_2$ = $CH_3$, $R_3$ = H, X' = CH, X = CH,

47a, $R_1$ = H, $R_3$ = H, X' = CH, X = CH;
47b, $R_1$ = H, $R_3$ = 4-Cl, X' = CH, X = CH;
47c, $R_1$ = H, $R_3$ = $CH_3$, X' = CH, X = CH;
47d, $R_1$ = H, $R_3$ = H, X' = N, X = CH;
47e, $R_1$ = 6'-F, $R_3$ = H, X' = CH, X = CH
47f, $R_1$ = 4'-$CH_3$, $R_3$ = H, X' = CH, X = CH, 1-42

[a]Reagents and conditions: (a) MeOH, $H_2SO_4$, reflux, 10 h; (b) $Et_3N$, $CH_2Cl_2$, rt, 24 h; (c) 1N NaOH, MeOH (v/v=1:1), rt, 24 h; (d) R3-$NH_2$, EDC.HCl, HOBt, DMF, 40° C., 24 h.

TABLE 2

Structure of Inhibitors 1-42.

| No. | Structure | X' | $R_1$ | $R_4$ |
|---|---|---|---|---|
| XH10102 1 | | CH | H | —$NHCH_2CH_2N(CH_3)_2$ |

TABLE 2-continued

Structure of Inhibitors 1-42.

| No. | Structure | X' | R₁ | R₄ |
|---|---|---|---|---|
| XH10103 2 | | CH | H | piperazine-N-CH₃ |
| XH10104 3 | | CH | H | piperazine-N-CH₂CH₃ |
| XH1062 = XH10115 4 | | CH | 6'-F | —NHCH₂CH₂CH₃ |
| XH1063 XH10116 5 | | CH | 6'-F | —NHCH₂CH₂OCH₃ |
| XH10117 6 | | CH | 6'-F | piperazine-N-CH₂CH₃ |
| XH10120 7 | | CH | 6'-F | piperazine-N-CH₃ |
| XH10113 8 | | N | H | —NHCH₂CH₂CH₃ |
| XH10114 9 | | N | H | —NHCH₂CH₂OCH₃ |
| XH10119 10 | | N | H | —NHCH₂CH₂CH₃ |
| XH10121 11 | | CH | 4'-CH₃ | —NHCH₂CH₂CH₃ |
| XH10122 12 | | CH | 4'-CH₃ | —NHCH₂CH₂OCH₃ |
| XH10118 13 | | CH | 4'-CH₃ | piperazine-N-CH₂CH₃ |
| XH10105 14 | 4-Cl-C₆H₄-SO₂-NH-[pyridine(X')-R₁]-C(O)-R₄ | CH | H | —NHCH₂CH₂N(CH₃)₂ |
| XH10106 15 | | CH | H | —NHCH₂CH₂OCH₃ |
| XH10107 16 | | CH | H | piperazine-N-CH₂CH₃ |
| XH10108 17 | | CH | H | —NHCH₂CH₂CH₃ |
| XH10110 18 | 4-CH₃-C₆H₄-SO₂-NH-[pyridine(X')-R₁]-C(O)-R₄ | CH | H | —NHCH₂CH₂OCH₃ |

TABLE 2-continued
Structure of Inhibitors 1-42.
| No. | Structure | X' | R₁ | R₄ |
|---|---|---|---|---|
| XH10111 19 | | CH | H |  |
| XH10112 20 | | CH | H | —NHCH₂CH₂CH₃ |
| H10127 21 | 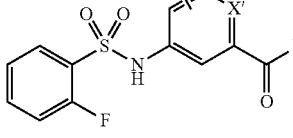 | CH | H |  |
| XH10128 22 | | CH | H |  |
| XH10129 23 | | CH | H | —NHCH₂CH₂OCH₃ |
| XH10130 24 | | N | H | —NHCH₂CH₂OCH₃ |
| XH10131 25 | | CH | 6'-F |  |
| XH10132 26 | | CH | 6'-F | 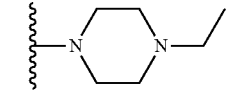 |
| XH10133 27 | | CH | 6'-F | —NHCH₂CH₂OCH₃ |
| XH10134 28 | | CH | 6'-F | —NHCH₂CH₂CH₃ |
| XH10135 29 | | CH | 6'-F | —NHCH₂CH₂N(CH₃)₂ |
| XH10126 30 | | CH | 6'-F | —OCH₂CH₃ |
| | 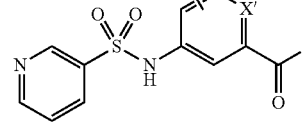 | | | |
| 31 | 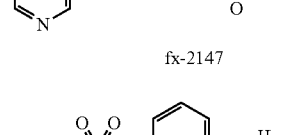 fx-2147 | H | CH | NHCH2CH2OCH3 |
| 32 |  fx-2149 | H | CH | —NHCH₂CH₂CH₃ |

TABLE 2-continued

Structure of Inhibitors 1-42.

| No. | Structure | X' | R₁ | R₄ |
|-----|-----------|----|----|----|
| 33 | fx-2151 | H | CH | —NHCH(CH₃)₂ |
| 34 | fx-2153 | H | CH | —NHCH₂CH(CH₃)₂ |
| 35 | fx-2155 | H | CH | HN-cyclopropyl |
| 36 | fx-2157 | H | CH | HN-CH₂-C₆H₄-OCH₃ |
| 37 | FX-3067 | H | CH | —NHCH₂CH₂CH₂CH₃ |
| 38 | FX-3069 | H | CH | —NH(CH₂)₄CH₃ |
| 39 | FX-3071 | H | CH | —NH(CH₂)₅CH₃ |

TABLE 2-continued

Structure of Inhibitors 1-42.

| No. | Structure | X' | R$_1$ | R$_4$ |
|---|---|---|---|---|
| 40 | FX-3073 | H | CH | ⌇NH-CH$_2$-cyclopropyl |
| 41 | fx-2175 | H | CH | —NHCH$_2$CH$_2$CF$_3$ |
| 42 | fx-2176 | H | CH | —NHCH$_2$CF$_2$CF$_3$ |

Experimental Section

General Information

Melting points were determined on a Thomas Hoover Unimelt melting point apparatus model 6406-K and are uncorrected. $^1$H NMR spectroscopies were recorded on a VARIAN 400 MHz spectrometer in CDCl$_3$, DMSO-d$_6$, or acetone-d$_6$. The chemical shifts are reported in parts per million (ppm) relative to tetramethylsilane (TMS). $^{13}$C NMR spectroscopies were performed on a VARIAN 400-MHz at 100 MHz. ESI mass spectra were obtained on a Finnigan 4000 spectrometer. Column chromatography was performed on silica gel (Merck, grade 60, 240-400 mesh, 100 Å) from Aldrich Chemical Co. Thin-layer chromatography (TLC) was carried out on Analtech 250-mm silica gel GHLF Uniplates. Visualization was obtained with UV.

General Procedure for the Synthesis of 1-42:

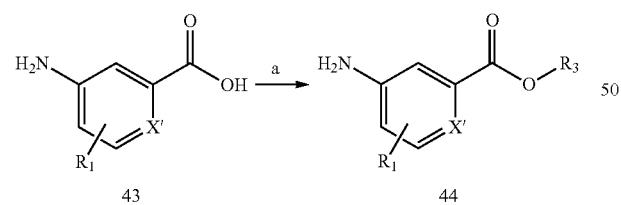

General synthetic procedure of 44: Starting material 43 (1.0 mmol) dissolved in 15 mL methanol, stirred, then 0.2 mL concentrated sulfuric acid was added dropwise. The resulting solution was refluxed gently with stirring for 12 h. And then cooled to room temperature, saturated NaHCO3 solution was added dropwise to adjust pH value to 8.0. After removing methanol, the residue dissolved in ethyl acetate 50 mL, washed with water (15 mL×3) and saturated NaHCO3 solution (15 mL×3) respectively. The organic extraction was dried (Na$_2$SO$_4$) and concentrated to get ester (44) without further purification.

Methyl 4-aminopyridine-2-carboxylate 44b (XH1091)

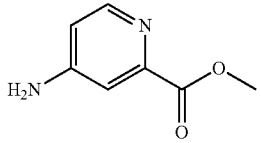

XH1091

Following the general synthetic procedure of 44, 4-aminopyridine-2-carboxylic acid reacted with methanol to get methyl 4-aminopyridine-2-carboxylate (44b), Yield 76.4%. $^1$H NMR (400 MHz, CDCl$_3$) δ 8.60 (s, 1H), 8.25 (s, 1H), 7.57 (s, 1H), 3.99 (br s, 2H), 3.92 (s, 3H). $^{13}$C NMR (100 MHz, CDCl$_3$) δ 166.0, 142.5, 140.5, 140.3, 126.3, 121.9, 52.4.

Methyl 5-amino-2-fluorobenzoate 44c (XH1092)

XH1092

Following the general synthetic procedure of 44, 5-amino-2-fluorobenzoic acid reacted with methanol to get methyl 5-amino-2-fluorobenzoate (44c), yield 93.1%. $^1$H NMR (400 MHz, CDCl$_3$) δ 7.19 (s, 1H), 6.92 (m, 1H), 6.79 (s, 1H), 3.89 (s, 3H), 3.66 (br s, 2H). $^{13}$C NMR (100 MHz, CDCl$_3$) δ 165.0, 156.5&154.0, 142.3, 120.6&120.7, 118.4-118.5, 117.4 & 117.6, 117.1, 52.7.

Methyl 3-amino-4-methyl benzoate 44d (XH1090)

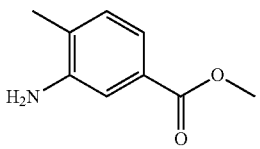

Following the general synthetic procedure of 44, 3-amino-4-methylbenzoic acid reacted with methanol to get methyl 3-amino-4-methyl benzoate, yield 80.0%. $^1$H NMR (400 MHz, CDCl$_3$) δ 7.39 (s, 2H), 7.11 (s, 1H), 4.05 (br s, 2H), 3.88 (s, 3H), 2.23 (s, 3H); $^{13}$C NMR (100 MHz, CDCl$_3$) δ 167.3, 143.9, 130.4, 128.9, 128.0, 120.3, 115.9, 51.9, 17.6.

General Synthetic Procedure of 46:

The ester 44 (3.83 mmol) prepared by last step (or commercial available) was dissolved in THF (20 mL), and then sulfonic acid chloride 45 (3.83 mmol) and triethylamine (4.95 mmol) were added. Stirred at room temperature overnight. The resulting solution was concentrated in vacuo and extracted with ethyl acetate (25 mL×3). The combined extractions were washed with water (20 mL×3) and saturated NaCl solution (20 mL×3) respectively, and then dried (Na$_2$SO$_4$). The solvent was removed by rotary evaporation, and the resulting material was purified by column chromatography (EtOAc/hexanes, 1:6-1:1) to yield 46a-f.

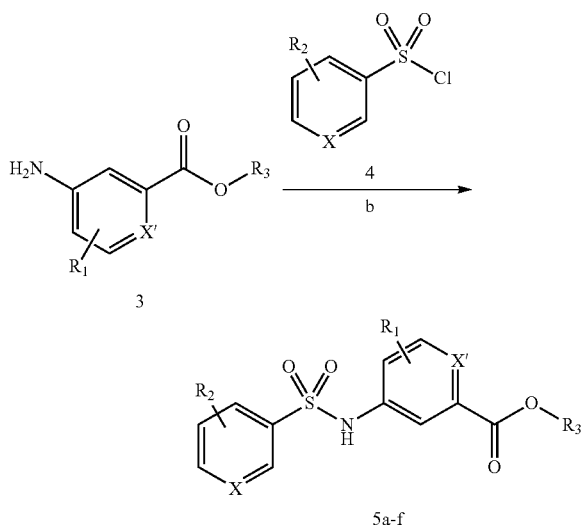

Ethyl 3-(N-benzenesulfonyl)-amino benzoate 46a (XH1093)

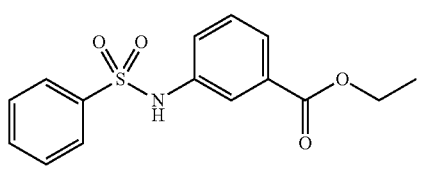

Following the general synthetic procedure of 46, ethyl 3-aminobenzoate (3a, sigma) reacted with benzenesulfonyl chloride to give 46a, yield 83.3%. $^1$H NMR (400 MHz, CDCl$_3$) δ 7.77-7.71 (m, 4H), 7.50 (s, 1H), 7.41-7.31 (m, 5H), 4.35 (s, 2H), 1.34 (s, 3H). $^{13}$C NMR (100 MHz, CDCl$_3$) δ 166.0, 138.8, 136.9, 133.1, 131.5, 129.4, 129.1 (2C), 127.2 (2C), 126.1, 125.3, 122.2, 61.4, 14.2.

Ethyl 3-[N-(4-chloro-benzenesulfonyl)]-amino benzoate 46b (XH1094)

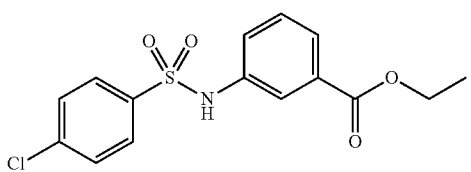

C$_{15}$H$_{14}$ClNO$_4$S
Mol. Wt.: 339.8

Following the general synthetic procedure of 46, ethyl 3-aminobenzoate (3a, sigma) reacted with 4-chloro benzenesulfonyl chloride to give 46b, yield 72.8%. $^1$H NMR (400 MHz, CDCl$_3$) δ 7.82-7.68 (m, 5H), 7.46 (s, 1H), 7.42-7.30 (m, 3H). $^{13}$C NMR (100 MHz, CDCl$_3$) δ 166.1, 139.7, 137.3, 136.7, 131.6, 129.6, 129.4 (2C), 128.6 (2C), 126.3, 125.4, 122.3, 61.6, 14.2.

Ethyl 3-[N-(4-methyl-benzenesulfonyl)]-amino benzoate 46c (XH1095)

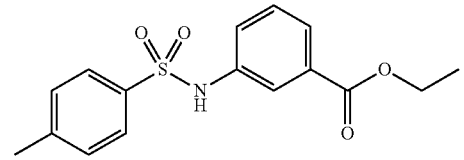

Following the general synthetic procedure of 46, ethyl 3-aminobenzoate reacted with 4-methyl benzenesulfonyl chloride to give 46c, yield 77.9%. $^1$H NMR (400 MHz, CDCl$_3$) δ 7.72 (s, 2H), 7.66 (s, 2H), 7.40 (s, 2H), 7.30 (m, 1H), 7.19 (s, 1H), 4.34 (s, 2H), 2.34 (s, 3H), 1.34 (s, 3H). $^{13}$C NMR (100 MHz, CDCl$_3$) δ 166.1, 144.1, 137.1, 135.8, 131.5, 129.7 (2C), 129.4, 127.3 (2C), 125.9, 125.1, 121.9, 61.4, 21.5, 14.2.

Methyl 3-(N-benzenesulfonyl)-amino-4-methyl benzoate 46d (XH1096-2-spot2)

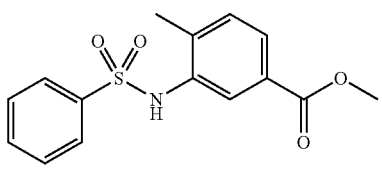

Following the general synthetic procedure of 46, methyl 3-amino-4-methylbenzoate (3b) reacted with benzenesulfonyl chloride to give 46d, yield 37.1%. ¹H NMR (400 MHz, DMSO-d6) δ 9.82 (s, 1H), 7.68-7.61 (m, 5H), 7.57-7.53 (m, 2H), 7.28-7.26 (d, J=8.0 Hz, 1H), 3.79 (s, 2H), 2.01 (s, 3H). ¹³C NMR (100 MHz, DMSO-d6) δ 166.0, 140.6, 140.3, 135.6, 133.4, 131.6, 139.7 (2C), 128.4, 127.5, 127.4, 126.9 (2C), 52.5, 18.1.

Methyl 3-(N,N-dibenzenesulfonyl)-amino-4-methyl benzoate XH1096-1-spot1

XH1096-SPOT1

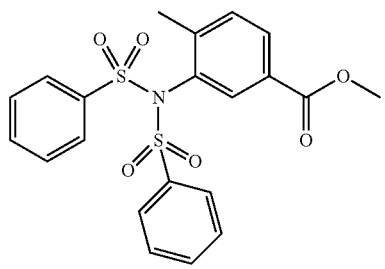

Following the general synthetic procedure of 46, methyl 3-amino-4-methylbenzoate reacted with benzenesulfonyl chloride to give XH1096-1-spot1, yield 22.0%. ¹H NMR (400 MHz, DMSO-d6) δ 7.98-7.96 (d, J=8.0 Hz, 1H), 7.88-7.84 (t, J=0.72 Hz, 2H), 7.80-7.79 (m, 4H), 7.72-7.68 (m, 4H), 7.52-7.50 (d, J=8.0 Hz, 1H), 7.30 (s, 1H), 3.81 (s, 3H), 1.96 (s, 3H).

Methyl 4-(N,N-dibenzenesulfonyl)-aminopyridine-2-carboxylate XH1097 (disulfate acyl)

XH1097

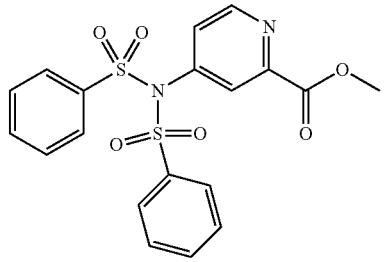

Following the general synthetic procedure of 46, methyl 4-aminopyridine-2-carboxylate reacted with benzenesulfonyl chloride to give XH1097, yield 50.1%. ¹H NMR (400 MHz, DMSO-d6) δ 9.20 (s, 1H), 8.48 (d, J=2.4 Hz, 1H), 7.89-7.81 (m, 7H), 7.73-7.69 (m, 4H), 3.89 (s, 3H). ¹³C NMR (100 MHz, DMSO-d6) δ 164.3, 155.5, 151.8, 139.1, 137.9, 135.7, 135.7, 131.0, 130.3, 128.6, 127.0, 53.3.

Methyl 3-(N-4-fluorobenzenesulfonyl)-aminobenzoate XH10124

C₁₅H₁₄FNO₄S
Mol. Wt.: 323.3

XH10124-SPOT1

Following the general synthetic procedure of 46, ethyl 3-aminobenzoate reacted with 2-fluorobenzenesulfonyl chloride to give XH10124-spot1, yield 74.3%. ¹H NMR (400 MHz, CDCl₃) δ 7.89-7.83 (m, 2H), 7.77-7.75 (d, J=7.6 Hz, 1H), 7.70 (s, 1H), 7.55-7.48 (m, 1H), 7.47-7.45 (d, J=8.0 Hz, 1H), 7.33-7.29 (t, J=8.0 Hz, 1H), 7.22-7.12 (m, 2H), 4.40-4.35 (q, J=7.2 Hz, 2H), 1.35-1.38 (t, J=7.2 Hz, 3H). ¹³C NMR (100 MHz, CDCl₃) δ 166.0, 160.0 & 157.4 (1C), 136.5, 135.6 & 135.5 (1C), 131.6, 130.9, 129.4, 126.6 & 126.7 (1C), 126.2, 124.8, 124.5, 121.8, 116.9&117.1 (1C), 61.5, 14.2.

Methyl 3-[N,N-di-(4-fluorobenzenesulfonyl)]-aminobenzoate XH10124-spot2

XH10124-SPOT2

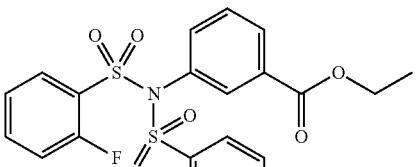

C₂₁H₁₇F₂NO₆S₂
Mol. Wt.: 481.5

Following the general synthetic procedure of 46, ethyl 3-aminobenzoate reacted with 2-fluorobenzenesulfonyl chloride to give XH10124-spot2, yield 8.3%. ¹H NMR (400 MHz, CDCl₃) δ 8.16-8.14 (d, J=6.8 Hz, 1H), 8.01-7.97 (m, 2H), 7.93 (s, 1H), 7.70-7.66 (m, 2H), 7.54-7.47 (m, 2H), 7.34-7.30 (t, J=8.0 Hz, 2H), 7.19-7.23 (m, 2H), 4.40-4.34 (q, J=7.2 Hz, 2H), 1.36-1.40 (t, J=7.2 Hz, 3H). ¹³C NMR (100 MHz, CDCl₃) δ 165.3, 160.5, 157.8, 137.1, 137.0, 136.3, 133.4, 132.3, 132.0, 131.7, 129.4, 126.8, 126.7, 123.7, 117.6, 117.4, 61.5, 14.4.

Methyl 4-[N,N-di-(2-fluorobenzenesulfonyl)]-amin-opyridine-2-carboxylate XH10125

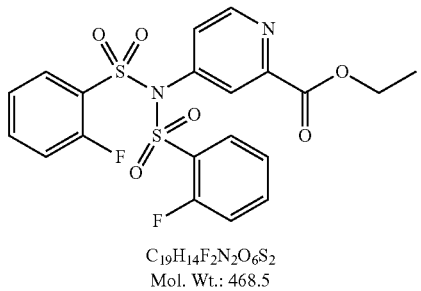

XH10125-SPOT1

C₁₉H₁₄F₂N₂O₆S₂
Mol. Wt.: 468.5

Following the general synthetic procedure of 46, methyl 4-aminopyridine-2-carboxylate reacted with 2-fluoro-benzenesulfonyl chloride to give XH10125. yield % ¹H NMR (400 MHz, CDCl₃) δ 9.27 (s, 1H), 8.65 (s, 1H), 8.31 (s, 1H), 7.97-8.00 (m, 2H), 7.66-7.72 (m, 2H), 7.32-7.36 (m, 2H), 7.19-7.23 (m, 2H), 3.96 (s, 3H). ¹³C NMR (100 MHz, CDCl₃) δ 164.6, 160.3, 157.7, 155.6, 152.0, 140.1, 137.5, 137.4, 132.2, 130.6, 126.8, 126.4, 124.9, 117.7, 117.5, 52.9.
XH10126
¹H NMR (400 MHz, CDCl₃) δ 7.82-7.76 (m, 1H), 7.70-7.68 (m, 1H), 7.56-7.50 (m, 2H), 7.41-7.39 (m, 1H), 7.21-7.13-(m, 2H), 7.02-6.98 (t, J=9.6 Hz, 1H), 3.90 (s, 3H). ¹³C NMR (100 MHz, CDCl₃) δ 168.6, 164.9&162.4, 164.1&161.6, 139.9&140.0 (1C), 136.3, 135.0, 132.0, 130.5&130.6 (1C), 129.3, 128.9, 123.2&123.3 (1C), 122.2&122.4 (1C), 121.1&121.3 (1C), 57.0.

General Synthetic Procedure of 47:

Compound 46 (3.0 mmol) was dissolved in mixture of THF (5 mL) and MeOH (10 mL), and then 1N NaOH (10 mL) was added, stirred overnight. After removing most of THF and MeOH, the resulting solution was adjusted pH value to 2.0 using 6N HCl. The precipitate was filtered and dried to give 47.

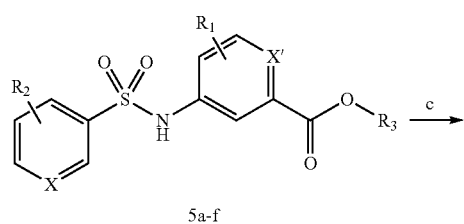

3-(N-benzenesulfonyl)-amino-4-methylbenzoic acid 47a (XH1099)

Following the general synthetic procedure of 47, 46a hydrolyzed under the condition of 1N NaOH existed to obtain 47a, yield 98.2%. ¹H NMR (400 MHz, DMSO-d6) δ 13.05 (br s, 1H), 10.56 (br s, 1H), 7.77 (s, 2H), 7.71 (s, 1H), 7.60-7.56 (m, 4H), 7.36 (s, 2H). ¹³C NMR (100 MHz, DMSO-d6) δ 167.1, 139.7, 138.4, 133.5, 132.2, 129.9, 129.7 (2C), 127.0 (2C), 125.3, 124.5, 120.9.

3-[N-(4-chloro-benzenesulfonyl)]-aminobenzoic acid 47b (XH10100)

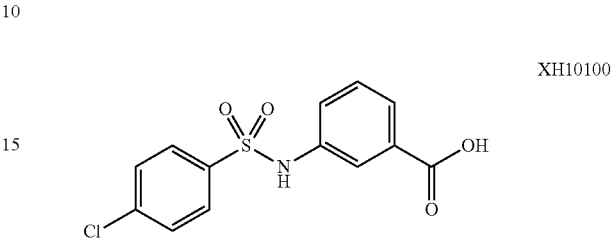

XH10100

Following the general synthetic procedure of 47, 46b hydrolyzed under the condition of 1N NaOH existed to obtain 47b, yield 94.7%. ¹H NMR (400 MHz, DMSO-d6) δ 13.0 (br s, 1H), 10.67 (br s, 1H), 7.80-7.58 (m, 5H), 7.42-7.30 (m, 2H). ¹³C NMR (100 MHz, DMSO-d6) δ 167.1, 138.4, 138.1, 132.2, 130.0, 129.9 (2C), 128.9 (2C), 125.6, 124.8, 121.2.

3-[N-(4-methyl-benzenesulfonyl)]-aminobenzoic acid 47c (XH10101)

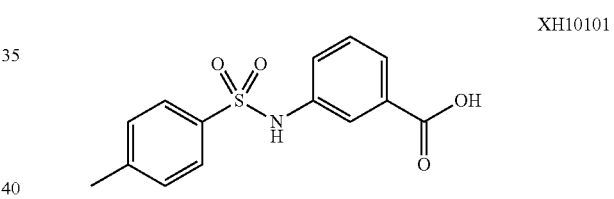

XH10101

Following the general synthetic procedure of 47, 46c hydrolyzed under the condition of 1N NaOH existed to obtain 47c, yield 94.4%. ¹H NMR (400 MHz, DMSO-d6) δ 13.0 (br s, 1H), 10.47 (br s, 1H), 7.75-7.54 (m, 4H), 7.40-7.30 (m, 4H), 2.32 (s, 3H). ¹³C NMR (100 MHz, DMSO-d6) δ 167.2, 143.9, 138.6, 136.8, 132.1, 130.2 (2C), 129.9, 127.1 (2C), 125.1, 124.3, 120.7, 21.3.

3-(N-benzenesulfonyl)-amino-4-methylbenzoic acid 47d (XH1096-2spot Hydro)

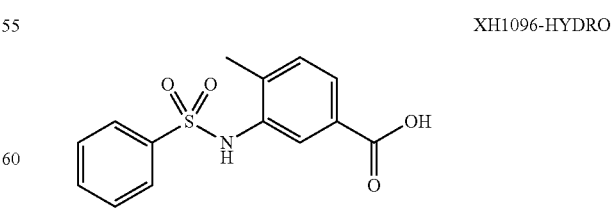

XH1096-HYDRO

Following the general synthetic procedure of 47, 46d hydrolyzed under the condition of 1N NaOH existed to obtain 47d, yield 68.0%. ¹H NMR (400 MHz, DMSO-d6-d6) δ 12.91 (br s, 1H), 9.76 (s, 1H), 7.68-7.62 (m, 4H), 7.57-7.53 (m, 3H), 7.26-7.24 (d, J=8.0 Hz, 1H), 2.02 (s, 3H). $^{13}$C NMR (100 MHz, DMSO-d6) δ 167.1, 140.6, 139.9, 135.4, 133.3, 131.4, 129.7 (2C), 129.5, 127.7, 127.6, 126.9 (2C), 18.2.

4-(N-benzenesulfonyl)-aminopyridine-2-carboxylic acid 47e (XH1097-hydrolysis)

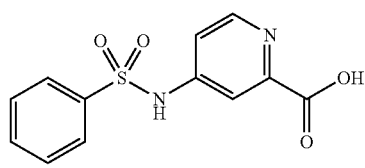

XH1097-HYDRO $C_{12}H_{10}N_2O_4S$
Mol. Wt.: 278.3

Following the general synthetic procedure of 47, 46e hydrolyzed under the condition of 1N NaOH existed to obtain 47e, yield 71.2%. $^1$H NMR (400 MHz, DMSO-d6) δ 10.9 (s, 1H), 8.72 (s, 1H), 8.50 (d, J=2.0 Hz, 1H), 7.96 (s, 1H), 7.79 (s, 1H), 7.77 (s, 1H), 7.62-7.64 (m, 1H), 7.55-7.59 (m, 3H). $^{13}$C NMR (100 MHz, DMSO-d6) δ 166.0, 145.9, 145.1, 139.2, 135.2, 133.9, 129.9 (2C), 127.8, 127.3, 127.1 (2C).

5-(N-benzenesulfonyl)-amino-2-fluorobenzoic acid 47f (XH1098-hydrolysis, two step together)

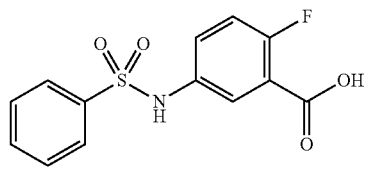

XH1098-HYDRO

Following the general synthetic procedure of 47, 46f hydrolyzed under the condition of 1N NaOH existed to obtain 47f yield 41.1%. $^1$H NMR (400 MHz, DMSO-d6) δ 13.36 (br s, 1H), 10.44 (s, 1H), 7.73-7.71 (m, 2H), 7.63-7.53 (m, 4H), 7.32-7.30 (m, 1H), 7.23-7.18 (t, J=9.2 Hz, 1H). $^{13}$C NMR (100 MHz, DMSO-d6) δ 164.8, 159.6-157.1, 139.3, 134.1, 133.6, 129.7 (2C), 127.2, 127.0 (2C), 123.9, 120.1 &119.9, 118.5 & 118.2.

Xh10124-spot1-hydro
$^1$H NMR (400 MHz, DMSO-d6-D$_2$O) δ 7.74-7.78 (t, J=7.6 Hz, 1H), 7.64 (s, 1H), 7.8-7.61 (m, 1H), 7.54-7.56 (d, J=7.2 Hz, 1H), 7.27-7.34 (m, 4H). $^{13}$C NMR (100 MHz, DMSO-d6) δ 163.0, 155.5& 153.0, 133.4, 132.6, 127.7, 126.6, 126.0, 122.6, 121.5 &121.3, 120.3, 116.4, 133.6 &113.4.

XH10125-spot1-hydro
$^1$H NMR (400 MHz, DMSO-d6+D$_2$O) δ 8.73 (s, 1H), 8.51 (s, 1H), 8.02 (s, 1H), 7.83-7.87 (m, 1H), 7.69-7.71 (m, 1H), 7.37-7.41 (m, 2H). $^{13}$C NMR (100 MHz, DMSO-d6) δ 165.8, 159.7&157.1 (1C), 145.7, 144.5, 137.2, 134.5, 130.6, 127.9, 127.3, 126.5 & 126.3 (1C), 125.8, 118.0 & 117.8 (1C).

XH10125-spot2-hydro
$^1$H NMR (400 MHz, DMSO-d6) δ 8.69-8.67 (d, J=1.6 Hz, 1H), 8.50-8.49 (d, J=2.4 Hz, 1H), 7.95-7.93 (m, 1H), 7.87-7.82 (m, 1H), 7.69-7.68 (m, 1H), 7.43-7.34 (m, 2H), XH10126-hydro
$^1$H NMR (400 MHz, DMSO-d6) δ 13.40 (br s, 1H), 10.80 (s, 1H), 7.81-7.78 (m, 1H), 7.72-7.67 (m, 1H), 7.60-7.58 (m, 1H), 7.45-7.40 (t, J=9.6 Hz, 1H), 7.38-7.32 (m, 2H), 7.24-7.20 (m, 1H), $^{13}$C NMR (100 MHz, DMSO-d6) δ 160.8, 153.1, 155.7, 132.7, 129.7, 126.8, 122.7, 121.6, 119.6, 116.1, 114.3, 113.8, General Synthetic Procedure of 1-42:

To a solution of 6a-f (0.5 mmol) in DMF (5 mL), H$_2$N—R4 (0.5 mmol) was added. And then EDC.HCl (0.6 mmol) and HOBt were added equivalently. The resulting solution stayed at room temperature for 24 h. After removing DMF in vacuum, the residue was purified by column chromatography (EtOAc/hexanes, 1:4-1:1) to obtain 1-42.

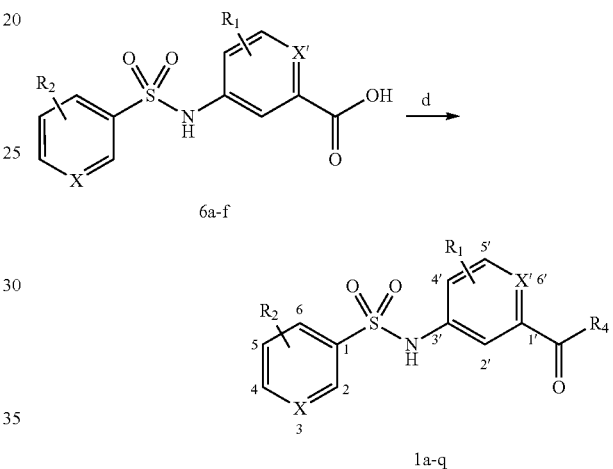

N-propyl-5-[(N-benzenesulfonyl)-amino]-2-fluorobenzamide 1a (XH10115)

XH10115

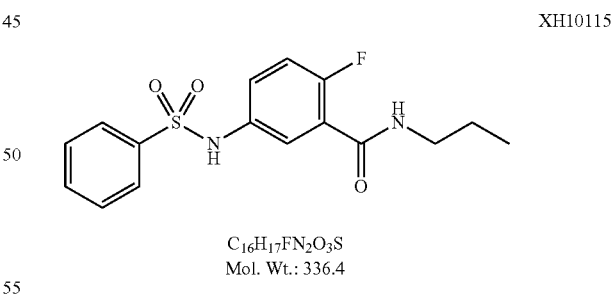

$C_{16}H_{17}FN_2O_3S$
Mol. Wt.: 336.4

Following general synthetic procedure of 1-42, 5-(N-benzenesulfonyl)-amino-2-fluorobenzoic acid reacted with propylamine to give the titled compound, yield 78.8%. $^1$H NMR (400 MHz, Acetone-d6) δ 9.00 (br s, 1H), 7.75-7.73 (d, J=6.8 Hz, 2H), 7.61-7.57 (m, 1H), 7.57-7.55 (d, J=8.0 Hz, 1H), 7.50-7.47 (t, J=8.0 Hz, 2H), 7.39 (br s, 1H), 7.34-7.30 (m, 1H), 7.10-7.05 (m, 1H), 3.31-3.26 (q, J=13.2 Hz, 2H), 1.57-1.52 (m, 2H), 0.89-0.86 (t, J=8.0 Hz, 3H). $^{13}$C NMR (100 MHz, DMSO-d6) δ 163.6, 157.5& 155.0 (1C), 139.1, 133.9, 133.7, 129.8 (2C), 127.0 (2C), 124.8 & 124.6 (1C), 122.3, 117.5 & 117.3 (1C), 41.3, 22.4, 11.6.

N-(2-methoxyl-ethyl)-5-[(N-benzenesulfonyl)-amino]-2-fluorobenzamide 2 (XH10116)

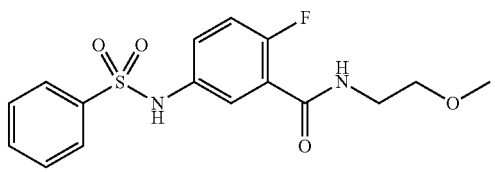

C$_{16}$H$_{17}$FN$_2$O$_4$S
Mol. Wt.: 352.4

Following general synthetic procedure of 1-42, 5-(N-benzenesulfonyl)-amino-2-fluorobenzoic acid reacted with 2-methoxylethylamine to give 1b, yield 96.2%. $^1$H NMR (400 MHz, CDCl$_3$) δ 9.11 (s, 1H), 7.97-7.94 (m, 1H), 7.76-7.74 (d, J=8.0 Hz, 2H), 7.47-7.45 (t, J=6.8 Hz, 1H), 7.38-7.30 (m, 3H), 7.08-7.03 (m, 1H), 3.83-3.79 (m, 2H), 3.61-3.58 (m, 2H), 3.38 (s, 1H). $^{13}$C NMR (100 MHz, CDCl$_3$) δ 163.0 & 162.9 (1C), 158.8 & 156.4 (1C), 139.1, 134.6, 132.7, 129.0 (2C), 127.0 (2C), 125.7&125.6 (1C), 124.4, 120.6 & 120.5 (1C), 117.1 & 116.9 (1C), 70.8, 58.8, 40.1.

N-[2-(N,N-dimethylamino)-ethyl]-3-[(N-benzenesulfonyl)-amino]-benzamide (1c, XH10102)

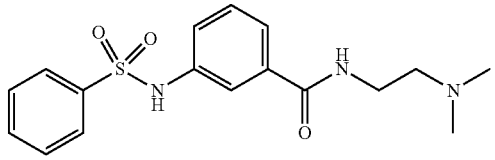

C$_{17}$H$_{21}$N$_3$O$_3$S
Mol. Wt.: 347.4

XH10102

Following general synthetic procedure of 1-42, 3-(N-benzenesulfonyl)-amino-benzoic acid reacted with N1,N1-dimethylethane-1,2-diamine to give 1c, yield 42.8%. $^1$H NMR (400 MHz, CDCl$_3$) δ 8.94 (br s, 2H), 7.98 (m, 1H), 7.80-7.75 (m, 3H), 7.53-7.47 (m, 2H), 7.44-7.40 (m, 1H), 7.34-7.30 (m, 2H), 7.26-7.24 (m, 1H), 3.71-3.70 (t, J=5.6 Hz, 2H), 2.82-2.81 (t, J=5.6 Hz, 2H), 2.45 (s, 6H). $^{13}$C NMR (100 MHz, CDCl$_3$) δ 167.1, 139.4, 138.2, 134.7, 132.7, 129.3, 129.0 (2C), 127.0 (2C), 122.8, 122.3, 120.4, 57.6, 44.3 (2C), 36.51.

1-methyl-4-[3-(N-benzenesulfonyl)-aminobenzoyl]-piperazine (1d, XH10103)

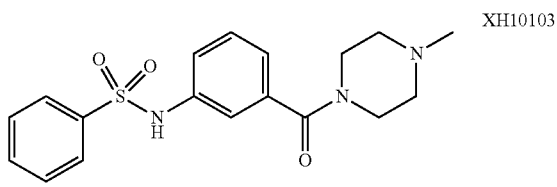

C$_{18}$H$_{21}$N$_3$O$_3$S
Mol. Wt.: 359.4

Following general synthetic procedure of 1-42, 3-(N-benzenesulfonyl)-amino-benzoic acid reacted with 1-methyl piperazine to give 1d, yield 39.1%. $^1$H NMR (400 MHz, CDCl$_3$) δ 7.76-7.74 (d, J=6.8 Hz, 2H), 7.50-7.46 (t, J=8.0 Hz, 1H), 7.38-7.35 (t, J=8.0 Hz, 2H), 7.28-7.22 (m, 2H), 7.10-7.08 (m, 2H), 3.81 (br s, 2H), 3.31 (br s, 2H), 2.57 (br s, 2H), 2.40 (br s, 2H), 2.35 (s, 3H). $^{13}$C NMR (100 MHz, CDCl$_3$) δ 169.5, 139.1, 137.4, 136.2, 132.9, 129.5, 129.0 (2C), 127.1 (2C), 123.3, 122.4, 120.0, 54.9, 54.4, 47.2, 45.7, 41.9.

1-Ethyl-4-[3-(N-benzenesulfonyl)-aminobenzoyl]-piperazine (1e, XH10104)

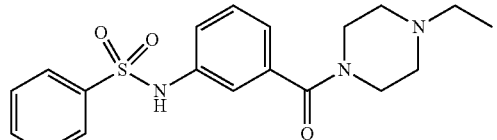

C$_{19}$H$_{23}$N$_3$O$_3$S
Mol. Wt.: 373.5

Following general synthetic procedure of 1-42, 3-(N-benzenesulfonyl)-amino-benzoic acid reacted with 1-ethyl piperazine to give 1e, yield 39.8%. $^1$H NMR (400 MHz, CDCl$_3$) 7.79-7.77 (d, J=7.2 Hz, 2H), 7.51-7.47 (m, 1H), 7.41-7.37 (m, 2H), 7.30-7.23 (m, 2H), 7.15 (s, 1H), 7.11-7.09 (d, J=6.8 Hz, 1H), 3.89 (br s, 2H), 3.42 (br s, 2H), 2.70 (br s, 2H), 2.64-2.63 (m, 2H), 2.54 (br s, 2H), 1.20-1.16 (m, 3H). $^{13}$C NMR (100 MHz, CDCl$_3$) δ 169.4, 139.1, 137.4, 135.9, 132.9, 129.6, 129.0 (2C), 127.1 (2C), 123.5, 122.5, 119.9, 52.5, 52.2, 51.8, 46.6, 41.3, 11.0.

N-(2-methoxyl-ethyl)-3-[(N-4-chlorobenzenesulfonyl)-amino]-benzamide (1g, XH10106)

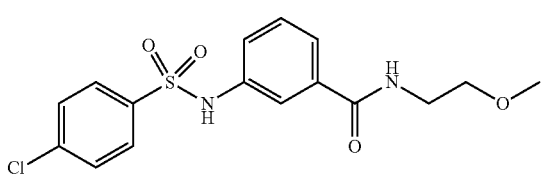

C$_{16}$H$_{17}$ClN$_2$O$_4$S
Mol. Wt.: 368.8

Following general synthetic procedure of 1-42, 3-(N-4-chlorobenzenesulfonyl)-amino-benzoic acid reacted with 2-methoxyethanamine to give 1g, yield 85.9%. $^1$H NMR (400 MHz, CDCl$_3$) δ 9.31 (s, 1H), 7.84 (s, 1H), 7.71-7.69 (d, J=8.4 Hz, 2H), 7.54-7.52 (d, J=7.6 Hz, 1H), 7.38-7.40 (d, J=7.2 Hz, 1H), 7.29-7.20 (m, 3H), 7.02 (m, 1H), 3.72-3.71 (t, J=4.8 Hz, 2H), 3.61-3.59 (t, J=4.8 Hz, 2H), 3.33 (s, 3H). $^{13}$C NMR (100 MHz, CDCl$_3$) δ 167.0, 139.2, 138.0, 137.7, 134.8, 129.2 (2C), 128.6 (2C), 123.0, 122.0, 120.7, 71.1, 58.7, 40.0.

1-Ethyl-4-[3-(N-4-chlorobenzenesulfonyl)-aminobenzoyl]-piperazine (1h, XH10107)

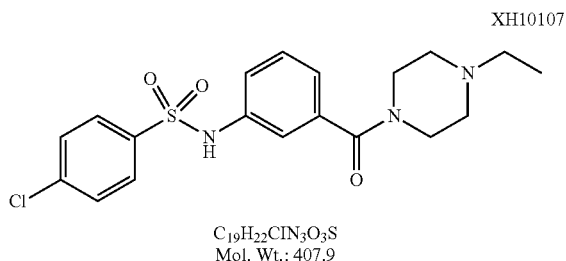 [SMILES: CCN1CCN(C(=O)c2cccc(NS(=O)(=O)c3ccc(Cl)cc3)c2)CC1]

C$_{19}$H$_{22}$ClN$_3$O$_3$S
Mol. Wt.: 407.9

Following general synthetic procedure of 1-42, 3-(N-4-chlorobenzenesulfonyl)-amino-benzoic acid reacted with 1-ethyl piperazine to give 1h, yield 46.0%. $^1$H NMR (400 MHz, CDCl$_3$) δ 8.90 (br s, 1H), 7.69-7.67 (d, J=8.8 Hz, 2H), 7.32-7.30 (m, 3H), 7.27-7.25 (m, 1H), 7.15 (s, 1H), 7.10-7.08 (d, J=7.2 Hz, 1H), 3.89 (br s, 2H), 3.41 (br s, 2H), 2.69 (br s, 2H), 2.62-2.60 (m, 2H), 2.52 (br s, 2H), 1.18-1.14 (m, 3H). $^{13}$C NMR (100 MHz, CDCl$_3$) δ 169.5, 139.3, 137.7, 137.4, 135.9, 129.6, 129.2 (2C), 128.7 (2C), 123.4, 122.6, 120.1, 52.5, 52.2, 51.9, 46.8, 41.4, 11.1.

N-propyl-3-[(N-4-chlorobenzenesulfonyl)-amino]-benzamide 1i, XH10108

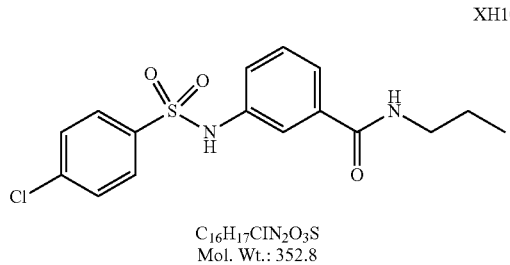

C$_{16}$H$_{17}$ClN$_2$O$_3$S
Mol. Wt.: 352.8

Following general synthetic procedure of 1-42, 3-(N-4-chlorobenzenesulfonyl)-amino-benzoic acid reacted with propylamine to give 1i, yield 90.1%. $^1$H NMR (400 MHz, CDCl$_3$) δ 8.99 (s, 1H), 7.84 (s, 1H), 7.73-7.71 (d, J=8.8 Hz, 2H), 7.55-7.53 (d, J=8.0 Hz, 1H), 7.37-7.28 (m, 4H), 6.41 (m, 1H), 3.52-3.47 (m, 2H), 1.66-1.61 (m, 2H), 0.95-0.98 (m, 3H). $^{13}$C NMR (100 MHz, CDCl$_3$) δ 166.9, 139.3, 138.1, 137.8, 135.3, 129.4, 129.2 (2C), 128.6 (2C), 123.2, 121.9, 120.8.

N-(2-methoxyl-ethyl)-3-[(N-4-methylbenzenesulfonyl)-amino]-benzamide (1j, XH10110)

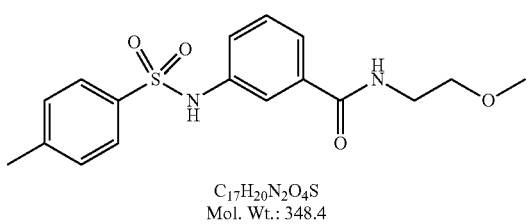

C$_{17}$H$_{20}$N$_2$O$_4$S
Mol. Wt.: 348.4

Following general synthetic procedure of 1-42, 3-(N-4-methylbenzenesulfonyl)-amino-benzoic acid reacted with 2-methoxyethanamine to give 1j, yield 66.1%. $^1$H NMR (400 MHz, CDCl$_3$) δ 8.84 (s, 1H), 7.82 (s, 1H), 7.68-7.66 (d, J=8.4 Hz, 2H), 7.55-7.53 (d, J=8.0 Hz, 1H), 7.36-7.34 (d, J=8.0 Hz, 1H), 7.29-7.25 (t, J=7.6 Hz, 1H), 7.16-7.14 (d, J=7.6 Hz, 2H), 6.75 (m, 1H), 3.74-3.72 (t, J=5.6 Hz, 2H), 3.60-3.57 (t, J=5.6 Hz, 2H), 3.37 (s, 3H), 2.32 (s, 3H). $^{13}$C NMR (100 MHz, CDCl$_3$) δ 166.9, 143.7, 138.4, 136.3, 134.9, 129.6 (2C), 129.3, 127.1 (2C), 122.8, 121.7, 120.4, 71.1, 5.88, 39.9, 21.5.

1-Ethyl-4-[3-(N-4-methylbenzenesulfonyl)-aminobenzoyl]-piperazine (1k, XH10111)

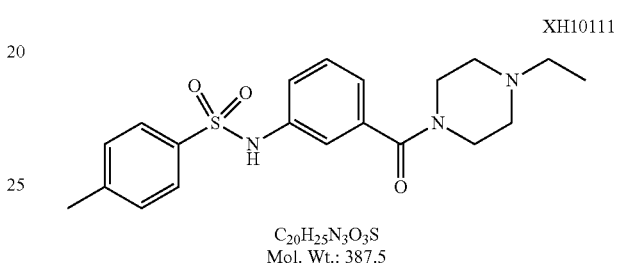

C$_{20}$H$_{25}$N$_3$O$_3$S
Mol. Wt.: 387.5

Following general synthetic procedure of 1-42, 3-(N-4-methylbenzenesulfonyl)-amino-benzoic acid reacted with 1-ethylpiperazine to give 1k, yield 55.2%. $^1$H NMR (400 MHz, CDCl$_3$) δ 7.63-7.61 (d, J=8.4 Hz, 2H), 7.26-7.23 (m, 2H), 7.16-7.14 (d, J=7.6 Hz, 2H), 7.09-7.07 (m, 2H), 3.80 (br s, 2H), 3.30 (br s, 2H), 2.51 (br s, 2H), 2.45-2.43 (q, J=8.0 Hz, 2H), 2.33 (s, 3H), 2.31 (br s, 2H), 1.10-1.06 (t, J=8.0 Hz, 3H). $^{13}$C NMR (100 MHz, CDCl$_3$) δ 169.6, 143.9, 137.7, 136.5, 136.4, 129.7 (2C), 129.3, 127.4 (2C), 123.4, 122.4, 120.2, 53.1, 52.5, 52.3, 47.8, 42.4, 21.7, 12.0.

N-propyl-3-[(N-4-methylbenzenesulfonyl)-amino]-benzamide (1l, XH10112)

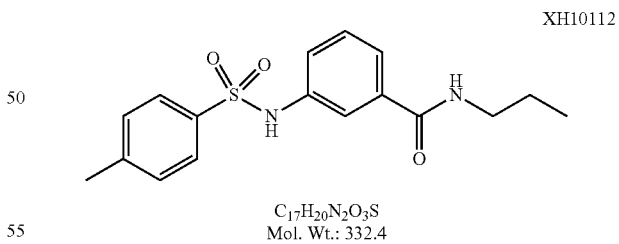

C$_{17}$H$_{20}$N$_2$O$_3$S
Mol. Wt.: 332.4

Following general synthetic procedure of 1-42, 3-(N-4-methylbenzenesulfonyl)-amino-benzoic acid reacted with propylamine to give 1l, yield 83.8%. $^1$H NMR (400 MHz, CDCl$_3$) δ 8.78 (s, 1H), 7.75 (s, 1H), 7.66-7.64 (d, J=8.0 Hz, 2H), 7.46-7.44 (d, J=8.0 Hz, 1H), 7.40-7.38 (d, J=8.0 Hz, 1H), 7.24-7.20 (m, 1H), 7.13-7.11 (d, J=8.4 Hz, 2H), 6.58 (m, 1H), 3.45-3.40 (m, 2H), 2.29 (s, 3H), 1.61-1.56 (m, 2H), 0.93-0.89 (m, 3H). $^{13}$C NMR (100 MHz, CDCl$_3$) δ 167.1, 143.8, 138.1, 136.3, 135.4, 129.7 (2C), 129.4, 127.2 (2C), 123.1, 122.2, 120.3, 42.0, 22.8, 21.5, 11.4.

N-propyl-[4-(N-benzenesulfonyl)-amino-pyridine-2-yl]-carboxamide (1m, XH10113)

XH10113

$C_{15}H_{17}N_3O_3S$
Mol. Wt.: 319.4

Following general synthetic procedure of 1-42, 4-(N-benzenesulfonyl)-aminopyridine-2-carboxylic acid reacted with propylamine to give 1m, yield 89.6%. $^1$H NMR (400 MHz, Acetone-d6) δ 8.75 (d, J=1.6 Hz, 1H), 8.47 (d, J=2.4 Hz, 1H), 8.09-8.07 (m, 1H), 7.94 (br s, 1H), 7.84-7.82 (d, J=8.0 Hz, 2H), 7.66-7.63 (m, 1H), 7.58-7.55 (m, 2H), 3.45-3.40 (m, 2H), 1.61-1.56 (m, 2H), 0.93-0.89 (m, 3H). $^{13}$C NMR (100 MHz, Acetone-d6) δ 165.5, 145.6, 145.4, 140.8, 135.8, 132.4, 130.7, 1128.1, 42.7, 23.9, 12.2.

N-(2-methoxylethyl)-[4-(N-benzenesulfonyl)-amino-pyridine-2-yl]-carboxamide (1n, XH10114)

XH10114

$C_{15}H_{17}N_3O_4S$
Mol. Wt.: 335.4

Following general synthetic procedure of 1-42, 4-(N-benzenesulfonyl)-aminopyridine-2-carboxylic acid reacted with 2-methoxyethanamine to give 1n, yield 74.0%. $^1$H NMR (400 MHz, Acetone-d6) δ 8.73-8.72 (d, J=1.6 Hz, 1H), 8.45 (d, J=2.4 Hz, 1H), 8.05-8.04 (m, 1H), 7.95 (br s, 1H), 7.79-7.77 (d, J=8.0 Hz, 2H), 7.58-7.56 (t, J=7.2 Hz, 2H), 7.52-7.48 (m, 2H), 3.55-3.48 (m, 4H), 3.27 (s, 3H). $^{13}$C NMR (100 MHz, Acetone-d6) δ 169.9, 149.8, 149.5, 144.9, 140.0, 138.8, 136.3, 134.8 (2C), 132.5 (2C), 132.3, 76.2, 63.3, 45.0.

1-Ethyl-4-[5-(N-benzenesulfonyl)-amino-2-fluorobenzoyl]-piperazine (1o, XH10117)

XH10117

$C_{19}H_{22}FN_3O_3S$
Mol. Wt.: 391.5

Following general synthetic procedure of 1-42, 5-(N-benzenesulfonyl)-amino-2-fluorobenzoic acid reacted with 1-ethylpiperazine to give 1o, yield 61.1%. $^1$H NMR (400 MHz, CDCl$_3$) δ 7.80-7.68 (d, J=7.6 Hz, 2H), 7.47-7.43 (t, J=8.0 Hz, 1H), 7.36-7.32 (t, J=7.6 Hz, 2H), 7.34-7.27 (m, 1H), 6.93-6.90 (m, 2H), 3.78 (br s, 2H), 3.16 (br s, 2H), 2.46 (brs, 2H), 2.43-2.38 (q, J=7.2 Hz, 2H), 1.06-1.03 (t, J=7.2 Hz, 3H,). $^{13}$C NMR (100 MHz, CDCl$_3$) δ 164.4, 156.4 & 154.2 (1C), 139.0, 133.8, 132.8, 128.9 (2C), 127.1, 125.3 & 125.2 (1C), 124.0 &123.8 (1C), 122.8, 116.7 &116.4 (1C), 52.7, 52.1, 42.3, 11.8.

1-Ethyl-4-[3-(N-benzenesulfonyl)-amino-4-methyl-benzoyl]-piperazine (1p, XH10118)

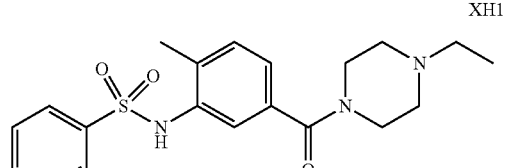

XH10118

$C_{20}H_{25}N_3O_3S$
Mol. Wt.: 387.5

Following general synthetic procedure of 1-42, 3-(N-benzenesulfonyl)-amino-4-methylbenzoic acid reacted with 1-ethylpiperazine to give 1o, yield 58.2%. $^1$H NMR (400 MHz, Acetone-d6) δ 7.69-7.67 (d, J=8.0 Hz, 2H), 7.62-7.60 (m, 1H), 7.52-7.48 (t, J=8.0 Hz, 2H), 7.18-7.16 (d, J=8.0 Hz, 1H), 7.12-7.10 (d, J=7.6 Hz, 1H), 7.08 (s, 1H), 3.54 (br s, 2H), 3.25 (br s, 2H), 2.37-2.31 (m, 6H), 2.07 (s, 3H), 1.01-0.98 (m, 3H). $^{13}$C NMR (100 MHz, Acetone-d6) δ 169.6, 141.8, 136.7, 136.0, 135.8, 134.0, 132.1, 130.3 (2C), 128.1 (2C), 126.6, 126.0, 53.8, 53.0, 48.6, 43.1, 18.3, 14.7.

N-butyl-[4-(N-benzenesulfonyl)-amino-pyridine-2-yl]-carboxamide (1q, XH10119)

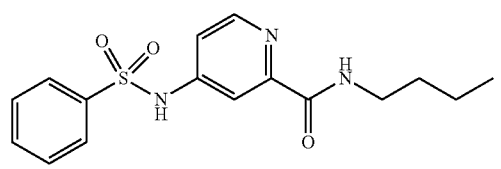

XH10119

$C_{16}H_{19}N_3O_3S$
Mol. Wt.: 333.4

Following general synthetic procedure of 1-42, 4-(N-benzenesulfonyl)-aminopyridine-2-carboxylic acid reacted with butylamine to give 1q, yield 67.9%. $^1$H NMR (400 MHz, Acetone-d6) δ 9.32 (br s, 1H), 8.70 (s, 1H), 8.42 (d, J=2.4 Hz, 1H), 8.03 (s, 1H), 7.88 (br s, 1H), 7.79-7.77 (d, J=7.6 Hz, 2H), 7.61-7.57 (m, 1H), 7.53-7.49 (m, 2H), 3.30-3.36 (m, 2H), 1.56-1.48 (m, 2H), 1.37-1.30 (m, 2H), 0.89-0.85 (t, J=7.6 Hz, 3H). $^{13}$C NMR (100 MHz, Acetone-d6) δ 165.4, 145.5, 145.3, 140.7, 135.7, 134.5, 132.3, 130.6 (2C), 128.3 (2C), 128.0, 40.6, 32.7, 21.1, 14.4.

51

1-methyl-4-[5-(N-benzenesulfonyl)-amino-2-fluorobenzoyl]-piperazine XH10120

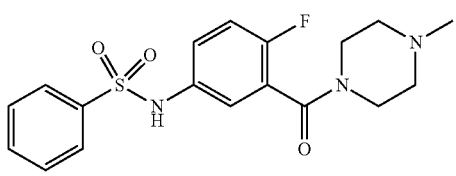 [SMILES: CN1CCN(C(=O)c2cc(NS(=O)(=O)c3ccccc3)ccc2F)CC1]

Following general synthetic procedure of 1-42, 5-(N-benzenesulfonyl)-)-amino-2-fluorobenzoic acid reacted with 1-methyl piperazine to give XH10120, yield. $^1$H NMR (400 MHz, CDCl$_3$) δ 7.73 (s, 1H), 7.71 (s, 1H), 7.50-7.46 (m, 1H), 7.40-7.36 (m, 2H), 7.30-7.26 (m, 1H), 6.97-6.93 (m, 2H), 3.80 (br s, 2H), 3.20 (br s, 2H), 2.48 (s, 2H), 2.31 (m, 5H). $^{13}$C NMR (100 MHz, CDCl$_3$) δ 164.4, 156.5&154.0 (1C), 139.0, 133.7, 132.9, 129.0 (2C), 127.1 (2C), 125.3 & 125.2 (1C), 124.1 & 123.9 (1C), 122.7, 116.8 &116.5 (1C), 54.9, 54.4, 46.9, 45.8, 42.1.

N-[2-(N,N-dimethylamino)-ethyl]-3-[(N-benzenesulfonyl)-amino-4-methyl]-benzamide XH10121-spot2

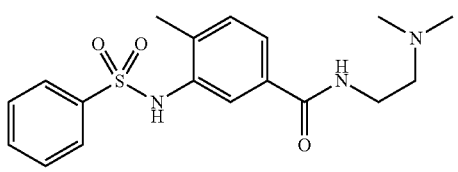 [SMILES: Cc1ccc(C(=O)NCCN(C)C)cc1NS(=O)(=O)c1ccccc1]

$^1$H NMR (400 MHz, CDCl$_3$) δ 8.24 (br s, 1H), 7.68-7.64 (m, 4H), 7.48-7.46 (m, 1H), 7.37-7.33 (m, 2H), 7.04-7.02 (d, J=8.4 Hz, 1H), 3.81-3.80 (m, 2H), 3.21-3.18 (m, 2H), 2.78 (s, 6H), 1.98 (s, 3H). $^{13}$C NMR (100 MHz, CDCl$_3$) δ 167.1, 139.5, 137.6, 134.5, 132.8, 132.2, 130.0, 129.0 (2C), 127.1 (2C), 125.6, 125.4, 58.2, 44.0, 35.5, 17.9.

N-(2-methoxyl-ethyl)-3-[(N-benzenesulfonyl)-amino]-4-methylbenzamide XH10122-spot2

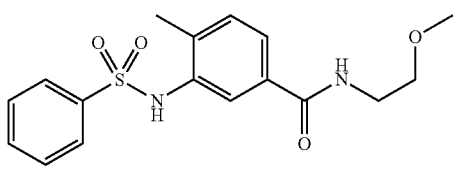 [SMILES: COCCNC(=O)c1ccc(C)c(NS(=O)(=O)c2ccccc2)c1]

$^1$H NMR (400 MHz, CDCl$_3$) δ 7.72-7.70 (m, 1H), 7.70-7.69 (m, 1H), 7.60-7.59 (m, 1H), 7.55-7.53 (m, 2H), 7.45-7.41 (m, 2H), 7.16-7.14 (d, J=8.0 Hz, 1H), 6.46 (s, 1H), 6.41 (m, 1H), 3.62-3.59 (m, 2H), 3.54-3.52 (m, 2H), 3.38 (s, 3H), 2.01 (s, 3H). $^{13}$C NMR (100 MHz, CDCl$_3$) δ 166.5, 139.3, 135.6, 134.4, 133.5, 133.2, 131.1, 129.1 (2C), 127.1 (2C), 125.4, 123.0, 71.1, 58.3, 39.7, 17.6.

52

1-methyl-4-[3-(N-2-fluorobenzenesulfonyl)-amino] piperazine XH10127

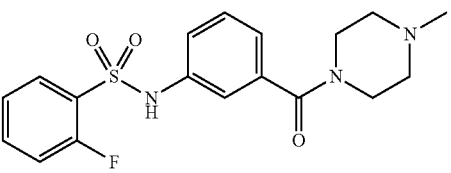 [SMILES: CN1CCN(C(=O)c2cccc(NS(=O)(=O)c3ccccc3F)c2)CC1]

$^1$H NMR (400 MHz, CDCl$_3$) δ 7.83-7.80 (m, 1H), 7.54-7.48 (m, 2H), 7.24-7.10 (m, 6H), 3.78 (br s, 2H), 3.29 (br s, 2H), 2.49 (br s, 2H), 2.32 (m, 5H). $^{13}$C NMR (100 MHz, CDCl$_3$) δ 169.3, 160.0 &157.4 (1C), 136.6, 135.5 &135.4 (1C), 130.8, 129.6, 127.0 & 126.9, 124.5, 123.9, 122.3, 120.0, 117.1 & 116.9 (1C), 55.1, 54.6, 47.4, 45.9, 42.1.

1-ethyl-4-[3-(N-2-fluorobenzenesulfonyl)-amino] piperazine XH10128

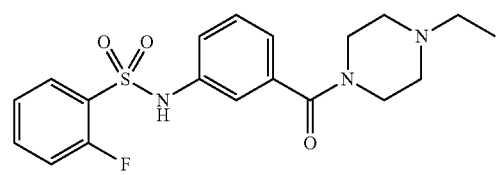 [SMILES: CCN1CCN(C(=O)c2cccc(NS(=O)(=O)c3ccccc3F)c2)CC1]

1H NMR (400 MHz, CDCl$_3$) δ 7.85-7.80 (t d, J$_1$=7.6 Hz, J$_2$=1.6 Hz, 1H), 7.53-7.48 (m, 1H), 7.27-7.10 (m, 6H), 3.79 (br s, 2H), 3.30 (br s, 2H), 2.52 (br s, 2H), 2.47-2.42 (m, 2H), 2.33 (br s, 2H), 1.11-1.08 (m, 3H). $^{13}$C NMR (100 MHz, CDCl$_3$) δ 169.2, 160.0 & 157.4 (1C), 136.7, 136.5, 135.5 &135.4 (1C), 130.8, 129.6, 127.0 &126.8 (1C), 124.5, 123.9, 122.1, 119.9, 117.1 & 116.9 (1C), 53.0, 52.3, 52.2, 47.6, 42.2.

N-(2-methoxyl-ethyl)-3-[(N-2-fluorobenzenesulfonyl)-amino]-benzamide XH10129

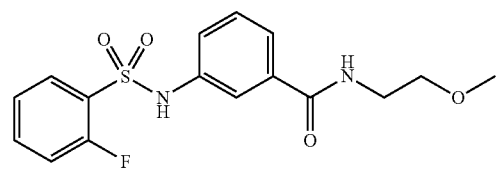 [SMILES: COCCNC(=O)c1cccc(NS(=O)(=O)c2ccccc2F)c1]

$^1$H NMR (400 MHz, CDCl$_3$) δ 8.93 (s, 1H), 7.90-7.86 (m, 2H), 7.50-7.47 (m, 2H), 7.37-7.35 (d, J=8.0 Hz, 1H), 7.27-7.23 (m, 1H), 7.20-7.16 (t, J=9.6 Hz, 1H), 6.71 (m, 1H), 3.74-3.71 (m, 2H), 3.60-3.57 (m, 2H), 3.37 (s, 3H). $^{13}$C NMR (100 MHz, CDCl$_3$) δ 166.6, 160.1 & 157.5 (1C), 137.6, 135.3, 135.1, 130.8, 129.3, 127.1 &127.0 (1C), 124.4 &124.3 (1C), 122.4, 122.1, 120.3, 117.2 & 116.9 (1C), 71.1, 58.8, 39.9.

N-(2-methoxylethyl)-[4-(N-2-fluorobenzenesulfo-nyl)-amino-pyridine-2-yl]-carboxamide XH10130

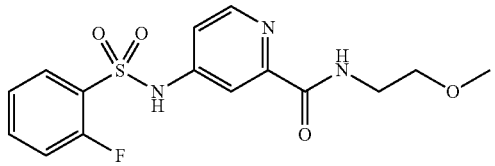 [SMILES: COCCNC(=O)c1cc(NS(=O)(=O)c2ccccc2F)ccn1]

$^1$H NMR (400 MHz, CDCl$_3$) δ 8.69-8.68 (m, 2H), 8.22 (s, 1H), 7.93-7.89 (t, J=7.2 Hz, 1H), 7.55-7.51 (m, 1H), 7.24-7.20 (t, J=8.0 Hz, 1H), 7.14-7.10 (t, J=9.6 Hz, 1H), 7.02-6.99 (t, J=5.2 Hz, 1H), 3.71-3.74 (m, 2H), 3.58-3.60 (m, 2H), 3.37 (s, 3H). $^{13}$C NMR (100 MHz, CDCl$_3$) δ 164.9, 160.0 & 157.4 (1C), 143.2 &142.7 (1C), 135.8, 134.4, 130.8, 130.4, 127.6, 126.8 &126.7 (1C), 124.7, 117.3 &117.0, 70.8, 58.8, 40.0.

1-methyl-4-[5-(N-2-fluorobenzenesulfonyl)-amino-2-fluorobenzoyl]-piperazine XH10131

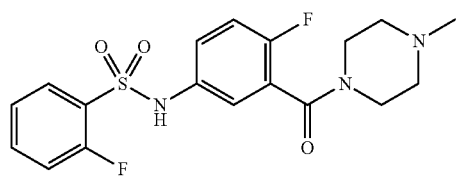 [SMILES: CN1CCN(C(=O)c2cc(NS(=O)(=O)c3ccccc3F)ccc2F)CC1]

$^1$H NMR (400 MHz, CDCl$_3$) δ 7.80-7.76 (t d, J$_1$=7.2 Hz, J$_2$=1.6 Hz, 1H), 7.53-7.51 (m, 1H), 7.25-7.23 (m, 1H), 7.20-7.14 (m, 2H), 7.12-7.08 (m, 1H), 6.97-6.92 (m, 1H), 3.79 (br s, 2H), 3.20 (br s, 2H), 2.48 (m, 2H), 2.31 (m, 5H). $^{13}$C NMR (100 MHz, CDCl$_3$) δ 164.1, 160.0 &157.4 (1C), 156.8 &154.3 (1C), 135.5 &135.4 (1C), 132.9, 130.8, 126.8 & 126.7 (1C), 125.0 &124.9 (1C), 124.5 & 124.4 (1C), 124.2, 122.6, 117.1 & 116.9 (1C), 116.9 &116.6 (1C), 54.9, 54.4, 46.9, 45.9, 42.0.

1-methyl-4-[5-(N-2-fluorobenzenesulfonyl)-amino-2-fluorobenzoyl]-piperazine XH10132

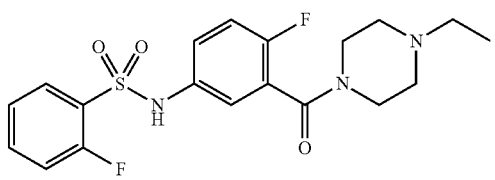 [SMILES: CCN1CCN(C(=O)c2cc(NS(=O)(=O)c3ccccc3F)ccc2F)CC1]

$^1$H NMR (400 MHz, CDCl$_3$) δ 7.80-7.77 (t, J=6.8 Hz, 1H), 7.53-7.50 (m, 1H), 7.26-7.24 (m, 1H), 7.20-7.16 (t, J=8.0 Hz, 1H), 7.15-7.09 (m, 2H), 6.95-6.91 (t, J=8.4 Hz, 1H), 3.80 (br s, 2H), 3.21 (m, 2H), 2.51 (br s, 2H), 2.41-2.46 (q, J=7.2 Hz, 2H), 2.33 (br s, 2H), 1.09-1.06 (t, J=7.2 Hz, 3H). $^{13}$C NMR (100 MHz, CDCl$_3$) δ 164.1, 160.0 &157.4 (1C), 156.7 &154.2 (1C), 135.5 &135.4 (1C), 133.0, 130.7, 126.9 &126.8, 124.9 &124.8 (1C), 124.5, 124.4 & 124.2 (1C), 122.6, 117.1 & 116.9 (1C), 116.8 & 116.5 (1C), 52.8, 52.1, 47.0, 42.1, 11.8.

N-(2-methoxyl-ethyl)-[5-(N-2-fluorobenzenesulfo-nyl)-amino-2-fluoro]-benzamide XH10133

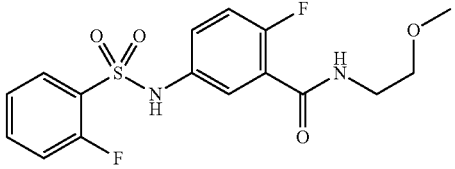 [SMILES: COCCNC(=O)c1cc(NS(=O)(=O)c2ccccc2F)ccc1F]

$^1$H NMR (400 MHz, CDCl$_3$) δ 9.55 (s, 1H), 8.17-8.15 (m, 1H), 7.87-7.83 (t, J=7.2 Hz, 1H), 7.62-7.60 (m, 1H), 7.51-7.45 (m, 1H), 7.34-7.30 (m, 1H), 7.20-7.16 (t, J=8.0 Hz, 1H), 7.10-6.98 (m, 2H), 3.82-3.79 (m, 2H), 3.60-3.58 (m, 2H), 3.37 (s, 3H). $^{13}$C NMR (100 MHz, CDCl$_3$) δ 162.8, 160.1&157.5 (1C), 158.8 &156.4 (1C), 135.3 &135.2 (1C), 134.1, 130.7, 127.0, 124.7 &124.6 (1C), 124.3, 124.1, 120.9 &120.8 (1C), 117.2 &117.0 (1C), 117.0 & 116.7 (1C), 70.9, 58.8, 40.1.

N-propyl-[5-(N-2-fluorobenzenesulfonyl)-amino-2-fluoro]-benzamide XH10134

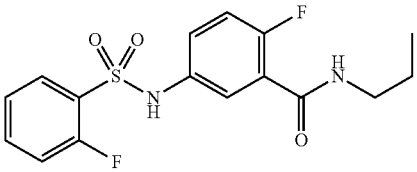 [SMILES: CCCNC(=O)c1cc(NS(=O)(=O)c2ccccc2F)ccc1F]

$^1$H NMR (400 MHz, Acetone-d6) δ 9.20 (br s, 1H), 7.82-7.81 (m, 1H), 7.70-7.68 (m, 1H), 7.66-7.61 (m, 1H), 7.40 (br s, 1H), 7.39-7.31 (m, 1H), 7.31-7.25 (m, 2H), 7.10-7.05 (m, 1H), 3.31-3.26 (m, 2H), 1.55-1.51 (m, 2H), 0.89-0.85 (m, 3H). $^{13}$C NMR (100 MHz, Acetone-d6) δ 162.2, 159.9 & 157.4 (1C), 158.3 &155.9 (1C), 135.9 &135.8 (1C), 133.7, 130.7, 127.2 &127.1 (1C), 124.9 &124.8 (1C), 124.7, 123.8 &123.6 (1C), 123.4 &123.3 (1C), 117.2 & 116.9, 116.9 &116.7 (1C), 41.3, 22.5, 10.7.

N-[2-(N, N-dimethylamino)-ethyl]-3-[(N-2-fluorobenzenesulfonyl)-amino-4-methyl]-benzamide XH10135

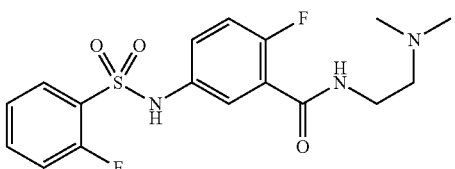

$^1$H NMR (400 MHz, CDCl$_3$) δ 8.48 (br s, 1H), 8.08-8.06 (m, 1H), 7.86-7.82 (m, 1H), 7.58-7.48 (m, 3H), 7.19-7.16 (t, J=8.0 Hz, 1H), 7.11-7.06 (t, J=9.6 Hz, 1H), 7.01-7.00 (m, 1H), 3.69-3.65 (m, 2H), 2.58-2.55 (m, 2H), 2.28 (s, 6H). $^{13}$C NMR (100 MHz, CDCl$_3$) δ 162.7, 160.1 & 157.5, 158.9 & 156.4, 135.2, 133.9, 130.7, 127.2 & 127.0 (1C), 125.0 & 124.9 (1C), 124.3, 121.2 & 121.1 (1C), 117.1 & 117.0 (1C), 117.0 & 116.7 (1C), 57.3, 45.0 (2C), 37.6.

fx-2176

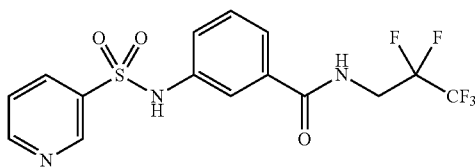

¹H NMR (400 MHz, CDCl₃) δ 9.00 (s, 1H), 8.78-8.73 (m, 2H), 8.14-8.12 (d, J=8.4 Hz, 1H), 7.85-7.77 (m, 1H), 7.65 (s, 1H), 7.51-7.45 (m, 4H), 7.36-7.32 (m, 1H), 6.91 (s, 1H), 4.23-4.15 (m, 2H). ¹³C NMR (100 MHz, CDCl₃) δ 167.2, 152.2, 147.1, 137.0, 136.4, 136.2, 134.3, 130.0, 127.5, 127.0, 125.0, 124.4, 123.9, 120.8, 111.6, 39.2.

fx-2175

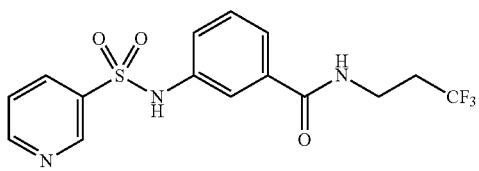

¹H NMR (400 MHz, CDCl₃) δ 9.00 (s, 1H), 8.94 (s, 1H), 8.73 (s, 1H), 8.12-8.10 (d, J=8.4 Hz, 1H), 7.71 (s, 1H), 7.55-7.53 (d, J=7.6 Hz, 1H), 7.41 (m, 2H), 7.36-7.34 (m, 1H), 6.76 (s, 1H), 3.77-3.76 (d, J=5.6 Hz, 2H), 2.52-2.48 (m, 2H). ¹³C NMR (100 MHz, CDCl₃) δ 167.0, 152.6, 147.3, 137.2, 136.3, 135.7, 134.8, 129.9, 124.2, 124.1, 123.0, 120.8, 33.7.

N-(cyclopropylmethyl)-3-(pyridine-3-sulfonamido)benzamide Compound 40 (FX3073)

FX-3073

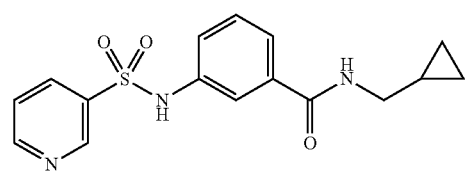

Compound 40 (FX3073) was synthesized using the general synthetic procedures for compounds 1-42 (x %): ¹H NMR (400 MHz, CDCl₃) δ 9.21 (s, 1H), 9.02 (s, 1H), 8.72 (s, 1H), 8.14-8.12 (d, J=7.2 Hz, 1H), 7.78 (s, 1H), 7.59-7.57 (d, J=7.2 Hz, 1H), 7.42-7.34 (m, 3H), 6.48 (s, 1H), 3.38 (s, 2H), 1.05 (s, 1H), 0.57-0.55 (d, J=7.2 Hz, 2H), 0.30-0.29 (d, J=2.8 Hz, 2H). ¹³C NMR (100 MHz, CDCl₃) δ 166.7, 152.3, 147.3, 137.4, 135.8, 135.4, 129.6, 124.1, 123.9, 122.6, 121.2, 45.2, 10.6, 3.57.

N-hexyl-3-(pyridine-3-sulfonamido)benzamide Compound 39 (FX3071)

FX-3071

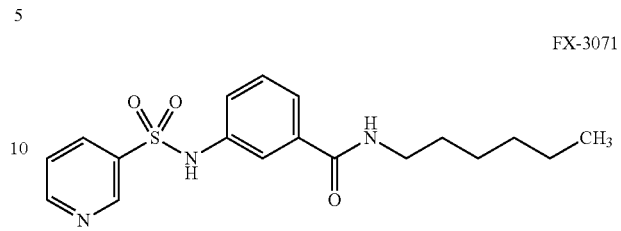

Compound 39 (FX3071) was synthesized using the general synthetic procedures for compounds 1-42 (x %): ¹H NMR (400 MHz, DMSO-d6) δ 10.67 (s, 1H), 8.88 (s, 1H), 8.78 (s, 1H), 8.43 (s, 1H), 8.13-8.11 (d, J=6.8 Hz, 1H), 7.62-7.51 (m, 3H), 7.33-7.31 (m, 1H), 7.25-7.23 (m, 1H), 4.45 (br s, 4H), 3.20-3.19 (d, J=5.2 Hz, 2H), 1.47 (s, 2H), 1.26 (m, 6H), 0.85 (m, 3H). ¹³C NMR (100 MHz, DMSO-d6) δ 165.4, 153.6, 147.0, 137.2, 136.0, 134.8, 129.2, 124.5, 123.0, 122.9, 119.9, 31.0, 29.0, 26.1, 22.1, 13.9.

N-pentyl-3-(pyridine-3-sulfonamido)benzamide Compound 38 (FX3069)

FX-3069

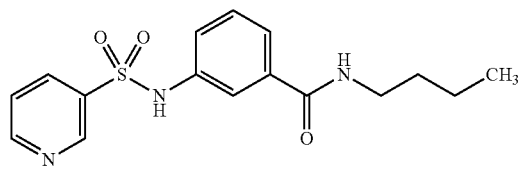

Compound 38 (FX3069) was synthesized using the general synthetic procedures for compounds 1-42 (x %): ¹H NMR (400 MHz, CDCl₃) δ 9.00 (m, 2H), 8.76 (br s, 1H), 8.11-8.10 (d, J=6.8 Hz, 1H), 7.77 (s, 1H), 7.59-7.57 (d, J=7.2 Hz, 1H), 7.38-7.33 (m, 3H), 6.31 (s, 1H), 3.52-3.51 (d, J=6.0 Hz, 2H), 1.62 (s, 2H), 1.36 (s, 4H), 0.90 (s, 3 Hz). ¹³C NMR (100 MHz, CDCl₃) δ 166.7, 152.8, 14.7, 137.5, 135.4, 135.1, 129.6, 123.8, 122.3, 121.1, 40.4, 29.3, 29.0, 22.4, 14.0.

N-butyl-3-(pyridine-3-sulfonamido)benzamide Compound 37 (FX3067)

FX-3067

Compound 37 (FX3067) was synthesized using the general synthetic procedures for compounds 1-42 (x %): ¹H NMR (400 MHz, CDCl₃) δ 9.27 (s, 1H), 9.00 (s, 1H), 8.67 (s, 1H), 8.09-8.07 (d, J=7.2 Hz, 1H), 7.80 (s, 1H), 7.60-7.58 (d, J=6.0 Hz, 1H), 7.36-7.32 (m, 3H), 6.38 (s, 1H), 3.54-3.52

(d, J=5.6 Hz, 2H), 1.61-1.59 (m, 2H), 1.42-1.40 (m, 2H), 0.96-0.94 (m, 3H). $^{13}$C NMR (100 MHz, CDCl$_3$) δ 166.8, 153.1, 147.8, 137.7, 136.1, 135.3, 135.0, 129.6, 123.7, 122.1, 121.2, 40.1, 31.6, 20.1, 13.8.

N-(2-methoxyethyl)-3-(pyridine-3-sulfonamido)benzamide Compound 31 (FX2147)

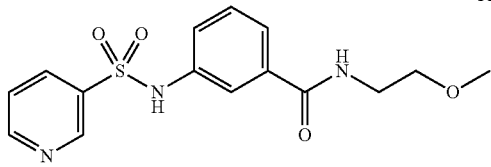

Compound 31 (FX2147) was synthesized using the general synthetic procedures for compounds 1-42 (x %): $^1$H NMR (400 MHz, CDCl$_3$) δ 3.38 (s, 3H), 4.33-4.41 (t, J=6.4 Hz, 2H), 4.70-4.80 (t, J=6.4 Hz, 2H), 6.79 (s, 1H), 7.30-7.43 (m, 3H), 7.60-7.70 (d, J=7.2 Hz, 1H), 7.83 (s, 1H), 8.09-8.11 (d, J=8.0 Hz, 1H), 8.70-8.72 (d, J=3.2 Hz, 1H), 9.01 (s, 1H), 9.18 (s, 1H); $^{13}$C NMR (100 MHz, CDCl$_3$) δ 40.3, 59.1, 71.3, 121.5, 122.5, 123.8, 124.1, 129.9, 135.2, 135.4, 138.1, 148.1, 153.3, 167.0; MS (ESI) m/z=[M+H]+.

N-propyl-3-(pyridine-3-sulfonamido)benzamide Compound 32 (FX2149)

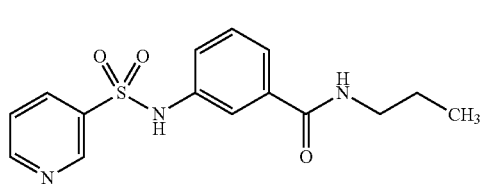

Compound 32 (FX2149) was synthesized using the general synthetic procedures for compounds 1-42 (x %): $^1$H NMR (400 MHz, CDCl$_3$) δ 0.94-0.98 (t, J=7.2 Hz, 3H), 1.59-1.65 (m, 2H), 3.43-3.48 (q, J=6.4 Hz, 2H), 6.37 (br s, 1H), 7.28-7.40 (m, 3H), 7.54-7.56 (d, J=7.2 Hz, 1H), 7.75 (s, 1H), 8.09-8.11 (d, J=8.0 Hz, 1H), 8.70 (s, 1H), 9.00 (s, 1H), 9.14 (s, 1H); $^{13}$C NMR (100 MHz, CDCl$_3$) δ 11.4, 22.8, 42.0, 121.1, 122.5, 123.9, 124.0, 129.6, 135.5, 135.7, 137.4, 147.3, 152.4, 166.8; MS (ESI) m/z=[M+H]+.

N-isopropyl-3-(pyridine-3-sulfonamido)benzamide Compound 33 (FX2151)

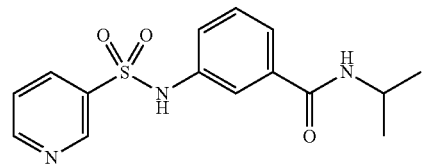

Compound 33 (FX2151) was synthesized using the general synthetic procedures for compounds 1-42 (x %): $^1$H NMR (400 MHz, CDCl$_3$) δ 1.20-1.30 (d, J=6.0 Hz, 6H), 4.30-4.50 (m, 1H), 6.10-6.20 (d, J=6.8 Hz, 1H), 7.20-7.30 (m, 3H), 7.50-7.60 (d, J=8.0 Hz, 1H), 7.78 (s, 1H), 8.00-8.10 (d, J=7.6 Hz, 1H), 8.60-8.70 (d, J=3.2 Hz, 1H), 8.96 (s, 1H), 9.40 (s, 1H); $^{13}$C NMR (100 MHz, CDCl$_3$) δ 22.8, 42.3, 121.1, 122.2, 123.6, 123.8, 129.5, 135.1, 135.5, 136.2, 137.7, 147.7, 153.0, 166.0; MS (ESI) m/z=[M+H]+.

N-isobutyl-3-(pyridine-3-sulfonamido)benzamide Compound 34 (FX2153)

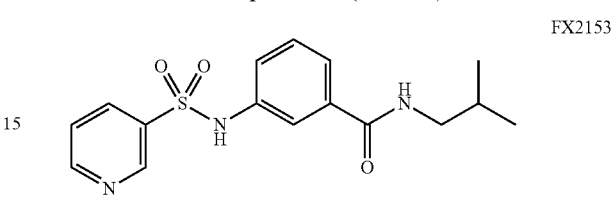

Compound 34 (FX2153) was synthesized using the general synthetic procedures for compounds 1-42 (x %): $^1$H NMR (400 MHz, CDCl$_3$) δ 0.90-1.00 (d, J=6.0 Hz, 6H), 1.80-2.00 (m, 1H), 3.30-3.40 (t, J=6.4 Hz, 2H), 6.45 (s, 1H), 7.20-7.40 (m, 3H), 7.50-7.60 (d, J=7.6 Hz, 1H), 7.75 (s, 1H), 8.03-8.09 (d, J=8.0 Hz, 1H), 8.60-8.70 (d, J=3.2 Hz, 1H), 8.97 (s, 1H), 9.29 (s, 1H); $^{13}$C NMR (100 MHz, CDCl$_3$) δ 20.1, 28.6, 47.4, 121.1, 122.3, 123.7, 123.9, 129.6, 135.2, 135.5, 136.2, 137.6, 147.7, 152.8, 166.9; MS (ESI) m/z=[M+H]+.

N-cyclopropyl-3-(pyridine-3-sulfonamido)benzamide Compound 35 (FX2155)

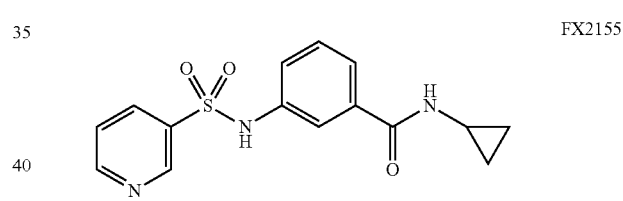

Compound 35 (FX2155) was synthesized using the general synthetic procedures for compounds 1-42 (x %): $^1$H NMR (400 MHz, CDCl$_3$) δ 0.50-0.60 (m, 2H), 0.80-0.90 (m, 2H), 2.90-3.00 (m, 1H), 6.71 (s, 1H), 7.20-7.30 (m, 1H), 7.30-7.40 (m, 2H), 7.40-7.60 (d, J=7.6 Hz, 1H), 7.74 (s, 1H), 8.02-8.09 (d, J=8.0 Hz, 1H), 8.60-8.70 (d, J=3.2 Hz, 1H), 8.96 (s, 1H), 9.34 (s, 1H); $^{13}$C NMR (100 MHz, CDCl$_3$) δ 6.7, 23.4, 121.0, 122.7, 123.9, 124.1, 129.5, 135.1, 135.2, 136.2, 137.5, 147.7, 152.9, 168.4; MS (ESI) m/z=[M+H]+.

N-(4-methoxybenzyl)-3-(pyridine-3-sulfonamido)benzamide Compound 36 (FX2157)

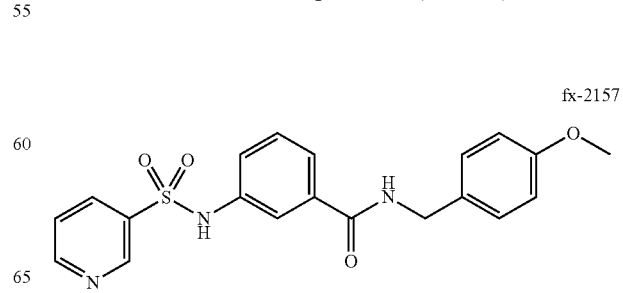

Compound 36 (FX2157) was synthesized using the general synthetic procedures for compounds 1-42 (x %): $^1$H NMR (400 MHz, DMSO-d$_6$) δ 3.72 (s, 3H), 4.35-4.40 (d, J=6.4 Hz, 2H), 6.86-6.88 (d, J=8.4 Hz, 2H), 7.20-7.30 (m, 3H), 7.31-7.40 (m, 1H), 7.50-7.64 (m, 3H), 8.10-8.15 (d, J=8.4 Hz, 1H), 8.77-8.79 (d, J=4.0 Hz, 1H), 8.85 (s, 1H), 8.95-8.97 (br s, 1H), 10.66 (s, 1H); $^{13}$C NMR (100 MHz, DMSO-d$_6$) δ 42.5, 55.5, 114.1, 120.4, 123.5, 124.9, 129.0, 129.8, 131.9, 135.1, 136.1, 137.7, 147.5, 154.1, 158.6, 165.8; MS (ESI) m/z=[M+H]+.

3-(pyridine-3-sulfonamido)-N-(3,3,3-trifluoropropyl)benzamide Compound 41 (FX3075)

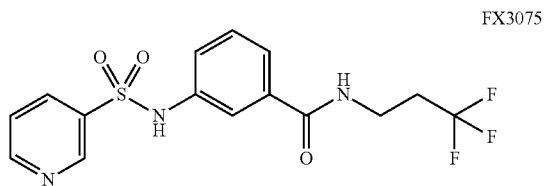 [SMILES: O=C(NCCC(F)(F)F)c1cccc(NS(=O)(=O)c2cccnc2)c1]

FX3075

Compound 41 (FX3075) was synthesized using the general synthetic procedures for compounds 1-42 (x %): $^1$H NMR (400 MHz, CDCl$_3$) δ 9.00 (s, 1H), 8.94 (s, 1H), 8.73 (s, 1H), 8.12-8.10 (d, J=8.4 Hz, 1H), 7.71 (s, 1H), 7.55-7.53 (d, J=7.6 Hz, 1H), 7.41 (m, 2H), 7.36-7.34 (m, 1H), 6.76 (s, 1H), 3.77-3.76 (d, J=5.6 Hz, 2H), 2.52-2.48 (m, 2H). $^{13}$C NMR (100 MHz, CDCl$_3$) δ 167.0, 152.6, 147.3, 137.2, 136.3, 135.7, 134.8, 129.9, 124.2, 124.1, 123.0, 120.8, 33.7.

N-(2,2,3,3,3-pentafluoropropyl)-3-(pyridine-3-sulfonamido)benzamide Compound 42 (FX3076)

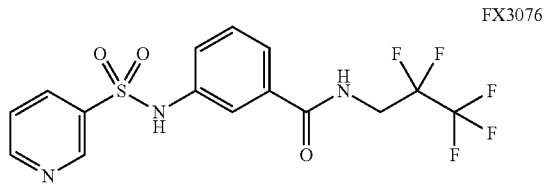 [SMILES: O=C(NCC(F)(F)C(F)(F)F)c1cccc(NS(=O)(=O)c2cccnc2)c1]

FX3076

Compound 42 (FX3076) was synthesized using the general synthetic procedures for compounds 1-42 (x %): $^1$H NMR (400 MHz, CDCl$_3$) δ 9.00 (s, 1H), 8.78-8.73 (m, 2H), 8.14-8.12 (d, J=8.4 Hz, 1H), 7.85-7.77 (m, 1H), 7.65 (s, 1H), 7.51-7.45 (m, 4H), 7.36-7.32 (m, 1H), 6.91 (s, 1H), 4.23-4.15 (m, 2H). $^{13}$C NMR (100 MHz, CDCl$_3$) δ 167.2, 152.2, 147.1, 137.0, 136.4, 136.2, 134.3, 130.0, 127.5, 127.0, 125.0, 124.4, 123.9, 120.8, 111.6, 39.2.

Example 3

A Novel GTP-Binding Inhibitor, FX2149, Attenuates LRRK2 Toxicity in Parkinson's Disease Models The additional inhibitor FX2149 is set forth herein and tested as a molecule aimed at increasing the in vivo efficacy of the compounds of the invention with improved brain penetration. Pharmacological characterization of FX2149 exhibited inhibition of LRRK2 GTP binding activity by ~90% at a concentration of 10 nM using in vitro assays. FX2149 also protected against mutant LRRK2-induced neurodegeneration in SH-SY5Y cells at 50-200 nM concentrations. Importantly, FX2149 at 10 mg/kg (i.p.) showed significant brain inhibition efficacy equivalent to that of 68 at 20 mg/kg (i.p.), determined by mouse brain LRRK2 GTP binding and phosphorylation assays. Furthermore, FX2149 at 10 mg/kg (i.p.) attenuated lipopolysaccharide (LPS)-induced microglia activation and LRRK2 upregulation in a mouse neuroinflammation model comparable to 68 at 20 mg/kg (i.p.). Our results highlight a novel GTP binding inhibitor with better brain efficacy, which represents a new lead compound for further understanding PD pathogenesis and therapeutic studies.

One of the challenges in developing therapeutics for neurodegenerative disorder is to improve both specific bioactive potency and blood-brain barrier penetration (BBB) simultaneously. Compound 68 is a potent inhibitor of LRRK2 GTP binding activity in vitro, with inhibitory activity in the low nanomolar range. However, 68 displays limited BBB permeability that attenuates the application of such inhibitors in animal models. Provided herein is the design and synthesis of an additional analog of 68, compound FX2149, which not only maintained the inhibition of LRRK2 GTP binding and kinase activities, but also showed improved in vivo efficacy due to its enhanced BBB permeability. We further characterized the pharmacological effects of FX2149 using in vitro and in vivo PD models. Our studies provided a novel LRRK2 GTP binding inhibitor, FX2149, with a more efficient brain efficacy for future pathogenesis and therapeutic studies.

Materials and Methods

Materials, Reagents, and Animals:

Anti-Flag antibodies were from Sigma (St. Louis, Mo., USA). Anti-LRRK2 and anti-phospho-LRRK2 antibodies were from Michael J. Fox Foundation. Anti-isolectin B4, anti-4E-BP, anti-phospho-4E-BP and anti-tyrosine hydroxylase (TH) were from Cell Signaling Technology (Beverly, Mass., USA). Compound 68 was custom ordered from Chembridge. LipofectAMINE Plus reagent and cell culture media were from Invitrogen (Carlsbad, Calif.). Compounds FX2149, FX2151, and 68 were dissolved in 0.1% DMSO/water solution for in vitro biochemistry and cell culture experiments. FX2149 and 68 were dissolved in 10% DMSO/0.9% saline for in vivo testing using mouse models. Wild type and G2019S-LRRK2-BAC transgenic mice were ordered from Jackson Laboratory and maintained in the animal facility at University of Maryland School of Pharmacy, and the animal procedure protocol was approved by the Animal Use and Care Committee of University of Maryland.

An Exemplary Synthesis of FX2149.

3-(Pyridine-3-sulfonamido)benzoic acid, 4 was synthesized as shown in the following steps. To a solution of ethyl 3-aminobenzoate methanesulfonate (1, 2.80 g, 11 mmol) in THF (30 mL) was added pyridine-3-sulfonyl chloride, 2 (1.77 g, 10 mmol), followed by triethylamine (2.1 mL, 15 mmol). The reaction mixture was allowed to stir at room temperature for 24 h and then concentrated. The crude product was purified with flash chromatography (EtOAc:hexanes, 1:4-1:1) to give ethyl 3-(pyridine-3-sulfonamido)benzoate, 3, as a white solid (2.8 g, 9.2 mmol, 92%). The resulting compound 3 was dissolved in methanol (30 mL). To this solution was added NaOH (1 N, 10 mL) drop wise. The reaction mixture was allowed to stir at 60° C. for 16 h and then cooled to room temperature. Methanol was removed by rotary evaporation, and the resulting bright yellow solution was acidified to pH 2 using HCl (4 N). Filtration under vacuum gave a white solid, which was further washed by HCl (1 N, 3×15 mL) to yield 3-(pyridine-3-sulfonamido)benzoic acid, 4, as a white solid (2.45 g, 8.8 mmol, 88% for two steps): $^1$H NMR (400 MH$_z$, DMSO-d$_6$) δ 7.37-7.41 (m, 2H), 7.55-7.67 (m, 2H), 7.68 (s, 1H), 8.10-8.12 (d, J=7.6 Hz, 1H), 8.77-8.78 (d, J=4.0 Hz, 1H), 8.87-8.88 (d, J=4.0 Hz, 1H), 10.20-11.20 (br s, 1H), 12.50-13.50 (br$^s$, 1H); $^{13}$C NMR (100 MH$_z$, DMSO-d$_6$) δ 121.4, 124.9, 125.0, 125.9, 130.2, 132.3, 135.1, 136.0, 137.8, 147.4, 154.1, 167.0; LC-MS (M-H$^+$) calculated for $C_{12}H_{10}N_2O_4S$, 277. found 277.

N-Propyl-3-(pyridine-3-sulfonamido)benzamide (FX2149) was synthesized as following steps. To a mixture of carboxylic acid, 4 (556 mg, 2.0 mmol), EDC (575 mg, 3.0 mmol), and HOBt (460 mg, 3.0 mmol) was added N,N-dimethylformamide (DMF, 8.0 mL), followed by propylamine (200 μL, 2.4 mmol). The reaction mixture was heated at 40° C. for 24 h. DMF was removed by rotary evaporation. To the resulting residue was added H$_2$O (10 mL) to give a white slurry. Filtration under vacuum gave a white solid, which was further washed using H$_2$O (4×10 mL). The product was further purified by recrystallization using CH$_2$Cl$_2$/hexanes give N-propyl-3-(pyridine-3-sulfonamido)benzamide (FX2149) as a white solid (515 mg, 1.61 mmol, 81%): $^1$H NMR (400 MHz, CDCl$_3$) δ 0.94-0.98 (t, J=7.2 Hz, 3H), 1.59-1.65 (m, 2H), 3.43-3.48 (q, J=6.4 Hz, 2H), 6.37 (br s, 1H), 7.28-7.40 (m, 3H), 7.54-7.56 (d, J=7.2 Hz, 1H), 7.75 (s, 1H), 8.09-8.11 (d, J=8.0 Hz, 1H), 8.70 (s, 1H), 9.00 (s, 1H), 9.14 (s, 1H); $^{13}$C NMR (100 MHz, CDCl$_3$) δ 11.4, 22.8, 42.0, 121.1, 122.5, 123.9, 124.0, 129.6, 135.5, 135.7, 137.4, 147.3, 152.4, 166.8; LC-MS (M+H$^+$) calculated for $C_{15}H_{18}N_3O_3S$, 320. found 320.

Cell Culture, LRRK2 Constructs, and Transfection:

Human embryonic kidney HEK293T and human neuroblastoma SH-SY5Y cells were from ATCC (Manassas, Va., USA) and grown in media. The Flag tagged wild type, G2019S, R1441C, Y1699C, and G2019S-K1347A constructs were utilized. Transient transfections were performed using Lipofectamine™ and PLUS™ Reagents (Invitrogen) according to the manufacturer's protocol.

Immunoprecipitation (IP) and Western Blot Analysis:

IP was performed using anti-FLAG-agarose (Sigma) as described previously. For Western blot analysis, the resulting immunoprecipitates or cell lysates were run with 4-12% NuPAGE Bis-Tris gels and transferred onto polyvinylidene difluoride membranes (Invitrogen). The membranes were blocked with 5% nonfat milk and then incubated with various primary antibodies followed by secondary antibody detection as described previously. Enhanced chemiluminescence (ECL) reagents were used to detect proteins on the membranes.

LRRK2 GTP Binding and Phosphorylation (Kinase) Assays:

GTP binding assays were performed using GTP-agarose beads (Sigma) as described previously. Lysates of HEK 293T cells expressing LRRK2 proteins were incubated with 68 or FX2149 at various concentrations for 1 h. The GTP-agarose beads were added for an additional 2 h. The samples were subjected to Western blot analysis using anti-Flag antibodies. LRRK2 kinase assays were performed using LRRK2 phosphorylation and in vitro $^{32}$P incorporation methods as described previously.

For LRRK2 phosphorylation assays, HEK293T cells were transfected with various LRRK2 variants for 36 h, then were incubated in media without serum for 12 hours. The cells were left untreated or treated with 68, or FX2149 for 1 h, and then were harvested with lysis buffer (Cell Signaling). The resulting cell lysates were immunoprecipitated using anti-Flag antibodies to pull down Flag-tagged LRRK2. The immunoprecipitates were subjected to Western blot using anti-phospho-LRRK2 antibodies (S2032 or 5935) as described previously. In vitro $^{32}$P incorporation was performed using purified LRRK2 that were left untreated or treated with 68 or FX2149 for 1 h. The samples were then incubated with the kinase reaction buffer containing 500 μM ATP and 10 μCi of [γ-$^{32}$P]ATP (3,000 Ci/mmol) for 30 min. The LRRK2 autophosphorylation with $^{32}$P incorporation was separated by SDS/PAGE gel and quantified with a phosphoimager (Bio-Rad Molecular Imager).

LRRK2 Toxicity Assays:

SH-SY5Y cell viability assays were conducted as described. Cells were co-transfected with GFP and various pcDNA3.1-LRRK2 plasmids at a 1:15 ratio for 24 h in 10% FBS OPTI-I media and then changed to DMEM with N2 supplement for 24 h. Compounds were added after 4-h transfection. Cell viability was measured by counting the healthy viable cells that contained at least one smooth extension (neurite) that was twice the length of the cell body from 20 randomly selected fields using fluorescence microscopy. TUNEL assays were performed according to the manufacturer's instructions as described previously. The experiments were repeated three times in duplicate. The quantification for LRRK2 toxicity was performed by an investigator who was blind to transfection groups.

LPS-Based Preinflammatory Mouse Model and Immunohistochemical Analysis:

G2019S-LRRK2-BAC transgenic mice were anesthetized with isoflurane and injected with LPS (15,000 endotoxin units, 5 μg, Sigma) for each mouse in the substantia nigra pars compacta (SN) unilaterally as described previously. The brain coordinates for injection of LPS were −1.1 mediolateral (ML), −3.4 anteroposterior (AP), and −3.9 dorsoventral (DV) related to bregma. FX2149 and 68 were injected i.p. 1 hour prior to LPS injection at doses of 0, 10, or 20 mg/kg. FX2149 and 68 were then injected (i.p.) twice daily for three days. Brain tissues were harvested with 4% paraformaldehyde (PFA) perfusion. The frozen brain sections through the SN at 30 μm were subjected to immunohistochemical analysis. Brain sections were incubated with various primary antibodies including anti-isolectin B4, anti-phosphorylated LRRK2 S935, anti-LRRK2, and anti-TH (Milipore) antibodies. Then the sections were incubated with fluorescent secondary antibodies including Alexa Fluor 568 goat anti-mouse (rabbit) IgG (Invitrogen) and Alexa Fluor 488 goat anti-mouse (rabbit) IgG. Some sections were added with anti-rabbit (mouse) biotinylated secondary antibody and avidin-biotin-peroxidase complex (Vector Laboratories), and detected by diaminobenzidine (DAB, Sigma). The images of brain sections were taken using a Zeiss Axioskop 2 microscope and a Zeiss Axiocam camera, and processed using Adobe Photoshop (VII) software. The continuing middle brain section series from each mouse brain were sampled by 6 section intervals for fluorescent density quantification of the SN areas. The quantification of fluorescence density was performed by unbiased stereology with an investigator who was blind to experiment groups.

Data Analysis:

Quantitative data were shown as arithmetic means±SEM from three separate experiments. Statistically significant differences among groups were analyzed by ANOVA using Sigmastart 3.1 statistical software (Aspire Software International, VA). A p value <0.05 was considered significant.

Results

Design and Synthesis of FX2149

Given that 68 potently inhibits LRRK2 GTP binding and kinase activity in vitro, we conserved its scaffold structure to retain the inhibition of GTP binding and kinase activity. For certain instances, compound with good BBB permeability may require a Log P value between 1.0 and 3.0 and a Log BB value between −2.0 and 1.0. To optimize the BBB permeability of 68, we used a pyridine-3-sulfonamide group to replace the phenyl-sulfonamide head of 68 (FIG. 1). Weakly basic groups, such as the pyridinyl group, are commonly present in therapeutic agents targeting the central nervous system. Moreover, the 2-methoxy-ethyl tail of 68 was substituted by a propyl group to reduce the number of H-bond acceptors to fit the binding site of the LRRK2 GTPase domain. Compound FX2149 was calculated to have increased hydrophilicity (Log P=1.38 vs 2.05 for 68) and enhanced BBB permeability (Log BB=−0.21 vs −0.27 for 68, calculated by using ACD/Labs Suite 5.0).

The synthesis of compound FX2149 involved a three-step procedure. First, ethyl 3-aminobenzoate methanesulfonate, 1, was treated with pyridine-3-sulfonyl chloride, 2, in the presence of triethylamine ($Et_3N$) at room temperature to generate compound 3 as a mixture of rotamers in excellent yields. Next, saponification of ethylester in compound 3 using aqueous NaOH yielded carboxylic acid, 4, in high yields. Finally, compound 4 was coupled with propylamine using N-ethyl-N'-(3-dimethylaminopropyl) carbodiimide hydrochloride (EDC) and 1-hydroxybenzotriazole hydrate (HOBt) to provide FX2149 in high yields. Compound FX2149 was purified by flash chromatography with over 95% purity.

FX2149 Reduced LRRK2 Binding with GTP

To evaluate the effects of FX2149 on LRRK2 GTP binding activity, a GTP binding assay was employed using GTP-agarose. GTP-agarose pulled down LRRK2 from the lysates of HEK293T cells expressing human LRRK2. Incubation of FX2149 with GTP-agarose significantly reduced LRRK2 binding with GTP (FIGS. 23 and 24). FX2149 at 10 nM concentration reduced LRRK2 GTP-binding activity by ~90% (FIG. 23). Similar to the effects of 68, FX2149 reduced the PD-linked mutant LRRK2 variants (G2019S and R1441C) that bound with GTP (FIGS. 25 and 26).

FX2149 Reduced LRRK2 Kinase Activity

Figure 27:
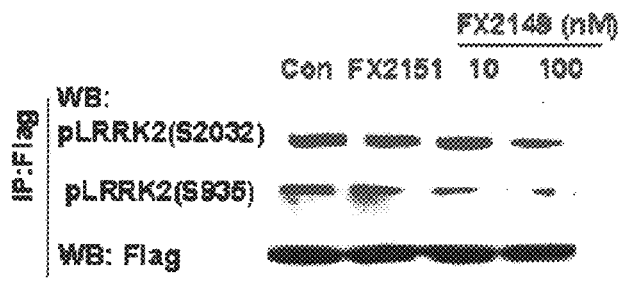
FIGS. 27 to 29 demonstrate certain aspects of a study indicating that compound FX2149 reduces LRRK2 kinase activity (phosphorylation).
Figure 28:
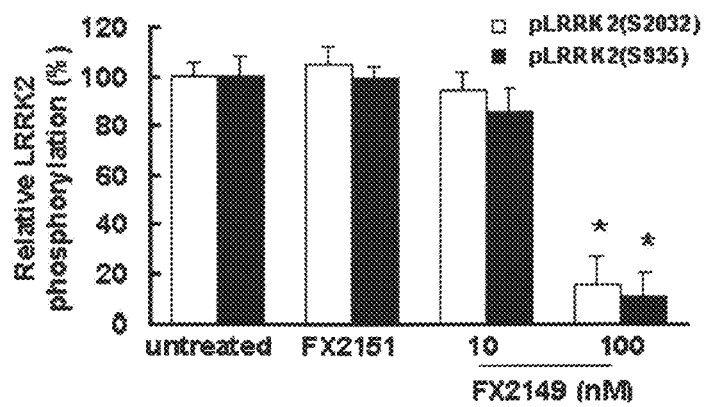
Figure 29:
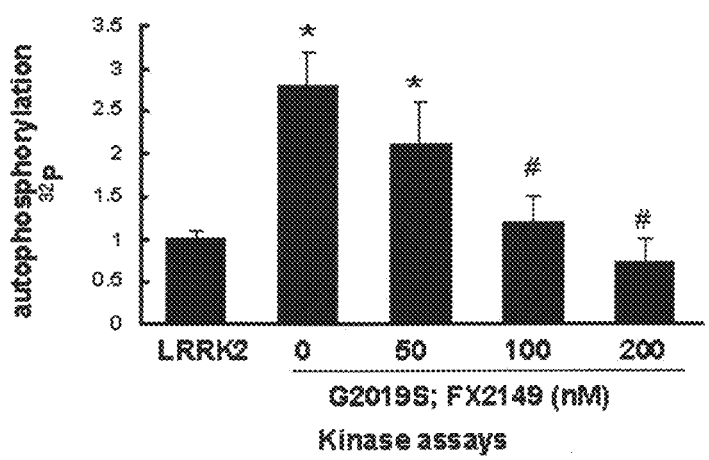

To further assess whether FX2149 alters LRRK2 phosphorylation (kinase activity), HEK293T cells expressing mutant G2019S-LRRK2 were treated with FX2149 at concentrations of 0, 10, and 100 nM for 1 h. Cell lysates were subject to LRRK2 autophosphorylation (kinase activity) assays. FX2149 at 100 nM concentration significantly reduced G2019S-LRRK2 phosphorylation at residues S935 and S2032 by ~90% (FIGS. 27 and 28). We further validated these results by in vitro kinase assays showing the similar inhibition of G2019S-LRRK2 kinase activity by FX2149 (FIG. 29). These findings indicated that FX2149 (100 nM) reduced LRRK2 kinase activity similar to that of 68 at 10 nM concentration. An inactive analog of 68, FX2151, did not alter the LRRK2 phosphorylation at 10 µM concentration.

FX2149 Attenuated Mutant LRRK2-Induced Toxicity in SH-SY5Y Cells

Figure 30:
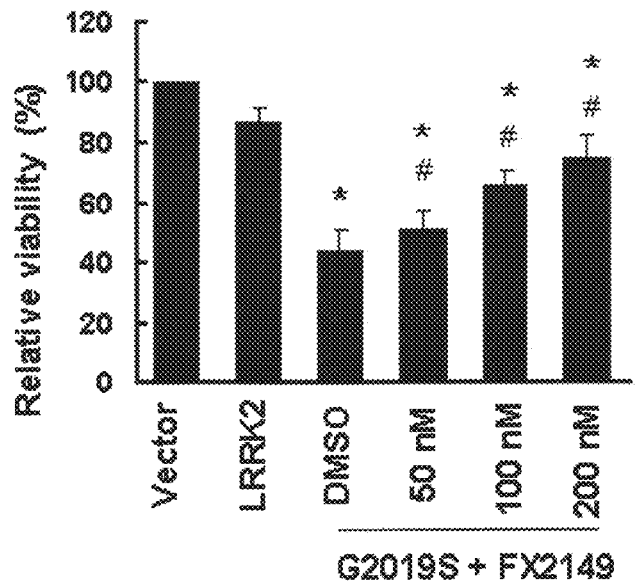
FIGS. 30 and 31 graphically demonstrate certain aspects of a study indicating that compound FX2149 attenuates G2019S-LRRK2-induced neuronal degeneration in SH-SY5Y cells, in which SH-SY5Y cells were co-transfected with GFP and various pcDNA3.1-LRRK2 plasmids at a 1:15 ratio as described in the method section. After 4-h transfection, cells were treated with FX2149 for 48 hours.
Figure 31:
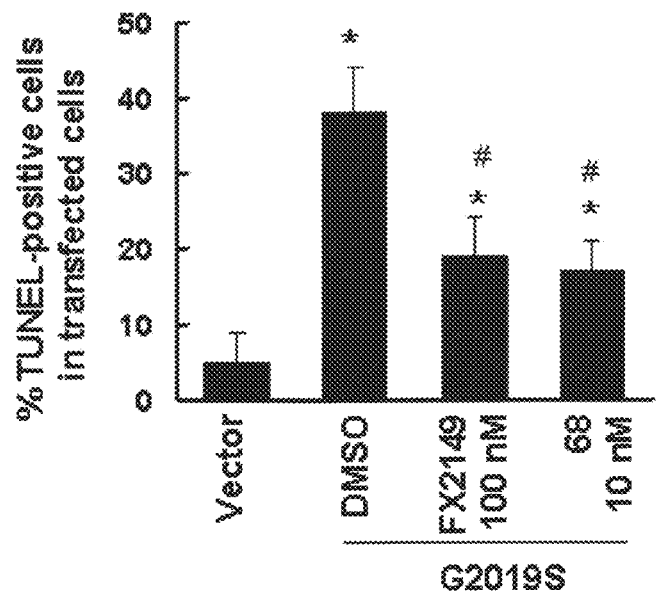

GTP binding activity and elevated kinase activities have been implicated in PD-linked mutant, G2019S-LRRK2, resulting in neurodegeneration. SH-SY5Y cells contain dopamine and are often used as a PD cell model. To assess whether FX2149 alters mutant LRRK2-induced neuronal degeneration, G2019S-LRRK2 construct transiently transfected into SH-SY5Y cells was used as a toxicity model. Treatment of FX2149 significantly increased the viability of cells expressing G2019S-LRRK2 compared with vehicle treated cells (FIG. 30). Moreover, FX2149 at 100 nM significantly reduced the TUNEL-positive cells expressing mutant G2019S-LRRK2 and had effects equivalent to that of 68 at 10 nM (FIG. 31).

FX2149 was More Efficient in Reducing LRRK2 GTP Binding and Kinase Activities in Transgenic Mice Brains than 68

Figure 32:
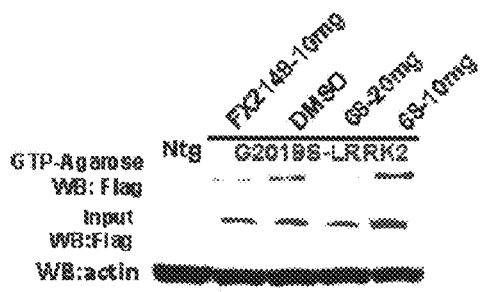
FIGS. 32 to 37 demonstrate certain aspects of a study indicating that FX2149 displays improved brain penetration as compared to 68 in view of LRRK2 GTP binding and kinase activities, in which FX2149 (10 mg/kg) and 68 (10 and 20 mg/kg) were injected intraperitoneally into G2019S-LRRK2 BAC transgenic mice at 6-12 weeks of age for 1 hour. There were 6 mice in each experimental group. The brain homogenates were used to detect LRRK2 GTP-binding and kinase activities.
Figure 34:
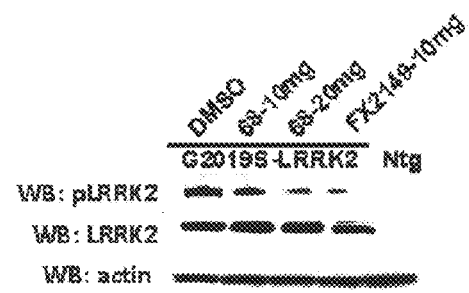
Figure 33:
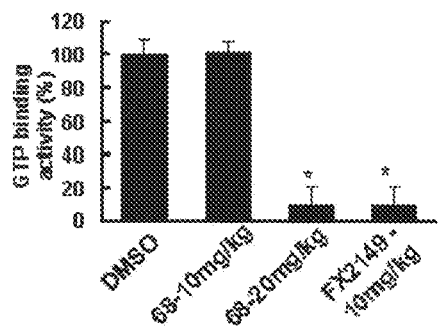
Figure 35:
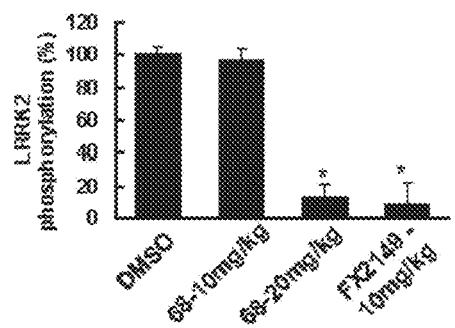
Figure 36:
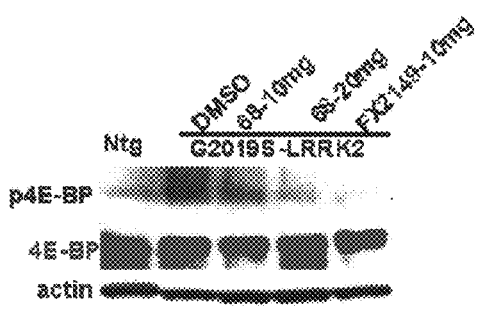
Figure 37:
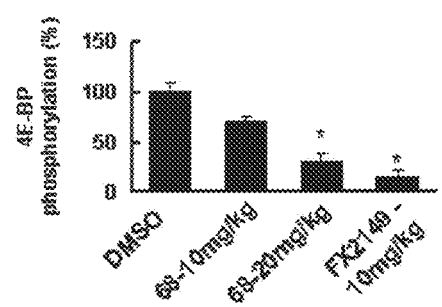

To assess the effects of FX2149 on LRRK2 in brains compared with 68, both 68 and FX2149 were injected intraperitoneally into G2019S-BAC-LRRK2 transgenic mice at 10 and 20 mg/kg doses. One hour after the injection, the mouse brain homogenates were subjected to LRRK2 GTP binding and kinase assays. Both 68 (20 mg/kg) and FX2149 (10 mg/kg) reduced LRRK2 GTP binding activity in mouse brains (FIGS. 32 and 33). While FX2149 at a 10 mg/kg dose had the equivalent GTP binding inhibition as 68 at a 20 mg/kg dose, compound 68 at 10 mg/kg dose did not alter brain GTP binding activity 1 h after injection. Moreover, both 68 (20 mg/kg) and FX2149 (10 mg/kg) also significantly reduced brain LRRK2 kinase activity (FIGS. 34 and 35). To further confirm the effect of FX2149, we also assessed a LRRK2 downstream effector, 4E-BP phosphorylation. 4E-BP is a transcription factor that can be phosphorylated by LRRK2. We found that both 68 and FX2149 reduced 4E-BP phosphorylation in mouse brains (FIGS. 36 and 37). FX2149 at a 10 mg/kg dose reduced 4E-BP up to 15% of the untreated control group, while 68 at a 20 mg/kg dose reduced 4E-BP up to 15% of the untreated control group. These data indicated that FX2149 was taken up into brains at a greater extent and had more potent efficacy in inhibiting GTP binding and kinase activity in mouse brains when compared with 68.

FX2149 Reduced LPS-Induced Microglia Activation and LRRK2 Upregulation in Mice.

Figure 38:
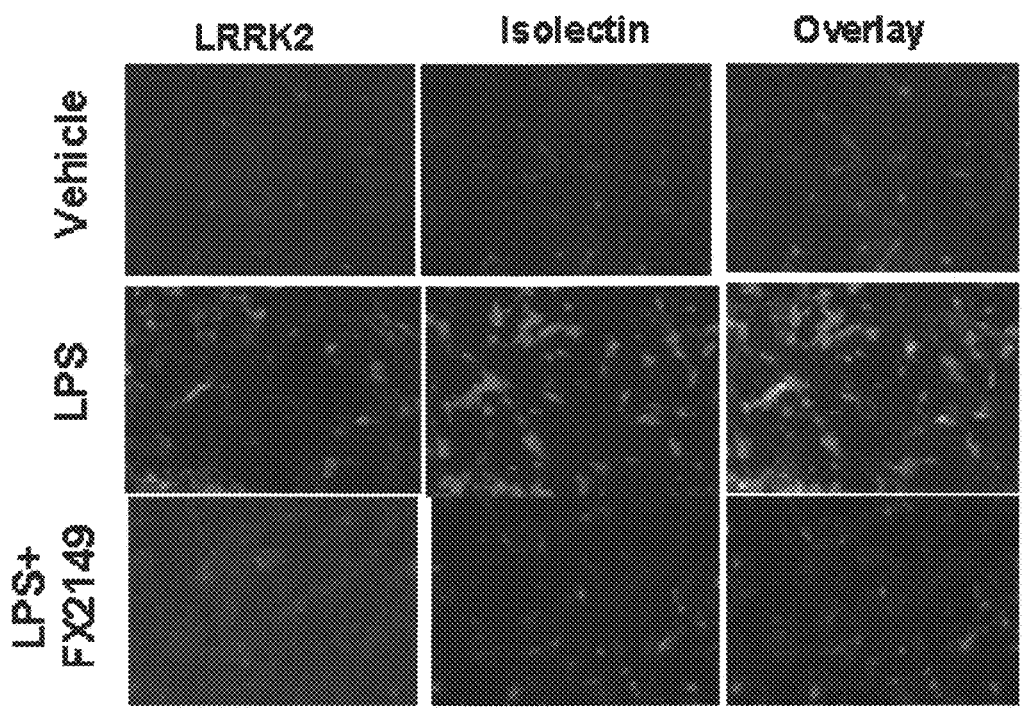
FIGS. 38 to 40 demonstrate certain aspects of a study indicating that FX2149 reduced LPS-induced microglia activation and LRRK2-upregulation, in which G2019S-LRRK2 BAC transgenic mice (6-12 weeks) were injected with LPS (5 μg) and FX2149 (10 mg/kg) as described in the methods section. Serial coronal sections through the substantia nigra were subjected to immunohistochemistry analysis.
Figure 39:
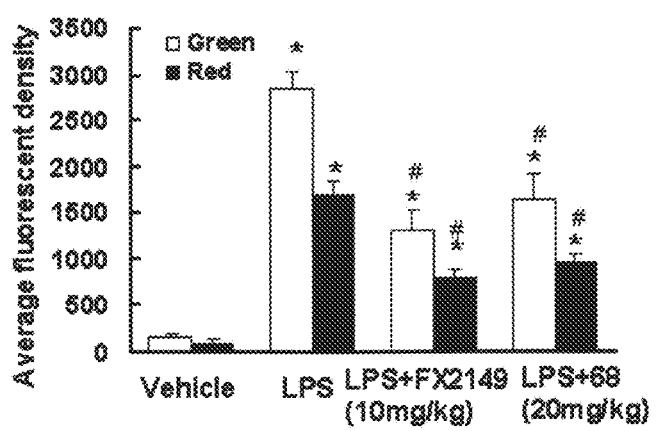
Figure 40:
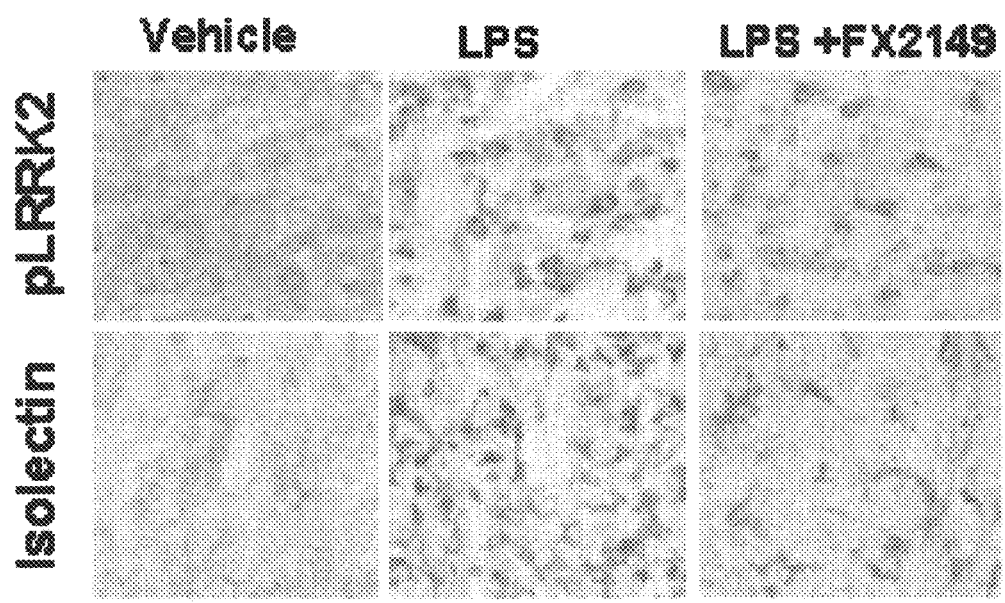

To further characterize the pharmacological effects of FX2149 in brains, a LPS-based mouse neuroinflammation model was used as described previously. Injection of LPS resulted in significant increases in LRRK2 expression, phosphorylation, and microglial activation in the substantia nigra compared with vehicle controls (FIGS. 38-40). Treatment of mice with FX2149 significantly reduced LPS-induced LRRK2-positive immunostaining compared with vehicle controls, but it did not alter LRRK2 cytoplasmic localization. Moreover, the anti-phosphoryated-LRRK2 immunoactivity was also significantly reduced in the FX2149 treated group. As in our previous study of 68 at 20 mg/kg, FX2149 at a 10 mg/kg dose significantly reduced LPS-induced isolectin B4 (microglia marker) positive immunostaining in the substantia nigra. There was a ~43% isolectin B4 immunoactivity in the FX2149 treated group compared with the LPS alone treated group. In comparison, the immunoactivity of isolectin B4 in the 68 treated group (20 mg/kg) was ~56% (FIG. 39). Consistent with previous findings, anti-TH (dopaminergic neuron marker) immunostaining in the subtantia nigra did not change among various treatment groups and the control group, indicating that LPS treatment did not alter dopaminergic neuron degeneration in this acute inflammation condition.

Discussion

We have identified and characterized a LRRK2 GTP binding inhibitor, 68. To improve in vivo effects of 68, we designed and synthesized an analog of 68, compound FX2149, to improve brain permeability. The in vitro biological characterization of FX2149 demonstrated that it inhibited LRRK2 GTP binding and kinase activity, and protected against mutant LRRK2 toxicity at 10-100 nM concentrations. FX2149 showed increased in vivo efficacy, with a more than 2-fold improvement over 68. FX2149 significantly reduced LPS-induced microglia activation and LRRK2 upregulation at a significantly lower dose than 68. These findings demonstrated that FX2149 is a better lead GTP binding inhibitor with improved brain penetration for future drug development and pathogenesis studies.

The major pathology area of PD is in the substantia nigra. Consequently, for therapeutic agents to prevent neurodegeneration, they must cross the BBB. Most neuroprotective compounds fail further development due to either a lack of high potency in brains or poor BBB permeability. Based on the chemical scaffold of 68, a new analog, FX2149, has been synthesized by substituting the phenylsulfonyl fragment of 68 with a pyridine-3-sulfonyl group, while replacing the methoxyethyl tail of 68 with a propyl tail. FX2149 has similar effects in inhibition of LRRK2 GTP binding activity compared with 68, although it has less potency than 68 in in vitro assays. FX2149 at 100 nM inhibited LRRK2 kinase activity equivalent to 68 at 10 nM by in vitro phosphorylation assays. However, FX2149 had a potent efficacy in inhibiting LRRK2 GTP binding and kinase activities by in vivo testing with the LRRK2 transgenic mouse model. FX2149 at 10 mg/kg had an approximately equivalent GTP binding and kinase inhibition effect as seen in 68 at 20 mg/kg. FX2149 at 10 mg/kg had a stronger effect in reducing mutant G2019S-induced 4E-BP phosphorylation compared with the treatment group of 68 at 20 mg/kg. 4E-BP is a stress-related transcription factor and increases in phosphorylation is believed to contribute to neuronal degeneration. Taken together, these results demonstrated that FX2149 had better brain penetration efficacy for animal studies as required for PD intervention.

The loss of dopaminergic (DA) neurons in the substantia nigra is an early and key pathological hallmark of PD. Disruption of LRRK2 GTP binding by genetic mutation reduces LRRK2 kinase activity, thereby suppressing neuronal degeneration. Similar to the effects of 68, our results showed that compound FX2149 reduced LRRK2 GTP binding and kinase activities, and significantly attenuated mutant LRRK2-induced neuron degeneration in in vitro cell culture models. Another feature of neurodegeneration is microglia activation and inflammation in brains. Microglia activation releases various inflammatory cytokines which trigger or facilitate dopaminergic neuronal loss in PD. The preinflammatory agent, LPS, elevates LRRK2 expression and phosphorylation in activated microglia in mice. Our results showed that FX2149 at 10 mg/kg significantly reduced LPS-induced microglia activation by 57% compared with the vehicle treated LPS mice group. In comparison, 68 at 20 mg/kg only reduced LPS-induced microglia by 44% (FIG. 34). These results further validated the significantly improved in vivo effects of FX2149 compared to 68 in the LPS-based animal model.

In summary, these studies provided an additional GTP binding inhibitor, FX2149 (analog of 68), and further proved that GTP binding regulates LRRK2 kinase activity. Disruption of GTP binding activity may be an effective strategy to prevent neuron degeneration for PD and other LRRK2-related disorders.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, and methods described herein that embody the present invention can, in alternate embodiments, be more specifically defined by any of the transitional terms "comprising," "consisting essentially of," and "consisting of."

REFERENCES

1. Geldenhuys, W. J., Van der Schyf, C. J. (2013) Rationally designed multi-targeted agents against neurodegenerative diseases. Curr. Med. Chem., 20, 1662-72
2. Deng, X., Choi, H. G., Buhrlage, S. J., Gray, N. S. (2012) Leucine-rich repeat kinase 2 inhibitors: a patent review (2006-2011). Expert. Opin. Ther. Pat., 22, 1415-1426.
3. Paisan-Ruiz, C., Jain, S., Evans, E. W., Gilks, W. P., Simon, J., van der, B. M., Lopez, d. M., Aparicio, S., Gil, A. M., Khan, N., et al. (2004) Cloning of the gene containing mutations that cause PARK8-linked Parkinson's disease. Neuron, 44, 595-600.
4. Zimprich, A., Biskup, S., Leitner, P., Lichtner, P., Farrer, M., Lincoln, S., Kachergus, J., Hulihan, M., Uitti, R. J., Calne, D. B., et al. (2004) Mutations in LRRK2 cause autosomal-dominant parkinsonism with pleomorphic pathology. Neuron, 44, 601-607.
5. Moore, D. J. (2008) The biology and pathobiology of LRRK2: implications for Parkinson's disease. Parkinsonism. Relat. Disord., 14 Suppl 2, S92-S98.
6. Gandhi, P. N., Chen, S. G., Wilson-Delfosse, A. L. (2009) Leucine-rich repeat kinase 2 (LRRK2): a key player in the pathogenesis of Parkinson's disease. J. Neurosci. Res., 87, 1283-1295.

7. Giasson, B. I., Van, D., V M. (2008) Mutations in LRRK2 as a cause of Parkinson's disease. Neurosignals., 16, 99-105.
8. Biskup, S., West, A. B. (2009) Zeroing in on LRRK2-linked pathogenic mechanisms in Parkinson's disease. Biochim. Biophys. Acta, 1792, 625-633.
9. Kumari, U., Tan, E. K. (2009) LRRK2 in Parkinson's disease: genetic and clinical studies from patients. FEBS J., 276, 6455-6463.
10. Li, T., Yang, D., Sushchky, S., Liu, Z., Smith, W. W. (2011) Models for LRRK2-Linked Parkinsonism. Parkinsons. Dis., 2011, 942412.
11. Cookson, M. R. (2010) The role of leucine-rich repeat kinase 2 (LRRK2) in Parkinson's disease. Nat. Rev. Neurosci., 11, 791-797.
12. Lee, B. D., Dawson, V. L., Dawson, T. M. (2012) Leucine-rich repeat kinase 2 (LRRK2) as a potential therapeutic target in Parkinson's disease. Trends Pharmacol. Sci., 33, 365-373.
13. Tan, E. K., Schapira, A. H. (2010) LRRK2 as a therapeutic target in Parkinson's disease. Eur. J. Neurol., 18, 545-6
14. Liao, J., Wu, C. X., Burlak, C., Zhang, S., Sahm, H., Wang, M., Zhang, Z. Y., Vogel, K. W., Federici, M., Riddle, S. M., et al. (2014) Parkinson disease-associated mutation R1441H in LRRK2 prolongs the "active state" of its GTPase domain. Proc. Natl. Acad. Sci. U.S.A, 111, 4055-4060.
15. Deng, X., Dzamko, N., Prescott, A., Davies, P., Liu, Q., Yang, Q., Lee, J. D., Patricelli, M. P., Nomanbhoy, T. K., Alessi, D. R., Gray, N. S. (2011) Characterization of a selective inhibitor of the Parkinson's disease kinase LRRK2. Nat. Chem. Biol., 7, 203-205.
16. Lee, B. D., Shin, J. H., VanKampen, J., Petrucelli, L., West, A. B., Ko, H. S., Lee, Y. I., Maguire-Zeiss, K. A., Bowers, W. J., Federoff, H. J., et al. (2010) Inhibitors of leucine-rich repeat kinase-2 protect against models of Parkinson's disease. Nat. Med., 16, 998-1000.
17. Liu, Z., Hamamichi, S., Dae, L. B., Yang, D., Ray, A., Caldwell, G. A., Caldwell, K. A., Dawson, T. M., Smith, W. W., Dawson, V. L. (2011) Inhibitors of LRRK2 kinase attenuate neurodegeneration and Parkinson-like phenotypes in Caenorhabditis elegans and Drosophila Parkinson's disease models. Hum. Mol. Genet., 20, 3933-42.
18. Smith, W. W., Pei, Z., Jiang, H., Dawson, V. L., Dawson, T. M., Ross, C. A. (2006) Kinase activity of mutant LRRK2 mediates neuronal toxicity. Nat. Neurosci., 9, 1231-1233.
19. Lewis, P. A., Greggio, E., Beilina, A., Jain, S., Baker, A., Cookson, M. R. (2007) The R1441C mutation of LRRK2 disrupts GTP hydrolysis. Biochem. Biophys. Res. Commun, 357, 668-671.
20. Deng, J., Lewis, P. A., Greggio, E., Sluch, E., Beilina, A., Cookson, M. R. (2008) Structure of the ROC domain from the Parkinson's disease-associated leucine-rich repeat kinase 2 reveals a dimeric GTPase. Proc. Natl. Acad. Sci. U.S.A., 105, 1499-1504.
21. Webber, P. J., Smith, A. D., Sen, S., Renfrow, M. B., Mobley, J. A., West, A. B. (2011) Autophosphorylation in the Leucine-Rich Repeat Kinase 2 (LRRK2) GTPase Domain Modifies Kinase and GTP-Binding Activities. J. Mol. Biol., 412, 94-110
22. Liu, M., Dobson, B., Glicksman, M. A., Yue, Z., Stein, R. L. (2010) Kinetic mechanistic studies of wild-type leucine-rich repeat kinase 2: characterization of the kinase and GTPase activities. Biochemistry, 49, 2008-2017.
23. Liu, M., Poulose, S., Schuman, E., Zaitsev, A. D., Dobson, B., Auerbach, K., Seyb, K., Cuny, G. D., Glicksman, M. A., Stein, R. L., Yue, Z. (2010) Development of a mechanism-based high-throughput screen assay for leucine-rich repeat kinase 2—discovery of LRRK2 inhibitors. Anal. Biochem., 404, 186-192.
24. Biosa, A., Trancikova, A., Civiero, L., Glauser, L., Bubacco, L., Greggio, E., Moore, D. J. (2013) GTPase activity regulates kinase activity and cellular phenotypes of Parkinson's disease-associated LRRK2. Hum. Mol. Genet., 22, 1140-1156.
25. Xiong, Y., Coombes, C. E., Kilaru, A., Li, X., Gitler, A. D., Bowers, W. J., Dawson, V. L., Dawson, T. M., Moore, D. J. (2010) GTPase activity plays a key role in the pathobiology of LRRK2. PLoS. Genet., 6, e1000902.
26. Burkhard, K., Smith, S., Deshmukh, R., MacKerell, A. D., Jr., Shapiro, P. (2009) Development of extracellular signal-regulated kinase inhibitors. Curr. Top. Med. Chem., 9, 678-689.
27. Zhong, S., Chen, X., Zhu, X., Dziegielewska, B., Bachman, K. E., Ellenberger, T., Ballin, J. D., Wilson, G. M., Tomkinson, A. E., MacKerell, A. D., Jr. (2008) Identification and validation of human DNA ligase inhibitors using computer-aided drug design. J. Med. Chem., 51, 4553-4562.
28. Toschi, L., Donner, P., Pohlenz, H. D., Kreft, B., Weiss, B. (2006) LRRK1 protein kinase activity is stimulated upon binding of GTP to its Roc domain. Cell Signal., 18, 910-920.
29. Li, Y., Liu, W., Oo, T. F., Wang, L., Tang, Y., Jackson-Lewis, V., Zhou, C., Geghman, K., Bogdanov, M., Przedborski, S., et al. (2009) Mutant LRRK2(R1441G) BAC transgenic mice recapitulate cardinal features of Parkinson's disease. Nat. Neurosci., 12, 826-828.
30. Li, X., Patel, J. C., Wang, J., Avshalumov, M. V., Nicholson, C., Buxbaum, J. D., Elder, G. A., Rice, M. E., Yue, Z. (2010) Enhanced striatal dopamine transmission and motor performance with LRRK2 overexpression in mice is eliminated by familial Parkinson's disease mutation G2019S. J. Neurosci., 30, 1788-1797.
31. Barcia, C. (2013) Glial-mediated inflammation underlying parkinsonism. Scientifica. (Cairo.)., 2013, 357805.
32. Hamza, T. H., Zabetian, C. P., Tenesa, A., Laederach, A., Montimurro, J., Yearout, D., Kay, D. M., Doheny, K. F., Paschall, J., Pugh, E., et al. (2010) Common genetic variation in the HLA region is associated with late-onset sporadic Parkinson's disease. Nat. Genet., 42, 781-785.
33. Moehle, M. S., Webber, P. J., Tse, T., Sukar, N., Standaert, D. G., DeSilva, T. M., Cowell, R. M., West, A. B. (2012) LRRK2 inhibition attenuates microglial inflammatory responses. J. Neurosci., 32, 1602-1611.
34. Luerman, G. C., Nguyen, C., Samaroo, H., Loos, P., Xi, H., Hurtado-Lorenzo, A., Needle, E., Stephen, N. G., Galatsis, P., Dunlop, J., et al. (2013) Phosphoproteomic evaluation of pharmacological inhibition of leucine-rich repeat kinase 2 reveals significant off-target effects of LRRK-2-IN-1. J. Neurochem., 128, 561-76.
35. Hakimi, M., Selvanantham, T., Swinton, E., Padmore, R. F., Tong, Y., Kabbach, G., Venderova, K., Girardin, S. E., Bulman, D. E., Scherzer, C. R., et al. (2011) Parkinson's disease-linked LRRK2 is expressed in circulating and tissue immune cells and upregulated following recognition of microbial structures. J. Neural. Transm., 118, 795-808.
36. Dzamko, N., Inesta-Vaquera, F., Zhang, J., Xie, C., Cai, H., Arthur, S., Tan, L., Choi, H., Gray, N., Cohen, P., et al. (2012) The IkappaB Kinase Family Phosphorylates the Parkinson's Disease Kinase LRRK2 at Ser935 and Ser910 during Toll-Like Receptor Signaling. PLoS. One., 7, e39132.
37. Cardoso, C. C., Pereira, A. C., de Sales, M. C., Moraes, M. O. (2011) Leprosy susceptibility: genetic variations regulate innate and adaptive immunity, and disease outcome. Future. Microbiol., 6, 533-549.
38. Liu, Z., Lee, J., Krummey, S., Lu, W., Cai, H., Lenardo, M. J. (2011) The kinase LRRK2 is a regulator of the transcription factor NFAT that modulates the severity of inflammatory bowel disease. Nat. Immunol., 12, 1063-1070.
39. Gardet, A., Benita, Y., Li, C., Sands, B. E., Ballester, I., Stevens, C., Korzenik, J. R., Rioux, J. D., Daly, M. J., Xavier, R. J., Podolsky, D. K. (2010) LRRK2 is involved in the IFN-gamma response and host response to pathogens. J. Immunol., 185, 5577-5585.
40. Li, X., Wang, Q. J., Pan, N., Lee, S., Zhao, Y., Chait, B. T., Yue, Z. (2011) Correction: Phosphorylation-Dependent 14-3-3 Binding to LRRK2 Is Impaired by Common Mutations of Familial Parkinson's Disease. PLoS. One., 6, e17153.
41. Li, X., Moore, D. J., Xiong, Y., Dawson, T. M., Dawson, V. L. (2010) Reevaluation of phosphorylation sites in the Parkinson disease-associated leucine-rich repeat kinase 2. J. Biol. Chem., 285, 29569-29576.
42. Zhong, S., MacKerell, A. D., Jr. (2007) Binding response: a descriptor for selecting ligand binding site on protein surfaces. J. Chem. Inf. Model., 47, 2303-2315.
43. Pan, Y., Huang, N., Cho, S., MacKerell, A. D., Jr. (2003) Consideration of molecular weight during compound selection in virtual target-based database screening. J. Chem. Inf. Comput. Sci., 43, 267-272.
44. Huang, N., Nagarsekar, A., Xia, G., Hayashi, J., MacKerell, A. D., Jr. (2004) Identification of non-phosphate-containing small molecular weight inhibitors of the tyrosine kinase p56 Lck SH2 domain via in silico screening against the pY+3 binding site. J. Med. Chem., 47, 3502-3511.
45. Chen, F., Hancock, C. N., Macias, A. T., Joh, J., Still, K., Zhong, S., MacKerell, A. D., Jr., Shapiro, P. (2006) Characterization of ATP-independent ERK inhibitors identified through in silico analysis of the active ERK2 structure. Bioorg. Med. Chem. Lett., 16, 6281-6287.
46. Brooks, B. R., Brooks, C. L., III, MacKerell, A. D., Jr., Nilsson, L., Petrella, R. J., Roux, B., Won, Y., Archontis, G., Bartels, C., Boresch, S., et al. (2009) CHARMM: the biomolecular simulation program. J. Comput. Chem., 30, 1545-1614.
47. Phillips, J. C., Braun, R., Wang, W., Gumbart, J., Tajkhorshid, E., Villa, E., Chipot, C., Skeel, R. D., Kale, L., Schulten, K. (2005) Scalable molecular dynamics with NAMD. J. Comput. Chem., 26, 1781-1802.
48. Krumrine, J., Raubacher, F., Brooijmans, N., Kuntz, I. (2003) Principles and methods of docking and ligand design. Methods. Biochem. Anal., 44, 443-476.
49. Yang, D., Li, T., Liu, Z., Arbez, N., Yan, J., Moran, T. H., Ross, C. A., Smith, W. W. (2012) LRRK2 kinase activity mediates toxic interactions between genetic mutation and oxidative stress in a *Drosophila* model: Suppression by curcumin. Neurobiol. Dis., 47, 385-90.
50. Lee, M. K., Stirling, W., Xu, Y., Xu, X., Qui, D., Mandir, A. S., Dawson, T. M., Copeland, N. G., Jenkins, N. A., Price, D. L. (2002) Human alpha-synuclein-harboring familial Parkinson's disease-linked Ala-53→Thr mutation causes neurodegenerative disease with alpha-synuclein aggregation in transgenic mice. Proc. Natl. Acad. Sci. U.S.A, 99, 8968-8973.
51. Smith, W. W., Liu, Z., Liang, Y., Masuda, N., Swing, D. A., Jenkins, N. A., Copeland, N. G., Troncoso, J. C., Pletnikov, M., Dawson, T. M., et al. (2010) Synphilin-1 attenuates neuronal degeneration in the A53T {alpha}-synuclein transgenic mouse model. Hum. Mol. Genet., 19, 2087-98.
52. T. Gasser, "Genetics of Parkinson's disease," Current Opinion in Neurology, vol. 18, no. 4, pp. 363-369, 2005.
53. Dachsel, J. C.; Farrer, M. J. LRRK2 and Parkinson disease. Arch. Neurol. 2010, 67, 542-547.
54. Satake, W.; Nakabayashi, Y.; Mizuta, I.; Hirota, Y.; Ito, C.; Kubo, M.; Kawaguchi, T.; Tsunoda, T.; Watanabe, M.; Takeda, A.; Tomiyama, H.; Nakashima, K.; Hasegawa, K.; Obata, F.; Yoshikawa, T.; Kawakami, H.; Sakoda, S.; Yamamoto, M.; Hattori, N.; Murata, M.; Nakamura, Y.; Toda, T. Genome-wide association study identifies common variants at four loci as genetic risk factors for Parkinson's disease. Nat. Genet. 2009, 41, 1303-1307.
55. Simón-Sánchez, J.; Schulte, C.; Bras, J. M.; Sharma, M.; Gibbs, J. R.; Berg, D.; Paisan-Ruiz, C.; Lichtner, P.; Scholz, S. W.; Hernandez, D. G.; Krüger, R.; Federoff, M.; Klein, C.; Goate, A.; Perlmutter, J.; Bonin, M.; Nalls, M. A.; Illig, T.; Gieger, C.; Houlden, H.; Steffens, M.; Okun, M. S.; Racette, B. A.; Cookson, M. R.; Foote, K. D.; Fernandez, H. H.; Traynor, B. J.; Schreiber, S.; Arepalli, S.; Zonozi, R.; Gwinn, K.; van der Brug, M.; Lopez, G.; Chanock, S. J.; Schatzkin, A.; Park, Y.; Hollenbeck, A.; Gao, J.; Huang, X.; Wood, N. W.; Lorenz, D.; Deuschl, G.; Chen, H.; Riess, O.; Hardy, J. A.; Singleton, A. B.; Gasser, T. Genome-wide association study reveals genetic risk underlying Parkinson's disease. Nat. Genet. 2009, 41, 1308-1312.
56. Alastair D. Reith, Paul Bamborough, Karamjit Jandu, Daniele Andreotti, Lucy Mensah, Pamela Dossang, Hwan Geun Choi, Xianming Deng, Jinwei Zhang, Dario R. Alessi, Nathanael S. Gray. GSK2578215A; A potent and highly selective 2-arylmethyloxy-5-substitutent-N-aryl-benzamide LRRK2 kinase inhibitor, Bioorganic & Medicinal chemistry Letters, 2012, 22, 5625-5629.
57. Aasly J O, Vilariño-Güell C, Dachsel J C, Webber P J, West A B, Haugarvoll K, et al. Novel pathogenic LRRK2 p.Asn1437His substitution in familial Parkinson's disease. Mov Disord 2010; 25:2156-63; PMID:20669305; dx.doi.org/10.1002/mds.23265
58. Li T, Yang D, Zhong S, Thomas J M, Xue F, Liu J, et al. Novel LRRK2 GTP-binding inhibitors reduced degeneration in Parkinson's disease cell and mouse models. Hum Mol Genet. 2014; 23: 6212-22.
59. Fischer H, Gottschlich R, Seelig A. Blood-brain barrier permeation: molecular parameters governing passive diffusion. J Membr Biol. 1998; 165: 201-211.
60. Zhao L, Cao D, Chen T, Wang Y, Miao Z, Xu Y, et al. Fragment-based drug discovery of 2-thiazolidinones as inhibitors of the histone reader BRD4 bromodomain. J Med Chem. 2013; 56: 3833-3851.
61. Imai Y, Gehrke S, Wang H Q, Takahashi R, Hasegawa K, Oota E, et al. Phosphorylation of 4E-BP by LRRK2 affects the maintenance of dopaminergic neurons in *Drosophila*. EMBO J. 2008; 27: 2432-2443.
62. Dauer W, Przedborski S. Parkinson's disease. Mechanisms and models. Neuron. 2003; 39: 889-909.
63. Forno L S. Neuropathology of Parkinson's disease. J Neuropathol Exp Neurol. 1996; 55: 259-272.

64. Dawson T M, Dawson V L. Molecular pathways of neurodegeneration in Parkinson's disease. Science. 2003; 302: 819-822.

What is claimed is:

1. A compound selected from the group consisting of:

fx-2147 fx-2149 fx-2151 fx-2153 fx-2155 fx-2157

FX-3067

FX-3069

FX-3071

FX-3073

FX3075

FX3076

2. The compound of claim 1, wherein the compound is selected from the group consisting of:

fx-2149 fx-2147 fx-2153
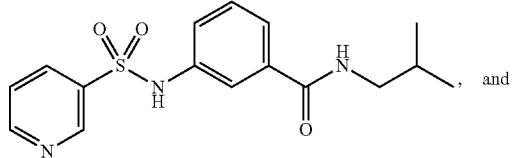
and
FX-3067
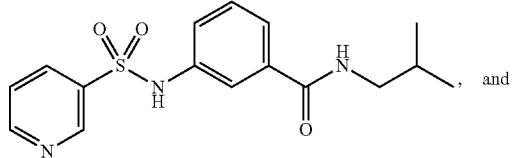
3. The compound of claim 1, wherein the compound is
fx-2149
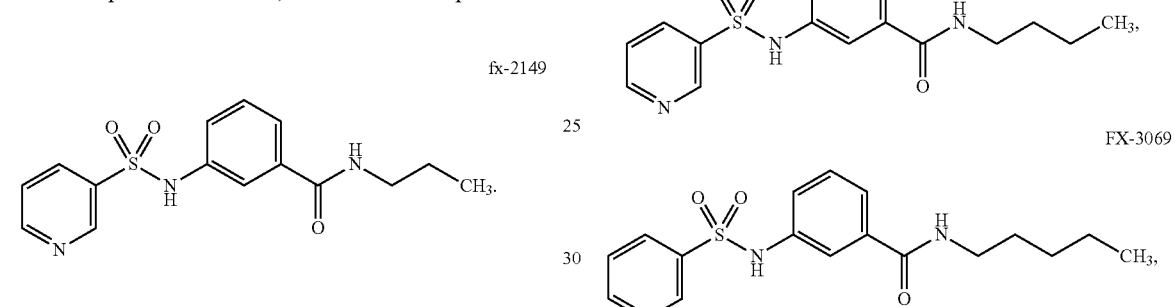
4. A pharmaceutical composition comprising a physiologically compatible carrier medium and at least one compound selected from the group consisting of:
fx-2147
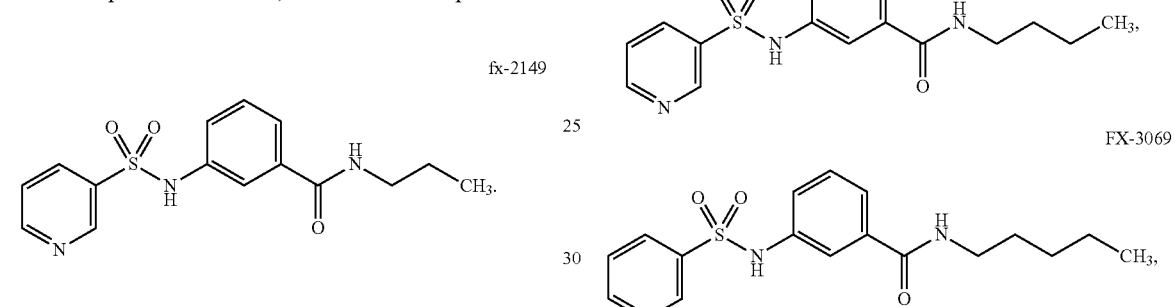
fx-2149
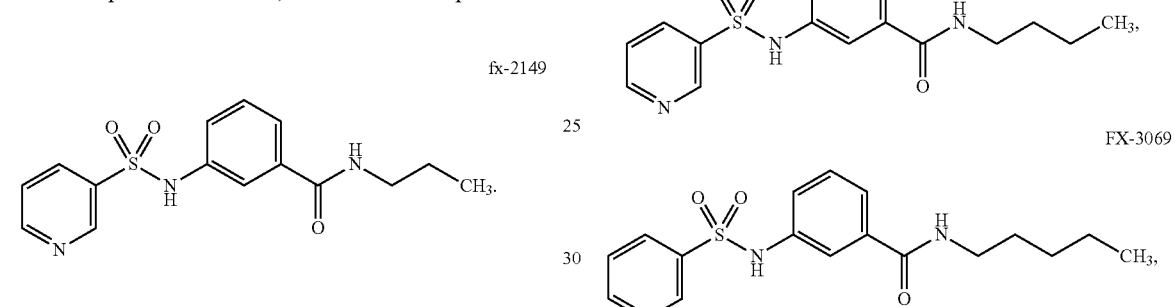
fx-2151
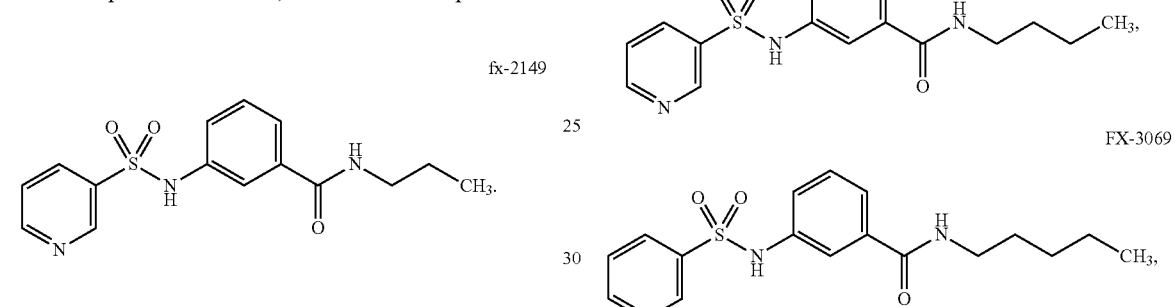
fx-2153
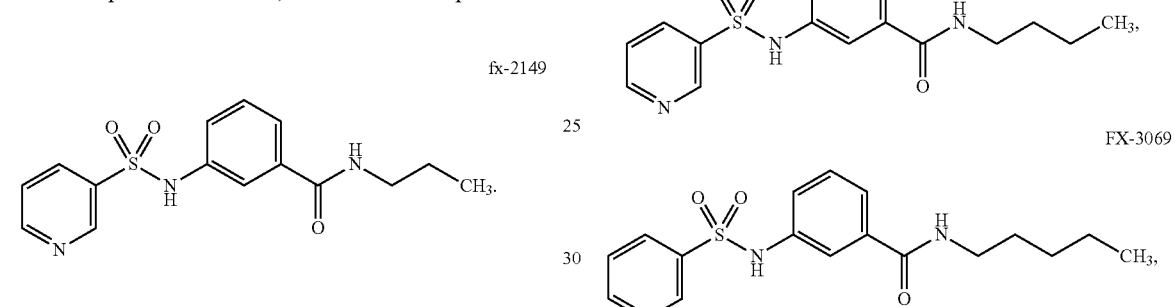
fx-2155
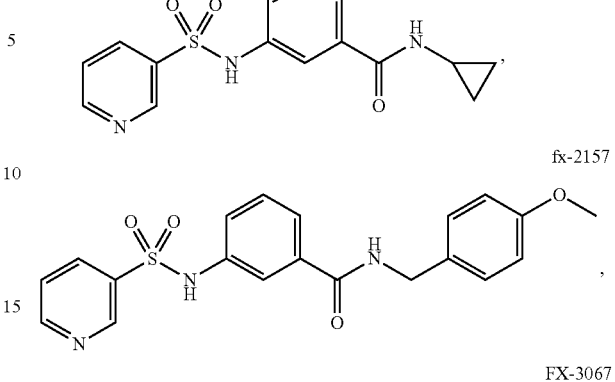
fx-2157
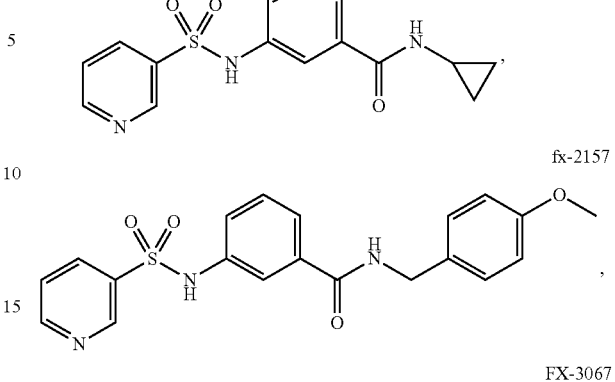
FX-3067
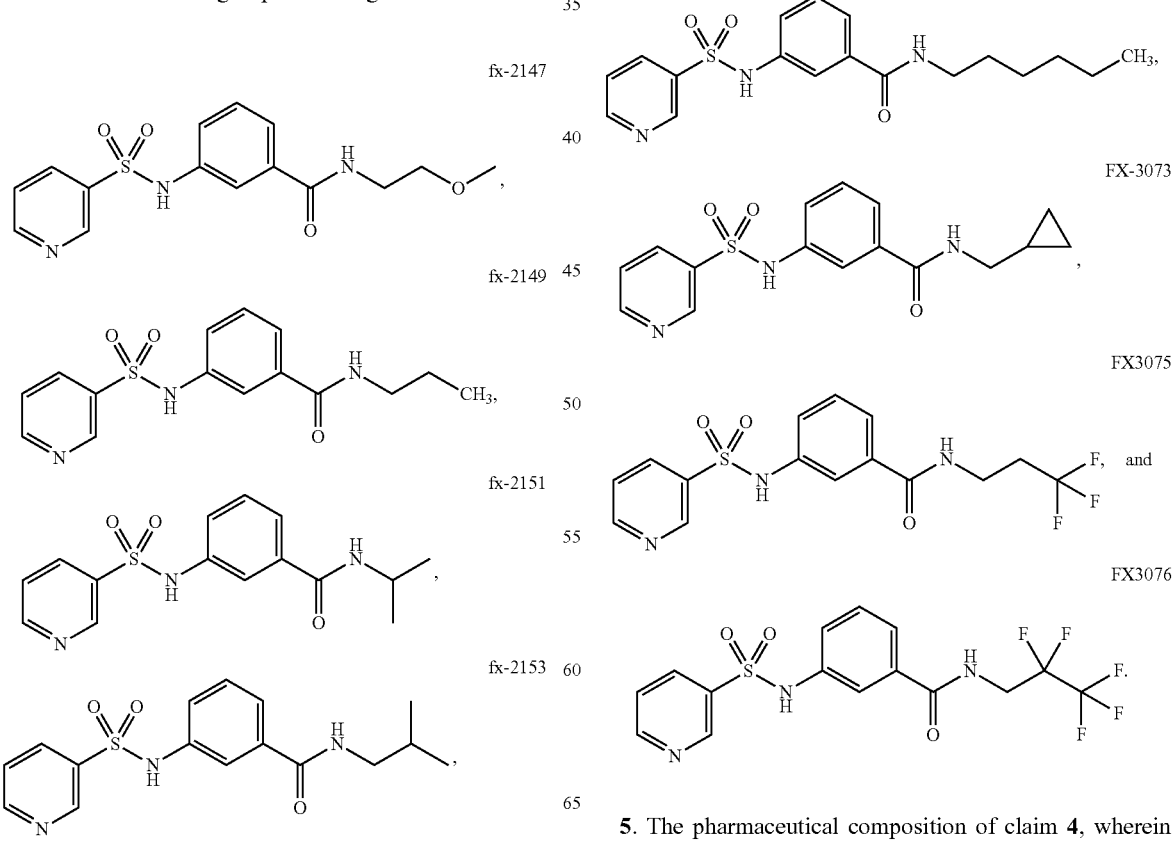
FX-3069
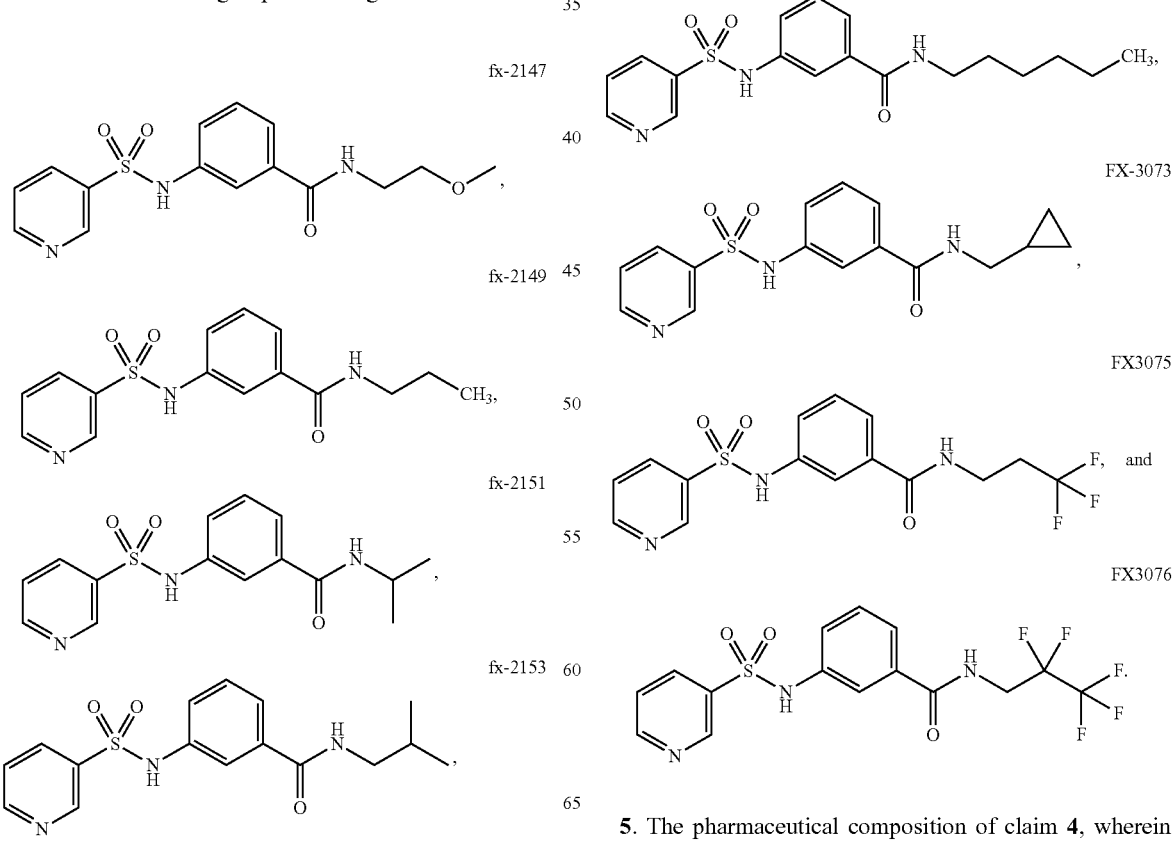
FX-3071
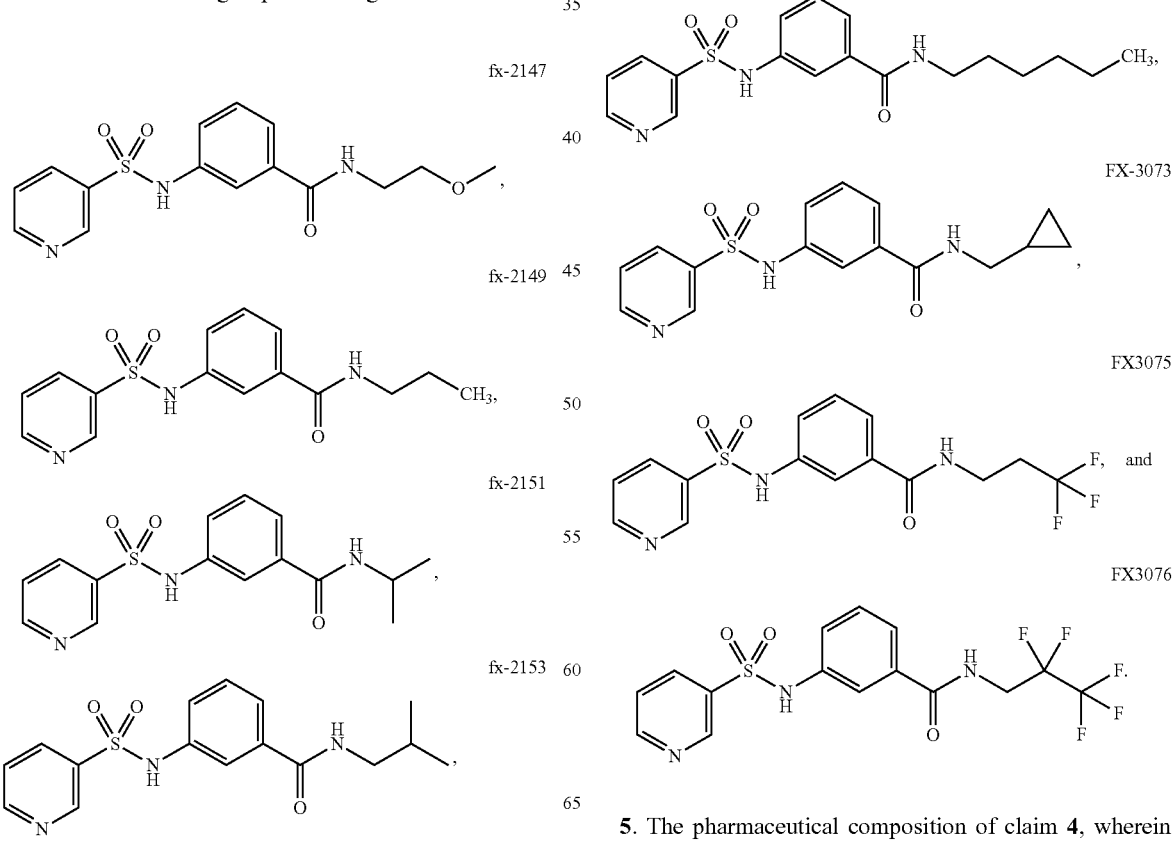
FX-3073
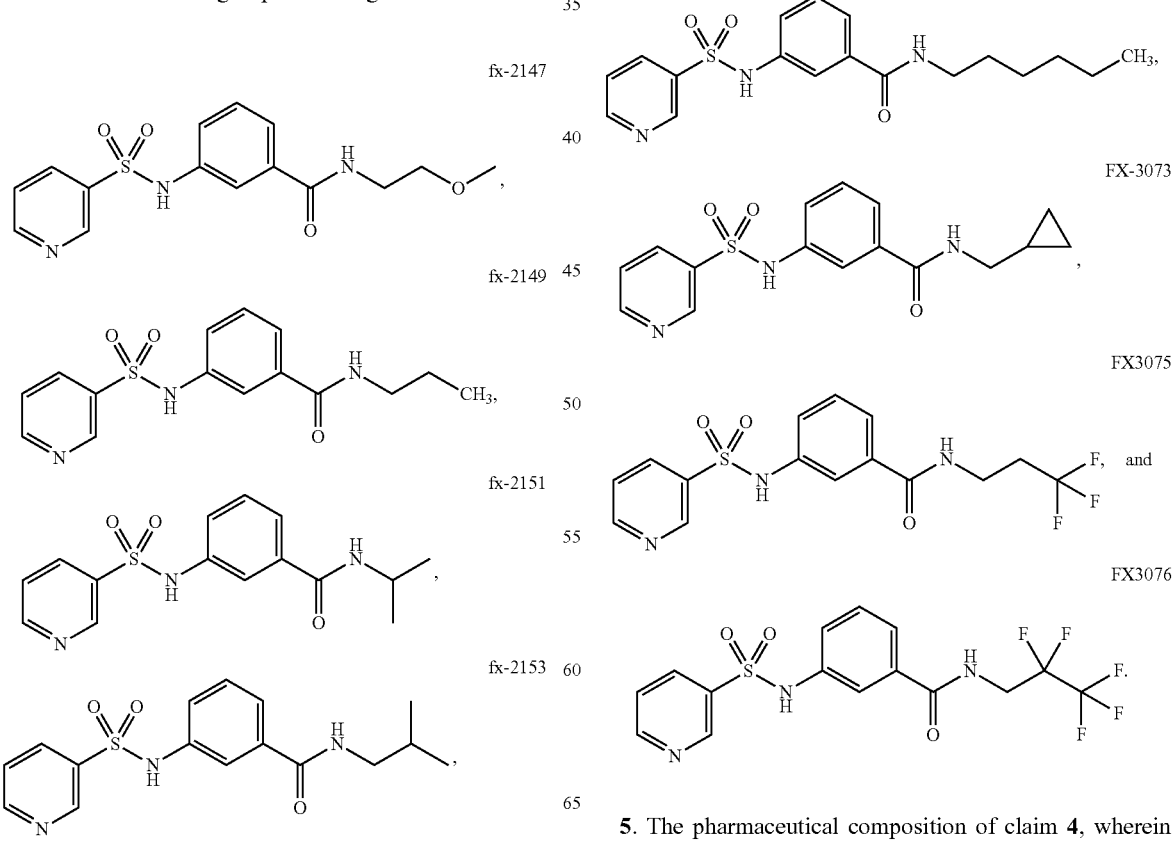
FX3075
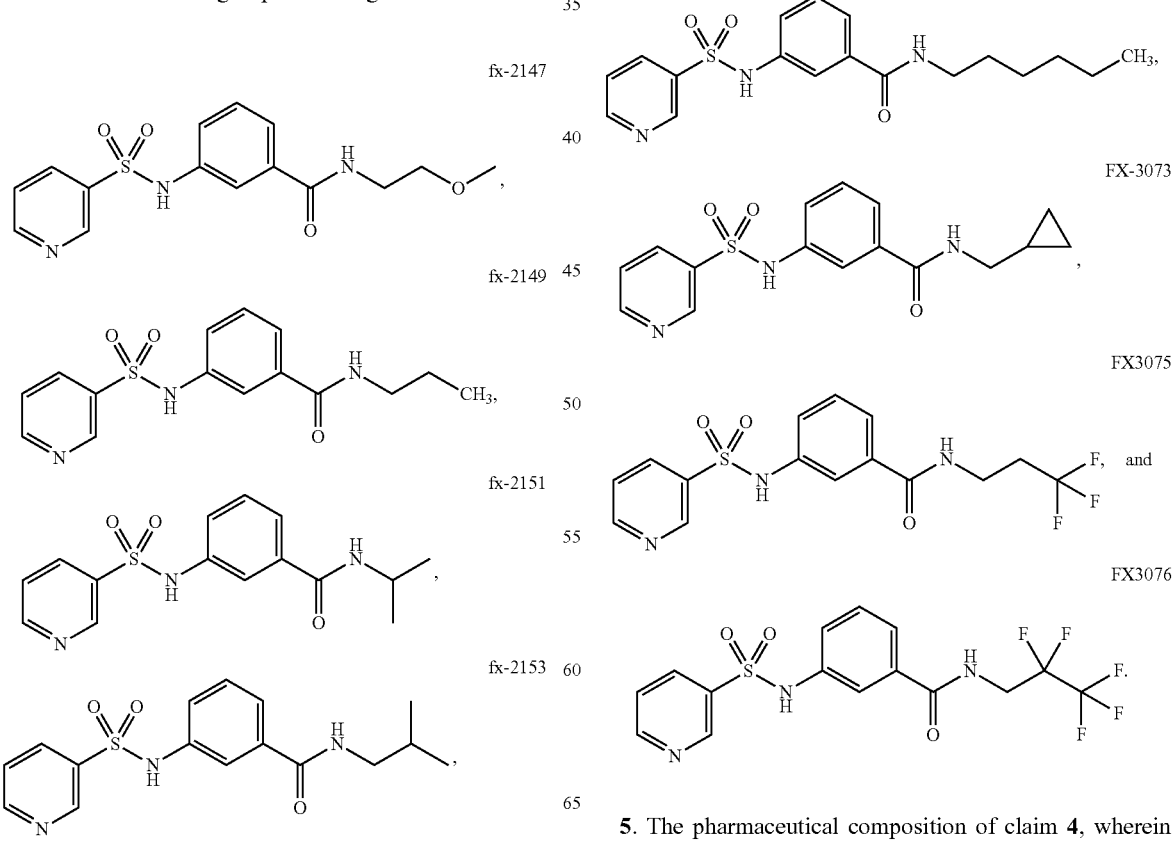
and
FX3076
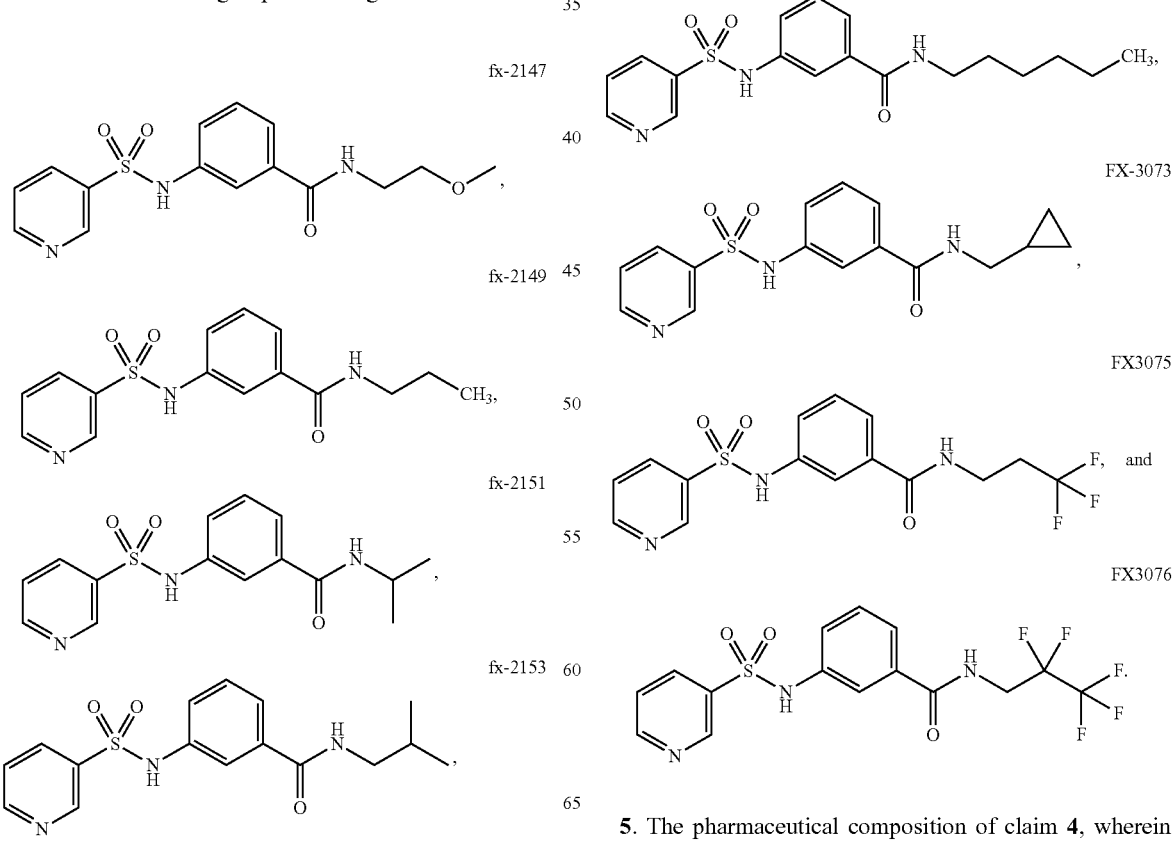
5. The pharmaceutical composition of claim 4, wherein the compound is selected from the group consisting of:

fx-2149
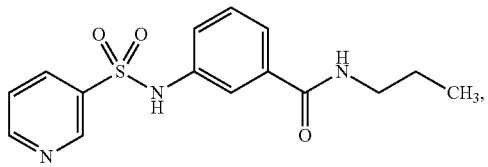
fx-2147
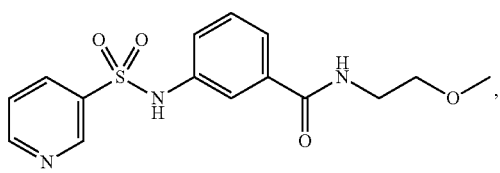
fx-2153
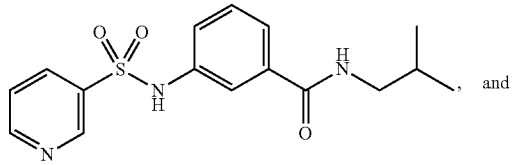, and
FX-3067
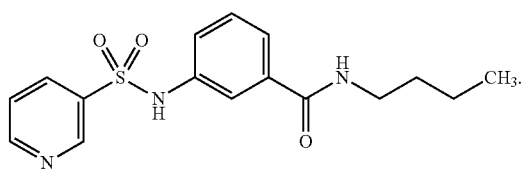
6. The pharmaceutical composition of claim 4, wherein the compound is
fx-2149
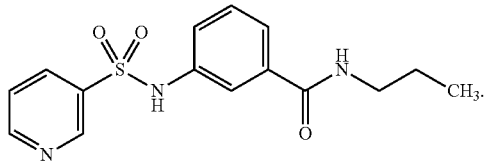
* * * * *